(12) United States Patent
Nagpal et al.

(10) Patent No.: US 11,747,463 B2
(45) Date of Patent: Sep. 5, 2023

(54) TECHNOLOGIES FOR TRACKING OBJECTS WITHIN DEFINED AREAS

(71) Applicant: Cherish Health, Inc., Cambridge, MA (US)

(72) Inventors: Sumit Kumar Nagpal, Boston, MA (US); Ryan Bendremer, Boston, MA (US); Patrick Conrad, Boston, MA (US); Elizabeth Elfenbein, Boston, MA (US); Rosy Leo, Boston, MA (US); Nitin Nataraj, Boston, MA (US); Aveen Nagpal, Boston, MA (US); Christoph Sahar, Boston, MA (US); Angela Su, Boston, MA (US); David Wang, Boston, MA (US); Rufino Rabin, Boston, MA (US)

(73) Assignee: Cherish Health, Inc., Boston, MA (US)

( * ) Notice: Subject to any disclaimer, the term of this patent is extended or adjusted under 35 U.S.C. 154(b) by 0 days.

(21) Appl. No.: 17/680,734

(22) Filed: Feb. 25, 2022

(65) Prior Publication Data

US 2022/0268916 A1    Aug. 25, 2022

Related U.S. Application Data

(60) Provisional application No. 63/162,476, filed on Mar. 17, 2021, provisional application No. 63/153,795, filed on Feb. 25, 2021.

(51) Int. Cl.
*G01S 13/72* (2006.01)
*G01S 13/86* (2006.01)
(Continued)

(52) U.S. Cl.
CPC .......... *G01S 13/723* (2013.01); *A61B 5/0507* (2013.01); *A61B 5/1113* (2013.01);
(Continued)

(58) Field of Classification Search
CPC ........ G01S 13/723; G01S 7/412; G01S 7/415; G01S 13/86; G01S 13/87; A61B 5/05;
(Continued)

(56) References Cited

U.S. PATENT DOCUMENTS 7,432,847 B2   10/2008   Fedotov et al.
8,428,696 B2    4/2013   Foo
(Continued)

FOREIGN PATENT DOCUMENTS

EP   1934628 B1   2/2010
EP   1977266 B1   4/2015
(Continued)

OTHER PUBLICATIONS

ADT Motion Sensors Tips and Tricks, <https://web.archive.org/web/20200928060148/https://www.adt.com/resources/motion-sensor-tips-and-tricks>, dated Sep. 28, 2020, accessed on Jul. 9, 2022 (Year: 2020).*

(Continued)

*Primary Examiner* — Donald H B Braswell
(74) *Attorney, Agent, or Firm* — Dentons US LLP

(57) ABSTRACT

This disclosure enables various technologies for tracking various objects (e.g., mammals, animals, humans, pets) within various defined areas (e.g., rooms, apartments, residences, vehicles, tents) to determine whether those objects satisfy or do not satisfy various criteria, signatures, or thresholds, which may relate to health, safety, or security of those objects within those defined areas. These technologies may be enabled via various radars (e.g., time-of-flight radars, Doppler radars) positioned within those defined areas to track those objects therein. For example, some of such radars may operate in a Ku-band inclusively between about 12 GHz and about 18 GHz, a K-band inclusively between about 18 GHz and about 27 GHz, or a Ka-band inclusively (Continued)

between about 26.5 GHz and about 40 GHz, each of which has been unexpectedly found to be technologically beneficial for tracking those objects within those defined areas.

30 Claims, 14 Drawing Sheets

(51) Int. Cl.
| | |
|---|---|
| G01S 13/87 | (2006.01) |
| H04R 3/00 | (2006.01) |
| G01S 7/41 | (2006.01) |
| H04R 1/40 | (2006.01) |
| A61B 5/11 | (2006.01) |
| A61B 5/0507 | (2021.01) |
| H04L 67/12 | (2022.01) |

(52) U.S. Cl.
CPC .............. *G01S 7/412* (2013.01); *G01S 7/415* (2013.01); *G01S 13/86* (2013.01); *G01S 13/87* (2013.01); *H04L 67/12* (2013.01); *H04R 1/406* (2013.01); *H04R 3/005* (2013.01)

(58) Field of Classification Search
CPC ....... A61B 5/0507; H04L 67/12; H04R 1/406; H04R 3/005
See application file for complete search history.

(56) References Cited

U.S. PATENT DOCUMENTS

| | | | |
|---|---|---|---|
| 8,454,528 B2 | 6/2013 | Yuen et al. | |
| 8,460,220 B2 | 6/2013 | Cuddihy | |
| 8,494,615 B2 | 7/2013 | Melamed et al. | |
| 8,742,935 B2 | 6/2014 | Cuddihy et al. | |
| 8,750,971 B2 | 6/2014 | Tran | |
| 8,781,563 B2 | 7/2014 | Foo | |
| 8,840,564 B2 | 9/2014 | Pinhas et al. | |
| 8,884,813 B2 | 11/2014 | Bangera et al. | |
| 9,019,149 B2 | 4/2015 | Bangera et al. | |
| 9,024,814 B2 | 5/2015 | Bangera et al. | |
| 9,069,067 B2 | 6/2015 | Bangera et al. | |
| 9,125,628 B2 | 9/2015 | Saitoh | |
| 9,131,902 B2 | 9/2015 | Haperin et al. | |
| 9,549,691 B2 | 1/2017 | Tran | |
| 9,615,765 B2 | 4/2017 | Chayat | |
| 9,753,131 B2 | 9/2017 | Adib et al. | |
| 9,766,332 B2 | 9/2017 | Ho et al. | |
| 9,883,821 B2 | 2/2018 | Muehlsteff | |
| 10,258,295 B2 | 4/2019 | Fountaine | |
| 10,307,084 B2 | 6/2019 | Forth et al. | |
| 10,410,498 B2 | 9/2019 | Coke et al. | |
| 10,438,473 B2 | 10/2019 | Findlay et al. | |
| 10,517,503 B2 | 12/2019 | Foo | |
| 10,536,572 B2 | 1/2020 | Youn | |
| 10,564,275 B2 | 2/2020 | Al-Alusi | |
| 10,617,330 B1 | 4/2020 | Joshi et al. | |
| 10,621,478 B2 | 4/2020 | Albadawi et al. | |
| 10,722,185 B2 | 7/2020 | Fountaine | |
| 10,743,100 B1 | 8/2020 | Eckert et al. | |
| 10,746,852 B2 | 8/2020 | Adib et al. | |
| 10,810,850 B2 | 10/2020 | Eckert et al. | |
| 10,825,314 B2 | 11/2020 | White et al. | |
| 11,020,064 B2 | 6/2021 | Fountaine | |
| 11,024,142 B2 | 6/2021 | Tunnell et al. | |
| 11,410,540 B2* | 8/2022 | Zhang .................... G06V 20/52 | |
| 11,450,192 B2* | 9/2022 | Lin ....................... A61B 5/7275 | |
| 2005/0046584 A1 | 3/2005 | Breed | |
| 2006/0267652 A1 | 11/2006 | Kabelly et al. | |
| 2007/0085690 A1 | 4/2007 | Tran | |
| 2008/0007445 A1* | 1/2008 | Leach, Jr. ................. H01Q 7/00 343/866 | |
| 2008/0294019 A1 | 11/2008 | Tran | |
| 2009/0033548 A1 | 2/2009 | Boxman et al. | |
| 2011/0205121 A1 | 8/2011 | Hochdorf et al. | |
| 2013/0002434 A1* | 1/2013 | Cuddihy ................. G01S 13/18 342/28 | |
| 2013/0300573 A1 | 11/2013 | Brown et al. | |
| 2014/0055297 A1 | 2/2014 | Beeri et al. | |
| 2014/0378809 A1 | 12/2014 | Weitnauer et al. | |
| 2017/0154516 A1 | 6/2017 | German | |
| 2018/0143318 A1 | 5/2018 | Skowronek et al. | |
| 2018/0352356 A1 | 12/2018 | Amir | |
| 2019/0057777 A1 | 2/2019 | Joshi et al. | |
| 2019/0108913 A1 | 4/2019 | Coke et al. | |
| 2019/0139389 A1 | 5/2019 | White et al. | |
| 2019/0162821 A1 | 5/2019 | Rafrafi et al. | |
| 2019/0188533 A1 | 6/2019 | Katabi et al. | |
| 2019/0193280 A1 | 6/2019 | Mendelsohn et al. | |
| 2019/0197861 A1 | 6/2019 | Tunnell | |
| 2019/0216393 A1 | 7/2019 | Baheti et al. | |
| 2019/0254544 A1 | 8/2019 | Chayat et al. | |
| 2019/0265345 A1 | 8/2019 | Jungmaier et al. | |
| 2019/0273702 A1 | 9/2019 | Zweig et al. | |
| 2019/0392327 A1 | 12/2019 | Zweig et al. | |
| 2020/0064784 A1* | 2/2020 | Steiner .................... G01S 7/415 | |
| 2020/0082551 A1 | 3/2020 | Steiner | |
| 2020/0135198 A1 | 4/2020 | Mandl et al. | |
| 2020/0146550 A1 | 5/2020 | Tunnell et al. | |
| 2020/0158849 A1 | 5/2020 | Joshi et al. | |
| 2020/0178838 A1 | 6/2020 | Melamed | |
| 2020/0178892 A1 | 6/2020 | Maslik et al. | |
| 2020/0196866 A1 | 6/2020 | Chiou et al. | |
| 2020/0200892 A1 | 6/2020 | Rajab et al. | |
| 2020/0202177 A1 | 6/2020 | Ruibas et al. | |
| 2020/0219412 A1 | 7/2020 | Amir et al. | |
| 2020/0219608 A1 | 7/2020 | Amir et al. | |
| 2020/0258364 A1* | 8/2020 | Quilici ................. G08B 21/043 | |
| 2020/0264278 A1* | 8/2020 | Eckert ....................... G01S 7/003 | |
| 2020/0265698 A1 | 8/2020 | Eckert et al. | |
| 2020/0278422 A1 | 9/2020 | Lien et al. | |
| 2020/0284892 A1 | 9/2020 | Lee et al. | |
| 2020/0319327 A1 | 10/2020 | Tsvelykh et al. | |
| 2020/0329358 A1 | 10/2020 | Hamre et al. | |
| 2020/0383608 A1 | 12/2020 | Ramesh et al. | |
| 2020/0390339 A1 | 12/2020 | White et al. | |
| 2020/0397310 A1 | 12/2020 | Gu et al. | |
| 2020/0408875 A1* | 12/2020 | Mai ......................... G01S 7/006 | |
| 2021/0035425 A1 | 2/2021 | Eckert et al. | |
| 2021/0038170 A1 | 2/2021 | Fountaine | |
| 2021/0055385 A1 | 2/2021 | Rimini et al. | |
| 2021/0055386 A1 | 2/2021 | Rimini et al. | |
| 2021/0057093 A1 | 2/2021 | deSa et al. | |
| 2021/0057101 A1 | 2/2021 | deSa et al. | |
| 2021/0059543 A1 | 3/2021 | Pai et al. | |
| 2021/0063214 A1 | 3/2021 | Li et al. | |
| 2021/0136515 A1* | 5/2021 | Zhang ..................... H04W 4/023 | |
| 2021/0153818 A1 | 5/2021 | Fountaine | |
| 2021/0177343 A1 | 6/2021 | Zhong et al. | |
| 2022/0029716 A1 | 1/2022 | Daisy et al. | |
| 2022/0331028 A1* | 10/2022 | Sternitzke ............. A61B 5/1176 | |

FOREIGN PATENT DOCUMENTS

| | | |
|---|---|---|
| IL | 170726 B | 12/2011 |
| IL | 187708 | 4/2013 |
| JP | 2019518515 | 7/2019 |
| WO | WO2007099524 | 9/2007 |
| WO | WO2007113824 | 10/2007 |
| WO | WO2008129538 | 10/2008 |
| WO | WO2017/062566 | 4/2017 |
| WO | WO2018078627 | 5/2018 |
| WO | WO2020/008458 | 1/2020 |
| WO | WO2020207649 | 10/2020 |

OTHER PUBLICATIONS

Li, et al, Experiment and Spectral Analysis of Low-Power Ka-Band Heartbeat Detector Measuring From Four Sides of a Human Body; IEEE Transactions on Microwave Theory; vol. 4, No. 12; Dec. 2006; DOI: 10.1109/TMTT.2006.884652 (Year: 2006).*

(56) References Cited

OTHER PUBLICATIONS

Alexa Together, Introducing a new service to help you care for the ones you love, downloaded from internet Mar. 17, 2022, https://www.amazon.com/Alexa-Together/b?ie=UTF8&node=21390531011 (11 pages).

Anthropos, Connected care supporting older people to live well at home for longer, downloaded from internet Mar. 17, 2022, https://anthropos.io/ (15 pages).

Care.AI, Innovating the next evolution of Healthcare, Smart Care Facility Platform, downloaded from internet Mar. 17, 2022, https://www.care.ai/technology.html (4 pages).

Hackett, Israeli startup Donisi Health lands De Novo for AI-enabled contactless monitor, 2021, MobiHealth News (4 pages).

International Search Report and Written Opinion dated Jul. 8, 2022 in application No. PCT/US22/17808 filed Feb. 25, 2022 (36 pages).

\* cited by examiner

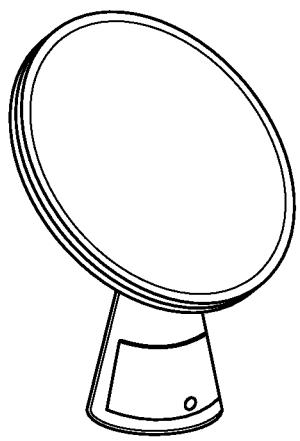
Speaker
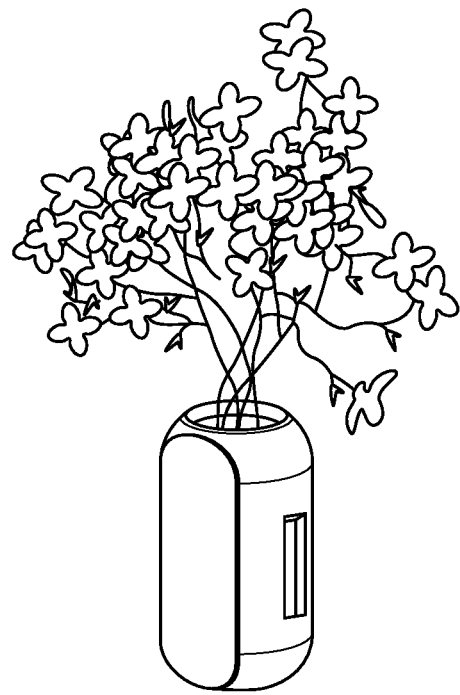
Flower Pot, Planter Pot, or Vase
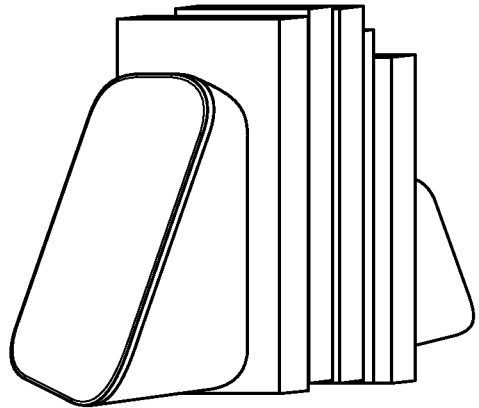
Bookend
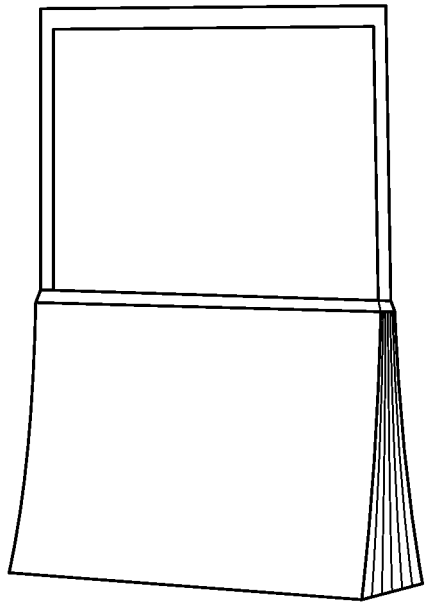
Stand
FIG. 9

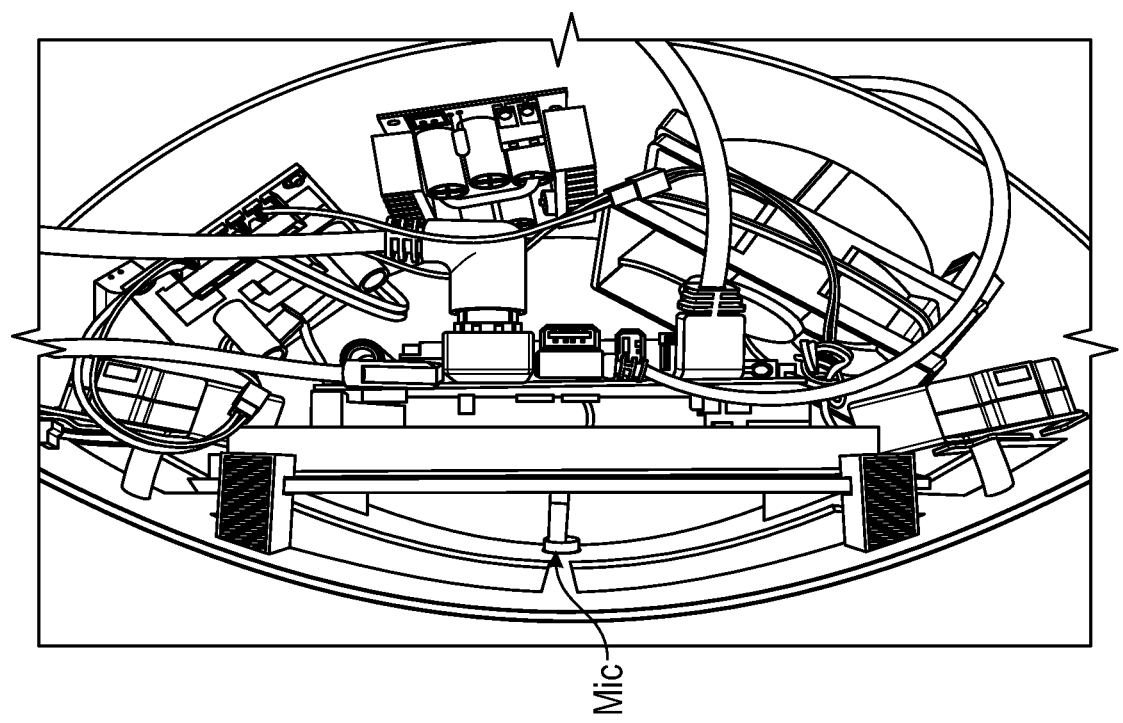
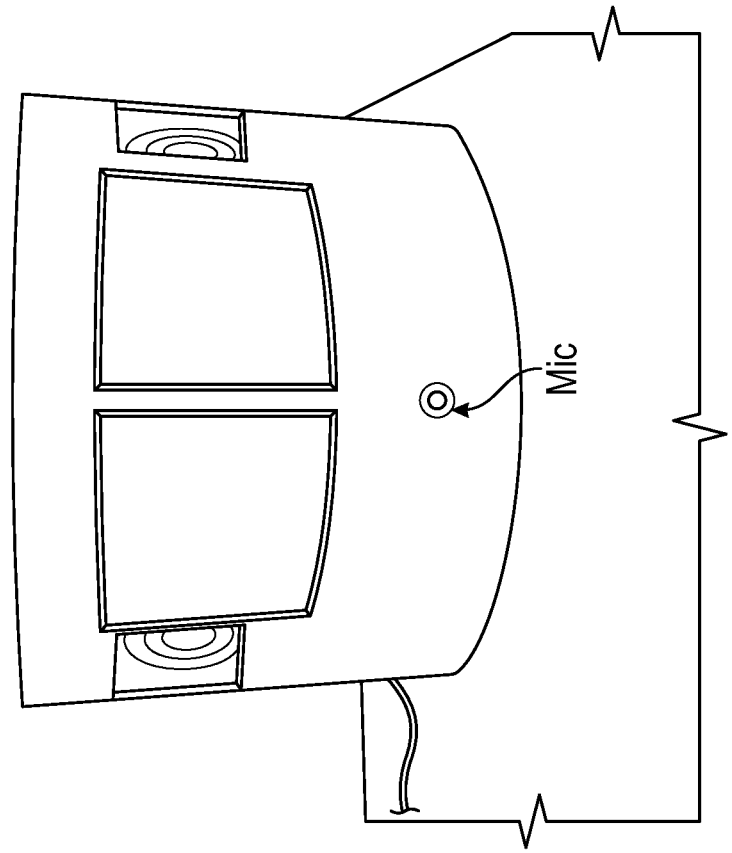
FIG. 13

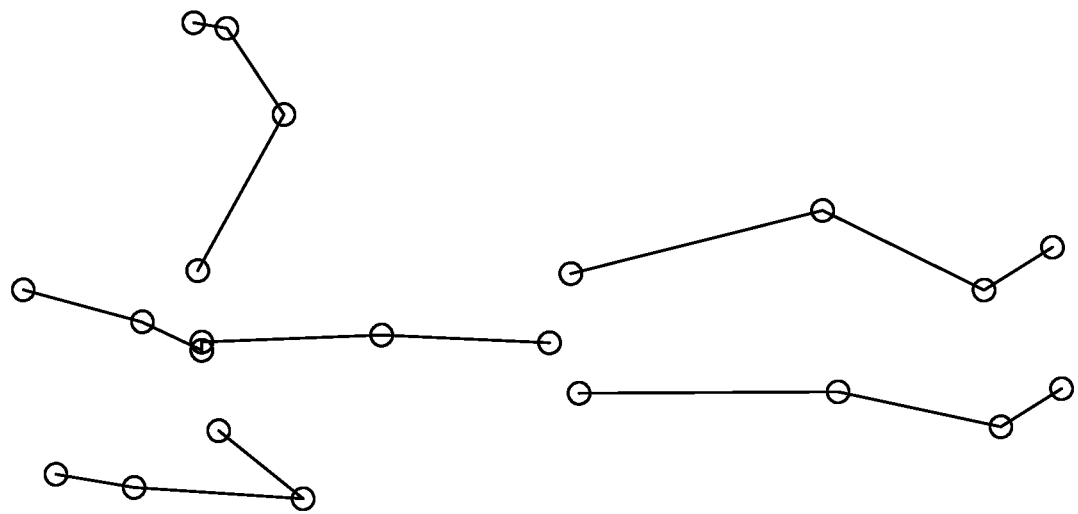
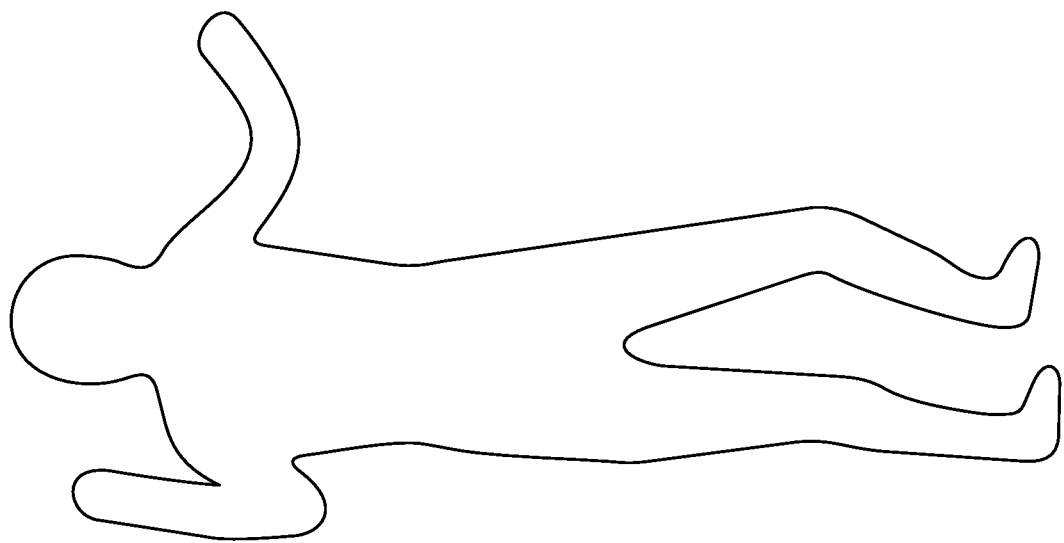
FIG. 14

TECHNOLOGIES FOR TRACKING OBJECTS WITHIN DEFINED AREAS

CROSS-REFERENCE TO RELATED PATENT APPLICATIONS

This patent application claims a benefit of priority to US Provisional Patent Application 63/153,795 filed 25 Feb. 2021; which is incorporated by reference herein for all purposes.

This patent application claims a benefit of priority to U.S. Provisional Patent Application 63/162,476 filed 17 Mar. 2021; which is incorporated by reference herein for all purposes.

TECHNICAL FIELD

This disclosure relates to tracking objects within defined areas.

BACKGROUND

A first person (e.g., a caregiver, a doctor, a family member, a social worker, a home care worker) may desire to track a second person (e.g., a care recipient, a patient) within a defined area (e.g., a room, an apartment) to ensure that the second person is safe, healthy, or secure within the defined area. However, doing so may be technologically problematic for various reasons. For example, the second person may want to maintain some sense of privacy with respect to such tracking or ensure that such tracking is secure. Likewise, whatever technology the first person decides to use for such tracking (e.g., a video camera, a proximity sensor) may have various technological shortcomings (e.g., a coverage gap, an insufficient accuracy).

SUMMARY

This disclosure enables various technologies for tracking various objects (e.g., animals, humans, pets) within various defined areas (e.g., rooms, apartments, residences, offices, tents, barracks, vehicles, aircraft, spacecraft, clinics, field-clinics, hospitals, field-hospitals) to determine whether those objects satisfy or do not satisfy various criteria, signatures, or thresholds, which may relate to health, safety, or security of those objects within those defined areas or environments inhabited by those objects. These technologies may be enabled via various radars (e.g., time-of-flight radars, Doppler radars) positioned within those defined areas to track those objects therein. For example, some of such radars may operate in a Ku-band inclusively between about 12 GHz and about 18 GHz, a K-band inclusively between about 18 GHz and about 27 GHz, or a Ka-band inclusively between about 26.5 GHz and about 40 GHz, each of which has been unexpectedly found to be technologically beneficial for tracking those objects within those defined areas.

An embodiment may include a method comprising: providing a device to a user, wherein the device includes a processor and a time-of-flight radar, wherein the processor is coupled to the time-of-flight radar, wherein the time-of-flight radar is configured to operate in a K-band; and instructing the user to: position the device within a defined area having an object living therein, and activate the time-of-flight radar to operate in the K-band within the defined area such that the time-of-flight radar operating in the K-band within the defined area tracks the object living in the defined area, generates a set of data based on tracking the object living in the defined area, and sends the set of data to the processor such that the processor determines whether the object is experiencing an event within the defined area based on the set of data and takes an action responsive to the event determined to be occurring within the defined area.

An embodiment may include a method comprising: receiving, by a processor, a set of data from a time-of-flight radar operating in a K-band within a defined area having an object living therein, wherein the time-of-flight radar generating the set of data based on the time-of-flight radar operating in the K-band within the defined area and tracking the object living in the defined area; determining, by the processor, whether the object is experiencing an event within the defined area based on the set of data; and taking, by the processor, an action responsive to the event determined to be occurring within the defined area.

An embodiment may include a system comprising: a device including a processor and a time-of-flight radar, wherein the processor is coupled to the time-of-flight radar, wherein the time-of-flight radar is configured to operate in a K-band, wherein the device is configured to be positioned within a defined area having an object living therein such that the time-of-flight radar operating in the K-band within the defined area tracks the object living in the defined area, generates a set of data based on tracking the object living in the defined area, and sends the set of data to the processor such that the processor determines whether the object is experiencing an event within the defined area based on the set of data and takes an action responsive to the event determined to be occurring within the defined area.

An embodiment may include a method comprising: providing a device to a user, wherein the device includes a processor and a radar, wherein the processor is coupled to the radar; and instructing the user to: position the device within a defined area having an object therein, and activate the radar to operate within the defined area such that the radar operating within the defined area tracks the object in the defined area, generates a set of data based on tracking the object in the defined area, and sends the set of data to the processor such that the processor determines whether an action should be taken based on the set of data and takes the action based on the set of data.

An embodiment may include a method comprising: receiving, by a processor, a set of data from a radar operating within a defined area having an object therein, wherein the radar generating the set of data based on the radar operating within the defined area and tracking the object in the defined area; determining, by the processor, whether an action should be taken based on the set of data; and taking, by the processor, the action based on the set of data.

An embodiment may include a system comprising: a device including a processor and a radar, wherein the processor is coupled to the radar, wherein the device is configured to be positioned within a defined area having an object therein such that the radar within the defined area tracks the object in the defined area, generates a set of data based on tracking the object in the defined area, and sends the set of data to the processor such that the processor determines whether an action should be taken based on the set of data and takes the action based on the set of data.

An embodiment may include a method comprising: positioning a device within a defined area having an object therein, wherein the device includes a processor and a radar, wherein the processor is coupled to the radar; and activating the radar to operate within the defined area such that the radar operating within the defined area tracks the object in the defined area, generates a set of data based on tracking the object in the defined area, and sends the set of data to the processor such that the processor determines whether an action should be taken based on the set of data and takes the action based on the set of data.

An embodiment may include a device comprising: a vehicle including a processor, a radar, and an area, wherein the processor is coupled to the radar, wherein the area is configured to contain a driver or a passenger, wherein the processor is programmed to activate the radar to track the driver or the passenger within the area, generate a set of data based on tracking the driver or the passenger in the area, and send the set of data to the processor such that the processor determines whether an action should be taken based on the set of data and takes the action based on the set of data.

DESCRIPTION OF DRAWINGS

FIG. 9 shows a set of embodiments of a set of form factors embodying a radar according to this disclosure.

FIG. 13 shows an embodiment of a microphone of the device of FIG. 7 according to this disclosure.

FIG. 14 shows an embodiment of a raw reading from the device of FIGS. 1-7 and a virtual skeleton formed by the device of FIGS. 1-7 from the raw reading according to this disclosure.

DETAILED DESCRIPTION

Figure 1:
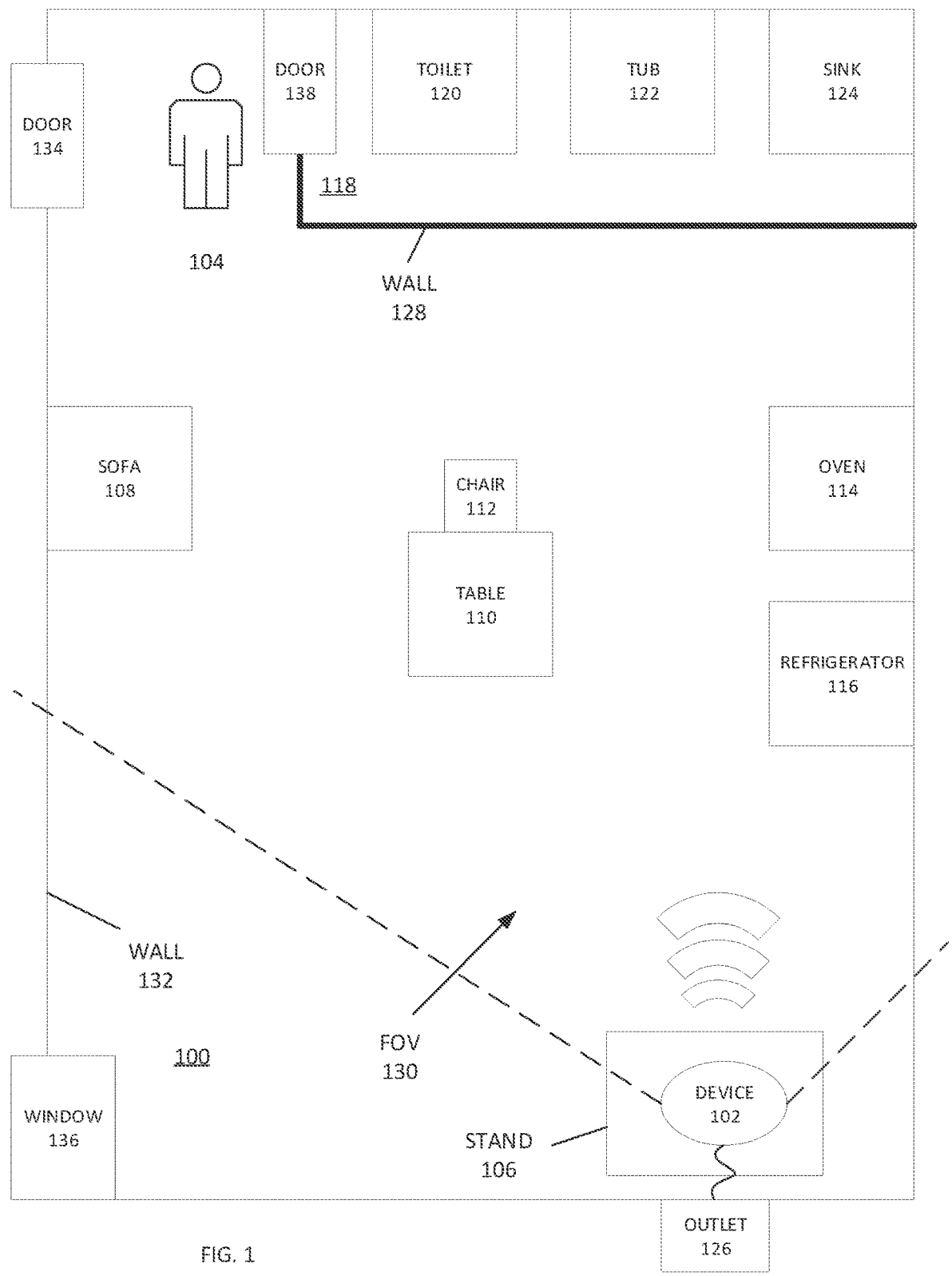
FIG. 1 shows a top view diagram of an embodiment of an area containing a device including a radar according to this disclosure.

This disclosure enables various technologies for tracking various objects (e.g., mammals, animals, humans, pets) within various defined areas (e.g., rooms, apartments, residences, vehicles, tents) to determine whether those objects satisfy or do not satisfy various criteria, signatures, or thresholds, which may relate to health, safety, or security of those objects within those defined areas. These technologies may be enabled via various radars (e.g., time-of-flight radars, Doppler radars) positioned within those defined areas to track those objects therein. For example, some of such radars may operate in a Ku-band inclusively between about 12 GHz and about 18 GHz, a K-band inclusively between about 18 GHz and about 27 GHz, or a Ka-band inclusively between about 26.5 GHz and about 40 GHz, each of which has been unexpectedly found to be technologically beneficial for tracking those objects within those defined areas, as further explained below.

This disclosure is now described more fully with reference to all attached figures, in which some embodiments of this disclosure are shown. This disclosure may, however, be embodied in many different forms and should not be construed as necessarily being limited to various embodiments disclosed herein. Rather, these embodiments are provided so that this disclosure is thorough and complete, and fully conveys various concepts of this disclosure to skilled artisans. Note that like numbers or similar numbering schemes can refer to like or similar elements throughout.

Various terminology used herein can imply direct or indirect, full or partial, temporary or permanent, action or inaction. For example, when an element is referred to as being "on," "connected" or "coupled" to another element, then the element can be directly on, connected or coupled to the other element or intervening elements can be present, including indirect or direct variants. In contrast, when an element is referred to as being "directly connected" or "directly coupled" to another element, there are no intervening elements present.

As used herein, a term "or" is intended to mean an inclusive "or" rather than an exclusive "or." That is, unless specified otherwise, or clear from context, "X employs A or B" is intended to mean any of natural inclusive permutations. That is, if X employs A; X employs B; or X employs both A and B, then "X employs A or B" is satisfied under any of the foregoing instances. For example, X includes A or B can mean X can include A, X can include B, and X can include A and B, unless specified otherwise or clear from context.

As used herein, each of singular terms "a," "an," and "the" is intended to include a plural form (e.g., two, three, four, five, six, seven, eight, nine, ten, tens, hundreds, thousands, millions) as well, including intermediate whole or decimal forms (e.g., 0.0, 0.00, 0.000), unless context clearly indicates otherwise. Likewise, each of singular terms "a," "an," and "the" shall mean "one or more," even though a phrase "one or more" may also be used herein.

As used herein, each of terms "comprises," "includes," or "comprising," "including" specify a presence of stated features, integers, steps, operations, elements, or components, but do not preclude a presence or addition of one or more other features, integers, steps, operations, elements, components, or groups thereof.

As used herein, when this disclosure states herein that something is "based on" something else, then such statement refers to a basis which may be based on one or more other things as well. In other words, unless expressly indicated otherwise, as used herein "based on" inclusively means "based at least in part on" or "based at least partially on."

As used herein, terms, such as "then," "next," or other similar forms are not intended to limit an order of steps. Rather, these terms are simply used to guide a reader through this disclosure. Although process flow diagrams may describe some operations as a sequential process, many of those operations can be performed in parallel or concurrently. In addition, the order of operations may be rearranged.

As used herein, a term "response" or "responsive" are intended to include a machine-sourced action or inaction, such as an input (e.g., local, remote), or a user-sourced action or inaction, such as an input (e.g., via user input device).

As used herein, a term "about" or "substantially" refers to a +/−10% variation from a nominal value/term.

Although various terms, such as first, second, third, and so forth can be used herein to describe various elements, components, regions, layers, or sections, note that these elements, components, regions, layers, or sections should not necessarily be limited by such terms. Rather, these terms are used to distinguish one element, component, region, layer, or section from another element, component, region, layer, or section. As such, a first element, component, region, layer, or section discussed below could be termed a second element, component, region, layer, or section, without departing from this disclosure.

Unless otherwise defined, all terms (including technical and scientific terms) used herein have a same meaning as commonly understood by skilled artisans to which this disclosure belongs. These terms, such as those defined in commonly used dictionaries, should be interpreted as having a meaning that is consistent with their meaning in context of relevant art and should not be interpreted in an idealized or overly formal sense, unless expressly so defined herein.

Features or functionality described with respect to certain embodiments may be combined and sub-combined in or with various other embodiments. Also, different aspects, components, or elements of embodiments, as disclosed herein, may be combined and sub-combined in a similar manner as well. Further, some embodiments, whether individually or collectively, may be components of a larger system, wherein other procedures may take precedence over or otherwise modify their application. Additionally, a number of steps may be required before, after, or concurrently with embodiments, as disclosed herein. Note that any or all methods or processes, as disclosed herein, can be at least partially performed via at least one entity or actor in any manner.

Hereby, all issued patents, published patent applications, and non-patent publications that are mentioned or referred to in this disclosure are herein incorporated by reference in their entirety for all purposes, to a same extent as if each individual issued patent, published patent application, or non-patent publication were specifically and individually indicated to be incorporated by reference. To be even more clear, all incorporations by reference specifically include those incorporated publications as if those specific publications are copied and pasted herein, as if originally included in this disclosure for all purposes of this disclosure. Therefore, any reference to something being disclosed herein includes all subject matter incorporated by reference, as explained above. However, if any disclosures are incorporated herein by reference and such disclosures conflict in part or in whole with this disclosure, then to an extent of the conflict or broader disclosure or broader definition of terms, this disclosure controls. If such disclosures conflict in part or in whole with one another, then to an extent of conflict, the later-dated disclosure controls.

Figure 2:
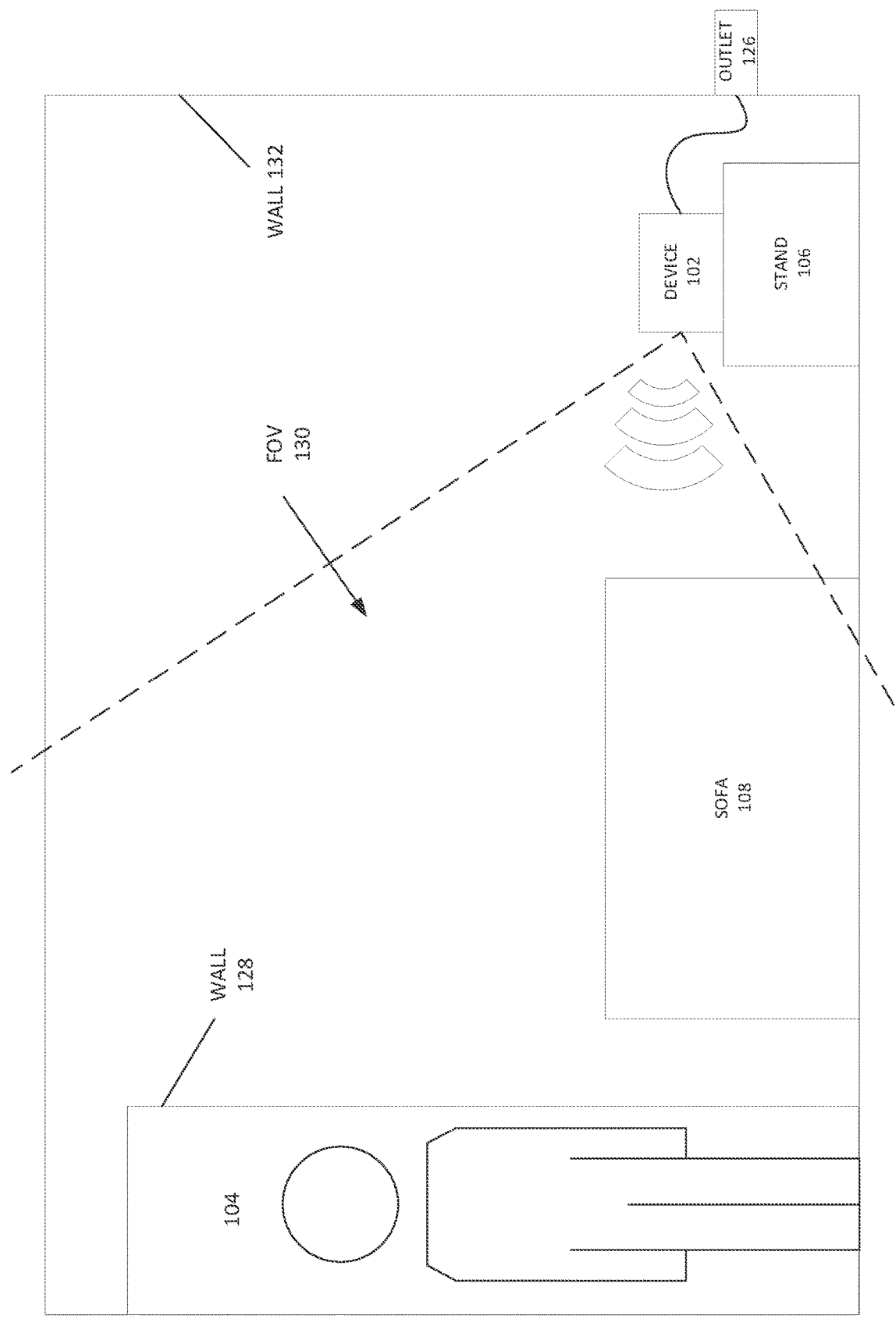
FIG. 2 shows a side view diagram of FIG. 1 according to this disclosure.
Figure 7:
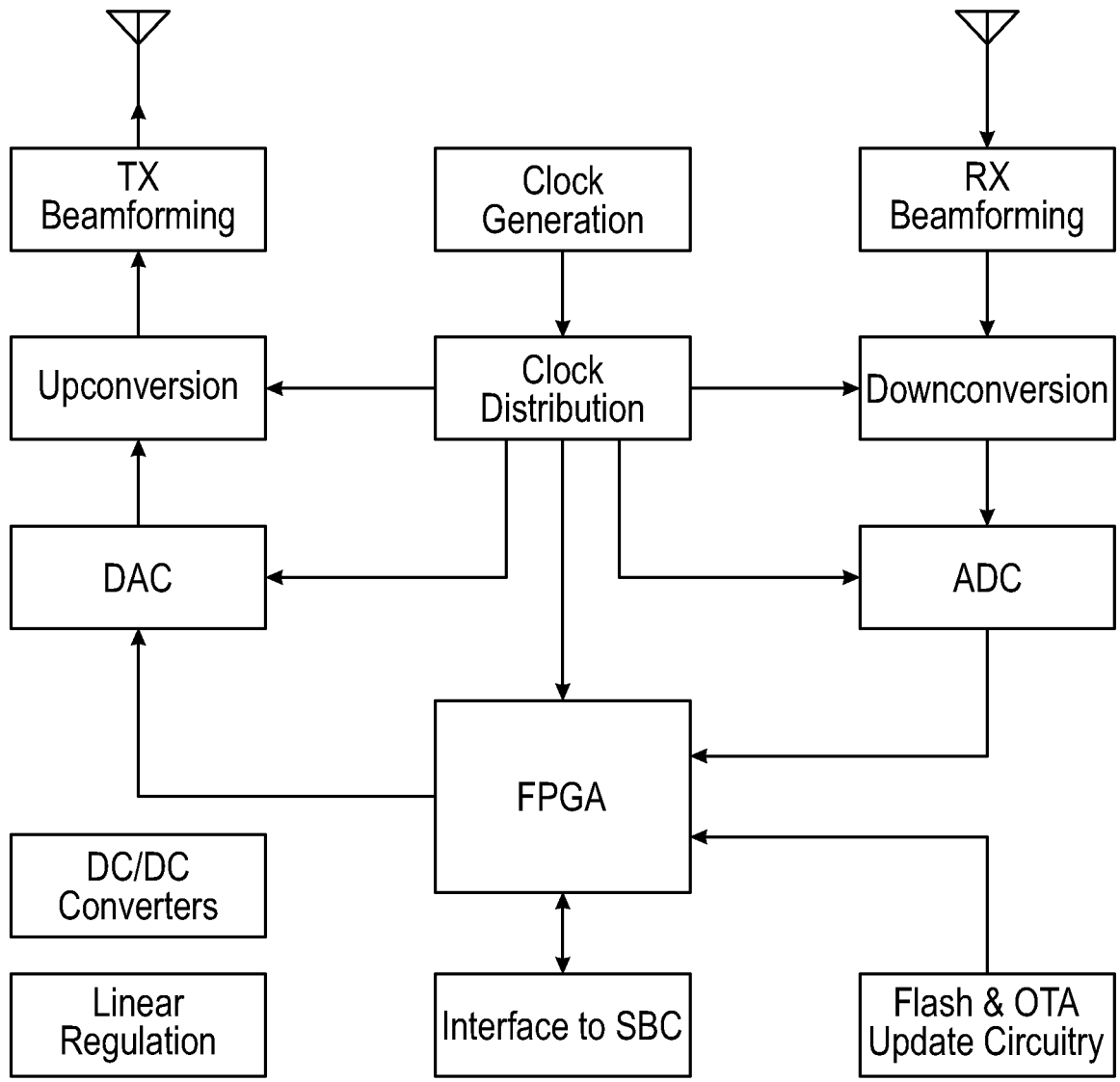
FIG. 7 shows a logic diagram of a radar according to this disclosure.

FIG. 1 shows a top view diagram of an embodiment of an area containing a device including a radar according to this disclosure. FIG. 2 shows a side view diagram of FIG. 1 according to this disclosure. FIG. 7 shows a logic diagram of a radar according to this disclosure. FIG. 9 shows a set of embodiments of a set of form factors embodying a radar according to this disclosure. In particular, an area 100 contains a device 102, an object 104, a stand 106, a sofa 108, a table 110, a chair 112, an oven 114, a refrigerator 116, a bathroom 118, a toilet 120, a tub 122, a sink 124, an electrical outlet 126, a wall 128, a field of view 130, a wall 132, a door 134, and a door 138.

The object 104 can include a mammal, an animal, a human, a pet, or any other suitable object capable of living or being present in the area 100, whether male or female. The mammal may include the animal, the human, the pet, or any other suitable animal. The animal may include a zoo animal, the human, the pet, or any other suitable animal. The human may be a baby, a toddler, a preschooler, a grade schooler, a teenager, a young adult, an adult, or an elderly person. The pet may include a dog, a cat, a bunny, a bird, or another suitable pet. Note that the object may not live in the area 100, but may be present in the area 100 as well. For example, this may apply to visitors, workers, maintenance personnel, cleaning personnel, medical personnel, emergency personnel, or other objects (e.g., mammals, animals, humans, pets) that may be present or movable within the area, whether animate or inanimate, whether living or not living in the area 100.

The area 100 is embodied as a residence (e.g., a studio apartment) of the object 104. As shown in FIG. 1 (top view), the area 100 is defined by the wall 132, the door 134, and the window 136 to be shaped as a rectangle. However, note that the area 100 can be defined by the wall 132, the door 134, or the window 136 to be shaped as another suitable shape (e.g., a square, an oval, a polygon, an open-shape, a closed-shape, a teardrop, a corner-less area). The wall 132 includes a stud (e.g., wood, metal) frame having a drywall/siding configuration (e.g., an external wall) or a drywall/drywall configuration (e.g., an internal wall). However, this configuration is not required and the wall 132 may be configured differently (e.g., a brick wall, a fabric wall, a glass wall, a plastic wall, a metal wall, a lattice, a barred wall, a cage wall, a log wall). Note that the door 134 or the window 136 may be omitted.

As shown in FIG. 1, the area 100 contains the bathroom 118 defined by the wall 128, the wall 132, and the door 138 to be shaped as a rectangle. However, note that the bathroom 118 can be defined by the wall 128, the wall 132, or the door 138 to be shaped as another suitable shape (e.g., a square, an oval, a polygon, an open-shape, a closed-shape, a teardrop, a corner-less area). The wall 128 includes a stud frame having a drywall/siding configuration (external wall) or a drywall/drywall configuration (internal wall). However, this configuration is not required and the wall 128 may be configured differently (e.g., a brick wall, a fabric wall, a glass wall, a plastic wall, a metal wall, a lattice, a barred wall, a cage wall, a log wall). Note that the door 138 may be omitted.

Although the area 100 includes the bathroom 118, this is not required. For example, the bathroom 118 may be omitted or the area 100 may be the bathroom 118. Similarly, although the area 100 is embodied as the residence of the object 104, with the residence having the bathroom 118, a living area, and a kitchen area, this is not required. As such, the area 100 can be embodied as any suitable residential area for the object 104 to live therein. For example, the area 100 can be embodied as a living room or a living area, a dining room or a dining area, a bedroom or a sleep area, a bathroom or a bathroom area, a shower room or a shower area, a play room or a play area, a home office or a home office area, a basement or a basement area, a garage or a garage area, a shed or a shed area, an attic or an attic area, an exercise room or an exercise area, a mud room or a mud area, a closer or a closet area, or any other suitable residential room or area, although non-residential area may be used as well. Likewise, although the area 100 is shown as the residence of the object 104, this is not required. As such, the area 100 can be embodied in various ways. For example, the area 100 can be embodied in or be a building, a condominium, a detached home, an attached home, a warehouse, a lobby, an office space, a cubicle, a corridor, a vestibule, an hotel, a tent, a cabin, a cage, a medical facility, a nursing home, a hospice, an assisted living facility, a hospital, a passenger area in a vehicle, a driver area in a vehicle, a control area of a vehicle, an elevator, an airplane or helicopter cockpit, an airplane or helicopter cabin, a boat room, a boat cockpit or cabin, or any other suitable area.

The area 100 and the bathroom 118 has various objects of daily living distributed therein, whether fixtures (e.g., an electrical fixture, a plumbing fixture) or movable (e.g., a floor lamp, a vase). These objects include the stand 106, the sofa 108, the table 110, the chair 112, the oven 114, the refrigerator 116, the bathroom 118, the toilet 120, the tub 122, and the sink 124, any or all of which may be omitted from the area 100. Note that how these objects of daily living are distributed in the area 100 is illustrative and other layouts of these objects of daily living are possible.

The area 100 includes a floor, a ceiling, and a corner, although the ceiling or the corner can be omitted. Near the corner, there is the stand 106 (e.g., a table, a coffee table, a night table, a chair, a shelf) on which the device 102 is resting, disposed, or positioned (e.g., stationed, fixed). However, note that the stand 106 may or may not be omitted and the device 102 can be resting on or attached to (e.g., fastened, mated, adhered) the floor, attached to (e.g., fastened, mated, adhered) or suspended (e.g., via a cable or a chain) from the ceiling, or attached to (e.g., fastened, mated, adhered) or hung on (e.g., fastened, mated, adhered) the wall 132 or the wall 128.

The device 102 includes a processor (e.g., a controller, an edge processor, a single core processor, a multicore processor, a system-on-chip, a graphics processing unit, a hardware accelerator, a neural network accelerator, a machine learning accelerator) and a radar (e.g., a time-of-flight radar, a Doppler radar), where the processor is coupled (e.g., electrically, logically, mechanically) to the radar to control the radar (e.g., receive tracking data). For example, the processor may include a controller and a hardware accelerator. For example, the processor may enable local or edge computing to enhance processing speed or provide data privacy or data security. The radar may have a set of components shown in FIG. 7 and a field of view 130. For example, the field of view can be or include about 120 degrees horizontal (or less or more) and about 90 degrees vertical (or less or more). Likewise, for example, the radar may be as disclosed in U.S. Pat. No. 9,019,150, which is incorporated by reference herein at least for all radar purposes.

Although the device 102 is shown in FIGS. 1-9 to have a housing (e.g., a container, an enclosure, a box, a cube, a cuboid, a pyramid, a cone, a sphere, an ovoid, a television unit, a soundbar, a speaker, a bookend, a flowerpot, a planter pot, a vase, a furniture item, a table, a chair, a sofa, a bed, a crib, a shelf, a bookcase, a television stand, a house appliance, a dishwasher, a refrigerator, an oven, a stovetop, a toy, an exercise equipment item, a treadmill, a rowing machine, a musical instrument, a fixture) hosting (e.g., internally, externally) the processor and the radar, this is optional and the housing may be omitted or vary. For example, some form factors of the housing are shown in FIG. 9. Likewise, for example, one or both of the processor and the radar can be not housed at all or can be housed in different housings (e.g., the processor in a first housing and the radar in a second housing), whether those different housings are attached to each other, detached from each other, spaced apart from each other, opposing each other, or any other suitable configuration, whether those housings are structurally or functionally identical or non-identical to each other.

As shown in FIG. 1, the device 102 includes a power line (e.g., a wire, a cord, a cable) via which the processor and the radar are powered. If the device 102 includes other components, as disclosed herein, then those components may also be powered via the power line. As such, the power line includes an electrical plug and the device 102 is positioned within the area 100 near the electrical outlet 126 for the electrical plug to be sufficiently elongated or flexible to be plugged into the electrical outlet 126 and thereby power the device 102. The electrical outlet 126 can be 110 volts, 220 volts, or any other voltage suitable for operating the device 102. However, the power line can be omitted or be another power option if the device 102 includes a battery, which may be rechargeable, that is sufficiently energized to power the processor, the radar, and any other components of the device 102, if necessary, for a preset period of time (e.g., 30 minutes, 90 minutes, 120 minutes, 24 hours, 72 hours), as disclosed herein.

The processor may activate the radar to operate within the area 100 such that the radar operates within the area 100 and tracks the object 104 living in the area 100 when the object 104 is positioned within the field of view 130 within the area 100. The radar generates a set of data based on tracking the object 104 living in the area 100 when the object 104 is positioned within the field of view 130 within the area 100 and sends the set of data to the processor such that the processor determines whether the object 104 is experiencing an event (e.g., a medical emergency, a fall, a death, a heart attack, a seizure) within the area 100 based on the set of data and takes an action (e.g., initiates a communication with a remote phone unit or a server) responsive to the event determined to be occurring within the area 100. For example, the processor may distinguish between a fast fall and a slow fall, each associated with its own signature for medical purposes. For example, the event may be a medical event, which may be a diagnosis estimate or a diagnosis forecast. For example, the action may be triggered by thresholds based on one or more criteria about the object 104 or its environment being tracked by the radar. For example, the action may be (a) the device 102 calling (e.g., via its SIM module) a preset phone number (e.g., a family member, a caretaker, a social worker, a medical professional, a nurse, a personal doctor, a medical facility, an emergency service), (b) sending (e.g., via its Wi-Fi interface) a message to a server remote from the area 100, the device 102, and the object 104, (c) performing a set of escalation actions preprogrammed in advance (e.g., sounding an "are you okay message" and calling a preset phone number if no response from the object 104), or (d) other suitable actions. As noted above, the object 104 does not need to be living in the area 100 to be in the field of view 130. As such, the object 104 can be present in the area 100 (e.g., for a relatively extended or temporary period of time whether on a repeating pattern or a single visit) and be in the field of view 130.

The radar may operate in a Ku-band inclusively between about 12 GHz and about 18 GHz, a K-band inclusively between about 18 GHz and about 27 GHz, or a Ka-band inclusively between about 26.5 GHz and about 40 GHz, while complying with local radiation laws (e.g., as regulated by Federal Communications Commission) and without radiationally interfering with other objects in its operational vicinity (e.g., stationary or mobile medical equipment, wearable medical equipment, pacemakers, insulin pumps, infusion pumps, microwave ovens, televisions, radios, Wi-Fi, cellular phones, printers, networking equipment). When the radar operates in at least two of such bands, the radar may be a single radar unit operating in at least two of such bands or the radar may have at least two of radar units respectfully dedicated to at least two of such bands. For example, the radar may operate in the Ku-band inclusively between about 12 GHz and about 18 GHz. For example, the radar may operate in the K-band inclusively between about 18 GHz and about 27 GHz. For example, the radar may operate in the Ka-band inclusively between about 26.5 GHz and about 40 GHz. For example, the radar may operate in at least two of the Ku-band inclusively between about 12 GHz and about 18 GHz, the K-band inclusively between about 18 GHz and about 27 GHz, or the Ka-band inclusively between about 26.5 GHz and about 40 GHz, whether serially (e.g., the radar is switched between at least two of these bands to enhance resolution of the object 104 or the area 100 or its contents or manage power or heat dissipation), such as when requested by the processor based on the processor determining whether various criteria, signatures, or thresholds have or have not been satisfied (e.g., to enhance resolution of the object 104 or the area 100 or its contents or manage power or heat dissipation), as disclosed herein, or in parallel (e.g., the radar simultaneously operates in at least two of these bands without interference with itself to supplement or validate or confirm itself), such as when requested by the processor based on the processor determining whether various criteria, signatures, or thresholds have or have not been satisfied (e.g., to enhance resolution of the object 104 or the area 100 or its contents or manage power or heat dissipation), as disclosed herein. For example, the radar may operate in the Ku-band inclusively between about 12 GHz and about 18 GHz, the K-band inclusively between about 18 GHz and about 27 GHz, and the Ka-band inclusively between about 26.5 GHz and about 40 GHz, whether serially (e.g., the radar is switched between these bands to enhance resolution of the object 104 or the area 100 or its contents or manage power or heat dissipation), such as when requested by the processor based on the processor determining whether various criteria, signatures, or thresholds have or have not been satisfied (e.g., to enhance resolution of the object 104 or the area 100 or its contents or manage power or heat dissipation), as disclosed herein or in parallel (e.g., the radar simultaneously operates in at least two of these bands without interference with itself to supplement or validate or confirm itself), such as when requested by the processor based on the processor determining whether various criteria, signatures, or thresholds have or have not been satisfied (e.g., to enhance resolution of the object 104 or the area 100 or its contents or manage power or heat dissipation), as disclosed herein. For example, the radar may switch frequencies within the Ku-band inclusively between about 12 GHz and about 18 GHz, such as when requested by the processor based on the processor determining whether various criteria, signatures, or thresholds have or have not been satisfied (e.g., to enhance resolution of the object 104 or the area 100 or its contents or manage power or heat dissipation), as disclosed herein. For example, the radar may switch frequencies within the K-band inclusively between about 18 GHz and about 27 GHz, such as when requested by the processor based on the processor determining whether various criteria, signatures, or thresholds have or have not been satisfied (e.g., to enhance resolution of the object 104 or the area 100 or its contents or manage power or heat dissipation), as disclosed herein. For example, the radar may switch frequencies within the Ka-band inclusively between about 26.5 GHz and about 40 GHz, such as when requested by the processor based on the processor determining whether various criteria, signatures, or thresholds have or have not been satisfied (e.g., to enhance resolution of the object 104 or the area 100 or its contents or manage power or heat dissipation), as disclosed herein. These bands have been unexpectedly found to be technologically beneficial for various reasons, as disclosed herein.

With respect to the Ku-band, the radar operates within the area 100 at a radio frequency inclusively between about 12 GHz and about 18 GHz (wavelength between about 24.00 millimeters and about 16.65 millimeters) or the radar may switch frequencies within the Ku-band inclusively between about 12 GHz and about 18 GHz, such as when requested by the processor based on the processor determining whether various criteria, signatures, or thresholds have or have not been satisfied (e.g., to enhance resolution of the object 104 or the area 100 or its contents or manage power or heat dissipation), as disclosed herein. This band has been unexpectedly found to be technologically beneficial for penetrating walls/objects in the field of view 130 better than higher frequencies—and thus enabling the radar to have further range, which is useful for location tracking of the object 104 within the area 100 and pose detection of the object 104 within the area 100.

With respect to the K-band, the radar operates within the area 100 at a radio frequency band inclusively between about 18 GHz and about 27 GHz (wavelength between about 16.65 millimeters and about 11.10 millimeters) or the radar may switch frequencies within the K-band inclusively between about 18 GHz and about 27 GHz, such as when requested by the processor based on the processor determining whether various criteria, signatures, or thresholds have or have not been satisfied (e.g., to enhance resolution of the object 104 or the area 100 or its contents or manage power or heat dissipation), as disclosed herein. This band has been unexpectedly found to be technologically beneficial for corresponding to a peak in an absorption spectrum of water. This is important because, in certain situations, a conventional radar may not be set up to operate at a frequency above 22 GHz, as that frequency may be easily absorbed by water. Therefore, the conventional radar is normally desired to have its signals penetrating a water-vapor to arrive at another more reflective (e.g., metal) target. As such, if the object 104 is a mammal, such as a human, who may have water content of up to 60%, then the radar tracking the object 104 in the field of view 130 may produce a large measurable change in an amount of reflected signal within the area 100, which improves accuracy or precision of the radar operating within the area 100 and tracking the object 104 in the field of view 130 within the area 100. Within the K-band, a radio frequency range inclusively between about 23 GHz and about 25 GHz, and especially about 24 GHz, has been unexpectedly beneficial, as explained above.

With respect to the Ka-band, the radar operates within the area 100 within a radio frequency band inclusively between about 26.5 GHz and about 40 GHz (wavelength between about 11.31 millimeters and about 7.49 mm millimeters) or the radar may switch frequencies within the Ka-band inclusively between about 26.5 GHz and about 40 GHz, such as when requested by the processor based on the processor determining whether various criteria, signatures, or thresholds have or have not been satisfied (e.g., to enhance resolution of the object 104 or the area 100 or its contents or manage power or heat dissipation), as disclosed herein. This band has been unexpectedly found to be technologically beneficial for making it easier to detect a vital sign (e.g., a heart rate, a respiratory rate) when the object 104 is a mammal, such as a human, is positioned in the field of view 130. Since the object 104 may repeatedly deflect due to oxygen inhaling/exhaling or blood pulsation in the field of view 130, this state of being makes a larger percentage change of a carrier frequency's wavelength as detected by the processor.

The radar may switch modalities between a Doppler mode (or another radar modality) and a time-of-flight mode (or another radar modality) when requested by the processor based on the processor determining whether various criteria, signatures, or thresholds have or have not been satisfied (e.g., to enhance resolution of the object 104 or the area 100 or its contents or manage power or heat dissipation), as disclosed herein. Note that such switching may or may not operate serially or in parallel, may or may not interfere with each other, or may or may not be together with frequency switching or band switching, whether the radar is operating in the Ku-band, the K-band, or the Ka-band or other bands, as disclosed herein. For example, the radar may have a first radar unit operating in the Doppler mode and a second radar unit operating in the time-of-flight mode, where the processor requests that the first radar unit operate in the Doppler mode and then switch to the second radar unit to operate in the time-of-flight mode, or vice versa, based on the processor determining whether various criteria, signatures, or thresholds have or have not been satisfied (e.g., to enhance resolution of the object 104 or the area 100 or its contents or manage power or heat dissipation), as disclosed herein, although parallel or serial radar mode operation is possible. Note that the first radar unit and the second radar unit can be hosted (e.g., internally, externally) by a common housing or each one can have its own housing, which may be spaced apart (e.g., within about 5, 4, 3, 2, 1 feet or meters) from each other, as disclosed herein. Likewise, for example, the radar may be operating in the Doppler mode or in the time-of-flight mode, where the processor requests that the radar operate in the Doppler mode and then switch to the time-of-flight mode, or vice versa, based on the processor determining whether various criteria, signatures, or thresholds have or have not been satisfied (e.g., to enhance resolution of the object 104 or the area 100 or its contents or manage power or heat dissipation), as disclosed herein, although parallel or serial radar mode operation is possible.

The radar has been designed by experience with many prototypes, which include operation at about 5 GHz (and within that respective band), about 24 GHz (and within that respective band), about 60 GHz (and within that respective band), and other operating frequencies (all of which and their respective bands work but some work better than others for some use cases), and expertise with radar, signal processing, and artificial intelligence. For example, with respect to about 5 GHz (and within that respective band) or about 60 GHz (and within that respective band), the radar may operate at those frequencies or within its corresponding bands or switch frequencies therein or switch bands with the Ku-band or the K-band or the Ka-band or other bands disclosed herein. In some embodiments, some design parameters relate to a field of view (left and right limits of what the radar can see). For example, there can be a field of view of about 120 degrees horizontal (or lower or higher), about 90 degrees vertical (or lower or higher), or other fields of view. In some embodiments, some design parameters relate to a resolution (granularity with which the radar distinguishes details within its field of view). The resolution may be implemented via voxels (3D pixels) with about 15 degrees 'width', about 15 degrees 'height', and about 25 centimeters depth, useful for location and fall detection, although forms of resolutions are possible, whether each individually higher or lower. The resolution may be in millimeters within those voxels, which may be useful for heart rate, respiratory rate measurements, or other vital signs. In some embodiments, some design parameters relate to penetration (a balance between the radar's ability to penetrate common objects (e.g. walls, furniture)—versus reflection from objects being monitored (e.g., humans)). For example, some embodiments enable the penetration at about 20 meters through two layers of US standard studded drywall or drywall/siding, with good or sufficient reflection off human targets. Note that this distance is illustrative and can increase or decrease based on other parameters (e.g., supplemental data sources, supplemental radar, types of materials used in manufacturing of walls or home appliances or furniture, height of radar relative to ground floor or physical area or monitored floor or physical area, power limits set by governmental authorities). In some embodiments, some design parameters relate to transmit power (if the field of view defines at least some directions for the radar to scan, the transmit power affects how far the radar can see).

As explained above, the radar operating at the K-band inclusively between about 18 GHz and about 27 GHz (wavelength between about 16.65 millimeters and about 11.10 millimeters) and especially within the K-band inclusively between about 23 GHz and about 25 GHz, and more especially at about 24 GHz, has been unexpectedly beneficial due to a good balance between signal penetration, tracking distance, and human detection, while being compliant at a regulated power limit, which itself is set to be well within human safety parameters across a very wide range of applications or use cases, as disclosed herein. By operating the radar in the K-band inclusively between about 18 GHz and about 27 GHz (wavelength between about 16.65 millimeters and about 11.10 millimeters) and especially within the K-band inclusively between about 23 GHz and about 25 GHz, and more especially at about 24 GHz, the radar can further tune the field of view and the resolution by altering some properties of some antenna arrays, or by adding additional radar subsystem boards as may be required for future applications. For example, this form of operation may be a relatively high frequency that allows accurate range measurements, yet enables some antennas to be small and overall antenna arrays are compact, enabling integration into a variety of form factors, as disclosed herein.

Material penetration properties of the radar operating inclusively between about 18 GHz and about 27 GHz (wavelength between about 16.65 millimeters and about 11.10 millimeters) and especially within the K-band inclusively between about 23 GHz and about 25 GHz, and more especially at about 24 GHz, are much better for tracking indoors (e.g., within the area 100) than operating at about 60 GHz or about 76-78 GHz, although operating at about 60 GHz (or within its corresponding band or switch frequencies therein or switch bands with the Ku-band or the K-band or the Ka-band or other bands disclosed herein) or about 76-78 GHz (or within its corresponding band or switch frequencies therein or switch bands with the Ku-band or the K-band or the Ka-band or other bands disclosed herein) may be sufficient for some use cases indoors (e.g., within the area 100), as disclosed herein. Specifically, the radar operating inclusively between about 18 GHz and about 27 GHz (wavelength between about 16.65 millimeters and about 11.10 millimeters) and especially within the K-band inclusively between about 23 GHz and about 25 GHz, and more especially at about 24 GHz, can operate through a few layers of standard wall construction and see through various types of clothing. For example, some radars above 60 GHz may be limited to in-room operation because walls are effectively opaque or may be strongly affected by clothing, which produces noise. For example, the radar operating at about 60 GHz could detect heart rate and respiratory rate for a relatively still object 104, standing within about seven meters in front of the radar. However, some embodiments of the radar operating at about 60 GHz do not adequately penetrate solid objects including clothing nor a human body. Those measurements, therefore, can become noisy if the object 104 moved and their clothing, if any, fluttered. In contrast, the radar operating inclusively between about 18 GHz and about 27 GHz (wavelength between about 16.65 millimeters and about 11.10 millimeters) and especially within the K-band inclusively between about 23 GHz and about 25 GHz, and more especially at about 24 GHz, can penetrate a human body, which helps minimize motion-related noise. Furthermore, when the radar operates inclusively between about 18 GHz and about 27 GHz (wavelength between about 16.65 millimeters and about 11.10 millimeters) and especially within the K-band inclusively between about 23 GHz and about 25 GHz, and more especially at about 24 GHz, and based on voxel-based tracking, the processor is able to discard, remove, delete, or ignore any or certain voxels that do not intersect the object 104, such as a human body, or alternately, to simultaneously measure vitals for multiple objects 104, such as people, in the area 100. For example, when using voxel-based tracking, the processor may receive the set of data from the radar; access a set of voxels formed based on the set of data; discard, remove, delete, or ignore a first subset of voxels from the set of voxels based on the first subset of voxels not representing the object 104 living in the area 100 (when the first subset represents empty space) such that a second subset of voxels from the set of voxels is identified; and take the action, as disclosed herein, responsive to the event determined to be occurring within the defined area based on the second subset of voxels. Therefore, this form of voxel-filtering enables more processing efficiency. Additionally, the radar operating inclusively between about 18 GHz and about 27 GHz (wavelength between about 16.65 millimeters and about 11.10 millimeters) and especially within the K-band inclusively between about 23 GHz and about 25 GHz, and more especially at about 24 GHz, enables millimeter level resolution within a voxel to see a motion of an individual's tissue and skin as a function of their heartbeat and breathing.

When the device 102 is provided to a user, who may (e.g., DIY) or may not (e.g., an agent, child, or caretaker on behalf of a parent or care recipient) be the object 104, the user may be instructed regarding the device 102 (e.g., configuration and use). For example, the user may be the object (e.g., DIY) or the user may not be the object (e.g., an agent, child, or caretaker on behalf of a parent or care recipient). The device 102 may be provided to the user in various ways. For example, the device 102 may be mailed (e.g., US mail), couriered (e.g., FedEx), shipped (e.g., in a package), sent, handed, delivered, present or installed in an area, a dwelling, or vehicle, or otherwise suitably availed to the user. The user may be instructed in various ways. For example, the user may be instructed via a medium, such as a written, drawn, or printed manual, a computer file (e.g., a portable document format file, a presentation file, a word processing file, an image file, a video file, an audio file), a website, a mobile application, a vocal or pictorial guide, an auditory or visual wizard, a call center, or otherwise suitably instructed regarding the device (e.g., how to use). The user may be instructed on how and where to position the device 102 within the area 100 having the object 104 living therein, although the object 104 may be present therein (e.g., relatively temporarily). The user may be instructed on how to power, turn on, and activate the radar within the area 100. If initial configuration or setup may be needed, then the user may be instructed accordingly.

Once the radar is set up and activated, then the radar may operate within the area 100 such that the radar tracks the object 104 living (or positioned) in the area 100, generates a set of data based on tracking the object 104 living (or positioned) in the area 100, and sends the set of data to the processor such that the processor determines (e.g., individually or in combination with other knowledge, forecasts, estimates, inferences, or data from data sources about the object 104 or the area 100) whether an action should be taken based on the set of data and takes the action based on the set of data. For example, the processor may determine whether the object 104 is experiencing an event (e.g., a medical emergency, a fall, a death, a heart attack, a seizure, a diagnosis prediction, a diagnosis estimate, a diagnosis forecast) within the area 100 based on the set of data and takes the action (e.g., initiates a communication with a remote phone unit or a remote server) responsive to the event determined to be occurring within the area 100. For example, the processor may determine whether the object 104 is experiencing the event based on forming a signature of the object based on the set of data, which may be over a period of time, comparing the signature against a set of signature templates corresponding to a set of events (e.g., a medical emergency, a fall, a death, a heart attack, a seizure, a diagnosis prediction, a diagnosis forecast), and then determining whether a match threshold between the signature and the set of signature templates has or has not been satisfied. For example, the match threshold may or may not be satisfied to estimate that the object 104 may be deteriorating in health (e.g., activity of daily living, locomotion, speed of movement, reaction time).

The event can be related to an activity of daily living (e.g., eating, drinking, sleeping, washing, bathing, toileting, reading, sitting, exercising, laundering, cooking, cleaning) of the object 104 within the area 100. For example, the event may be identifying that the object 104 is sufficiently or insufficiently performing the activity of daily living or that there is a decrease or increase or maintenance in a number or a frequency or a quality of the activity of daily living. Likewise, the event may be related to a fall of the object 104 within the area 100. Similarly, the event may be related to the object 104 remaining still for a preset period of time within the area 100 (e.g., dying, dead, paralyzed, injured, unconscious, sleeping). Further, the event may be related to the object 104 being absent from the area 100 for a preset period of time (e.g., lost, disappeared, injured, dying, dead, unconscious, seizing, occluded). Also, the event may be related to the object 104 not being tracked within the area 100 for a preset period of time while the object 104 is within the area 100 (e.g., dead, paralyzed, injured, unconscious, sleeping within an occluded area or a coverage gap).

Note that the processor is not required to determine whether the event is being experienced by the object 104 within the area 100. As such, whether additionally or alternatively, the processor may determine, which may be independent of, agnostic to, or without the event, whether the action should be taken based on the set of data and takes the action based on the set of data, which may be independent of or without the event. For example, the processor may determine that no event is being experienced by the object 104 within the area 100 or that a frequency change within a band (e.g., the Ku-band, the K-band, the Ka-band) may be needed (e.g., enhance resolution of the object 104 or the area 100 or its contents or manage power or heat dissipation) independent of or agnostic to the event or that a band change (e.g., between at least two of the Ku-band, the K-band, or the Ka-band) may be needed (e.g., enhance resolution of the object 104 or the area 100 or its contents or manage power or heat dissipation) independent of or agnostic to the event or that the set of data may be needed to be validated or confirmed by another data source (e.g., a set of microphones, a camera, a sensor) independent of or agnostic to the event, as disclosed herein.

As explained herein, the device 102 may be embodied in or as a wide variety of everyday home objects (e.g. housings, frames, bases), such as TVs, dumb speakers and smart speakers, bookends, flowerpots, planter pots, vases (or other containers), furniture (e.g., tables, chairs, couches, wall-hung or tabletop or shelf-top picture frames, bookcases, shelves, dressers, beds, cabinets, armoires), house appliances (e.g., dishwasher, oven/stovetop, microwave, refrigerator, washing machine, dryer). Such implementations provide a clear technological enhancement over various sensing capabilities of current offerings, as disclosed herein. However, note that additional or alternative non-home or non-residence use cases are possible. These may include in-car or in-vehicle (e.g., bus, boat, airplane, railcar) applications for measuring eye movements, facial expressions, mouth movements, head movements, joint movements, heart rate, respiratory rate, or other vitals, while people drive or are transported to and from work or other destinations and others as people live, work, or play. For example, when the device 102 is installed or included in a vehicle (e.g., an automobile, a truck, a bus, a cockpit), then the radar, as disclosed herein, may track (e.g., by facial, eye, mouth, head, or joint movements or expressions) whether an operator of the vehicle (e.g., a driver) or any passenger of the vehicle is tired, drowsy, falling asleep, unconscious, dead, having a seizure, or drunk and then take appropriate action as programmed (e.g., do not start the vehicle, decelerate or stop the vehicle if safe, notify an emergency phone number or radio contact from the vehicle, notify a preset phone number or radio contact from the vehicle, send a geolocation from the vehicle to a remote server, open windows of the vehicle, sound horn of the vehicle or security alarm of the vehicle, open doors if safe or not too cold or the vehicle is not moving, post on social media from the vehicle). Likewise, when the device 102 is installed or included in a vehicle (e.g., a passenger vehicle, an automobile, a van, a minivan, a sports utility vehicle), then the radar, as disclosed herein, may track (e.g., by facial, head, or joint movements or expressions) whether a baby (or an infant, a toddler, a disabled person, a frail person, or an elderly person) is present or left in the vehicle (e.g., in a car seat) when nobody is tracked in the vehicle other than the baby (or the infant, the toddler, the disabled person, the frail person, or the elderly person) and then take appropriate action as programmed (e.g., start the vehicle, turn on air conditioner or heat or climate control of the vehicle, notify an emergency phone number from the vehicle, notify a preset phone number from the vehicle, send a geolocation from the vehicle to a remote server, open windows of the vehicle, sound horn of the vehicle or security alarm of the vehicle, open doors of the vehicle if safe or not too cold or the vehicle is not moving, post on social media from the vehicle). Any tracking of these situations may be supplemented by data from other input devices (e.g., microphones, cameras, sensors), as disclosed herein, and powered by an onboard battery.

As explained herein, the radar operating at the K-band inclusively between about 18 GHz and about 27 GHz (wavelength between about 16.65 millimeters and about 11.10 millimeters) and especially within the K-band inclusively between about 23 GHz and about 25 GHz, and more especially at about 24 GHz, may be a time-of-flight radar feeding its set of data to the processor for the processor to convert into a set of voxels to simulate the object 104, which may including simulating the area 100. The radar may switch bands (e.g., between the Ku-band, the K-band, or the Ka-band) or frequencies (e.g., within the Ku-band, the K-band, or the Ka-band) to enhance resolution of the set of voxels is incomplete, imprecise, inaccurate, or does or does not satisfy a preset resolution threshold, as disclosed herein. As such, the radar may track a location, a body position, or a vital sign of the object 104 (e.g., humans, elderly, disabled, infirm) in its field of view 130—at home; in a hospital or nursing home or rehab facility; in senior living facilities; in care homes and shelters, or other suitable medical or non-medical facilities, whether above ground or below ground, whether indoors or outdoors.

As further explained herein, a set of microphones included in the device 102 and controlled by the processor may optionally provide high-quality 3D audio mapping to pin-point or localize sound sources as well as may optionally provide a two-way audio functionality. For example, the set of microphones may feed the processor with audio data (and other sensors with their respective data) to enable a flexible computing platform that combines processing with hardware-accelerated artificial intelligence (AI) at edge, i.e., edge computing. As further explained herein, the device 102 may include a single or variety of communication options (e.g., wired, wireless, waveguide) to allow the device 102 to serve as a hub for other devices, and to transfer data, alerts, and critical information to and from a virtual computing instance (e.g., a server, an application, a database) running in a cloud computing service (e.g., Amazon Web Services, Google Cloud) or to a phone, whether in a wired, wireless, or waveguide manner. To maximize efficiency and security, the device 102 may be securely and periodically updated over-the-air to support improvements and additions to various processor/radar algorithms, as well as an optional evolving ecosystem of devices and services.

As explained herein, the radar sends the set of data (e.g., raw data) to the processor (e.g., an edge processor) for the processor to process with its onboard algorithms to reconstruct a high-resolution, 3D information (e.g., voxel information) about the area 100 within the field of view 130. The device 102 then applies various techniques to identify or infer various information about the object 104. For example, when the object 104 is a human, then the processor may identify a body position (e.g., erect, reclined, supine, prone, recumbent) of the object 104 or an activity of daily living (e.g., sitting, standing, walking, fallen, sleeping, eating, exercising, showering, bathing, cooking) of the object 104. The processor may combine this information with data from other sensing subsystems (e.g., audio, vision, temperature, motion, distance, proximity, moisture) and additional data sources when available—ranging from fitness apps (e.g., tracking the object 104) to social media (e.g., profile of the object 104) to electronic health records (e.g., of the object 104)—to know (e.g., deterministically) rather than guess (e.g., probabilistically) how people are doing so that the device 102 may enable their safety, wellbeing, and supported self-care, while minimizing false alarms or missed signs of rising risk.

As explained herein, the device 102 benefits from a virtuous cycle of growing datasets. These datasets drive quality improvements, which increase user value, which results in more adoption, which produces more data. Although some services may have large collections of voice data from home, in certain embodiments, the device 102 has a multi-sensor ambient sensing platform and the cloud computing service provides valuable context; considered cohesively, the device 102 has or generates a uniquely rich dataset that grows over time. For example, the device 102 may be further developed/enhanced (e.g., by over-the-air firmware updates) by continuous in-field A-B testing, producing improvements in sensor processing, health monitoring, user experience, all based on continuously improving the AI to catalyze additional capabilities, use cases, and resulting offerings over time. For example, the device 102 may have a memory (e.g., a persistent memory, a flash memory) accessible to the processor, where the memory stores an AI model (e.g., based on a convolution neural network, a recurrent neural network, a reinforcement algorithm) trained to determine whether the object 104 satisfies or does not satisfy various criteria, signatures, or thresholds, which may relate to health, safety, or security of the object 102 within the area 100. As such, when the object 104 is a human, the processor may access the AI model to analyze long temporal baselines to observe early indicators of changes in the human's safety, wellbeing, and health. Therefore, as the device 104 is used to track the object 104 over time, there should be improved monitoring as well based on the AI model understanding the object 104 better.

As explained herein, there are many illustrative use cases for the device 102. For example, when the object 104 is a human, observing (e.g., by the processor via the radar) everyday biometrics, motion, and activities of daily living (and the processor acting based on those) can help detect a potential emergence of health and safety risk proactively, well in advance of episodic physical examination, laboratory, and diagnostic tests, sometimes in advance of any awareness of any deterioration in health. Through observation (e.g., by the processor via the radar) and analysis (e.g., by the processor via the radar) of this pattern of everyday activities, such as eating, drinking, sleeping, exercising, laundering, bathing, showering, toileting, socializing, dressing, and micro-behaviors, such as taking medications, a digital picture of the person's health and wellbeing emerges (which the processor can act based on). In addition, observing (e.g., by the processor via the radar) and analyzing (e.g., by the processor) movement, time spent in bed, and frequency of toileting use and then acting based on those (e.g., electronically notifying an individual, a family member, or a physician by a sound prompt, a warning message, or a mobile app) can indicate signs of disease which an individual, family member, or even their clinician may not readily notice. Therefore, not only can the device 102 raise awareness of these undetected disease states, but the device 102 can also help to identify (e.g., by the processor) deterioration of mental or physical function and monitor (e.g., by the processor) chronic conditions the human already experiences for signs of worsening (and the processor acting based on those). The device 102 enables detection (e.g., by the processor) of such signs of risks to people's safety, wellbeing, and health well before these result in higher acuity, and ambulance rides, emergency room admissions, and hospitalizations. Therefore, a desired end result is reduced hardship for people supported by the device 102; reduced cost due to proactive, predictive intervention; and more efficient utilization of precious healthcare resources.

One use case of the device 102 is to detect falls of the object 104 via the processor. For example, if the object 104 is an elderly human, then the fall may be dangerous to health and safety thereof. Although falls are common, but this generic term hides significant variation and subtlety in the event suffered by the object 104. Fall features or subtleties, such as location, context, direction, speed, orientation, angling, or others, as tracked by the radar and communicated to the processor, may provide clues to the processor for their underlying causes, and these details have a great degree of clinical significance. Unfortunately, many who have fallen suffer injuries that may complicate efforts to know what actually happened, and this frequently poses a diagnostic challenge to physicians. Falls' speed or direction, as determined by the processor based on the set of data from the radar, may have impacts on a likelihood of head injury, fracture, and recovery. As such, the processor may consider or detect various fall factors based on the set of data from the radar. These factors may include a location—which room, location within room, type, and intensity. These factors may include a context—while showering versus entering a room at a threshold. These factors may include a result—immobile, regaining footing, or non-standing movement. These factors may include a type—roll/fall from bed, drop from standing, or slump from chair. These factors may include a direction—may correlate to a simple stumble or a brain-affecting event. These factors may include a rate—speed increases injury, trajectory may indicate trip or drop. These factors may include a disability—asymmetric movement may indicate fracture. Therefore, some of these factors may have implications for degree of injury or the presence of underlying conditions.

One use case of the device 102 is to detect functional limitations of the object 104 via the processor. For example, if the object 104 is an elderly human, then the functional limitation may be dangerous to health and safety thereof. Frail humans may undergo various changes in mental and physical function over time (e.g., as tracked by the radar and detected by the processor) prior to becoming impaired to a degree (e.g., as detected by the processor) that care is sought or others notice this, whether these are cognitive or physical limitations. Detectable evidence of reduced mental function (e.g., as tracked by the radar and detected by the processor) may include changes in self-care patterns (e.g., as tracked by the radar and detected by the processor), or ability to remain asleep (e.g., as tracked by the radar and detected by the processor). Evidence of reduced physical function (e.g., as tracked by the radar and detected by the processor) includes reduction in overall physical activity (e.g., as tracked by the radar and detected by the processor), walking speed (e.g., as tracked by the radar and detected by the processor), or evidence of stumbling (e.g., as tracked by the radar and detected by the processor).

One use case of the device 102 is to detect changes in activities of daily living via the processor. For example, if the object 104 is an elderly human, then these changes may be dangerous to health and safety thereof. Older humans are regularly assessed (e.g., as tracked by the radar and detected by the processor) for their capability to perform their activities of daily living, and changes to these (e.g., as tracked by the radar and detected by the processor) are part of an aging process that may correlate with future problems in self-care, coping, and independence. Along with disease states (e.g., as tracked by the radar and detected by the processor), these changes may be an important part of a Frailty Index (e.g., as tracked by the processor), a proxy for vulnerability to poor outcomes. Therefore, the device 102 can detect (e.g., as tracked by the radar and detected by the processor) a human's engagement in several key activities of daily living, including sleeping, eating, drinking, toileting, socializing, or others. For example, based on the set of data received from the radar, the processor may track sleeping—detect sleep interruptions, schedule changes, time to restful sleep, or early awakening. For example, based on the set of data received from the radar, the processor may track eating or drinking—timing, frequency, prep duration, eating or drinking duration, or whether or not cooking. For example, based on the set of data received from the radar, the processor may track toileting—timing and frequency of toilet use. For example, based on the set of data received from the radar, the processor may track socializing—measure time spent alone, on phone, frequency and duration of visits by others, and number of visitors present. Note that the processor may distinguish the object 104 from others, as explained herein. For example, based on the set of data received from the radar, the processor may track micro-behaviors (e.g., medication use, dressing, grooming). For example, based on the set of data from the radar, which may be enhanced or supplemented (e.g., augmented) by data from other data sources disclosed herein, the processor may track the object 104 and another object 104 (e.g., a visitor, a pet) positioned or living within the area 100 based on the set of data and distinguish the object 104 living in the area 100 from the another object 104 positioned or living within the area 100 based on the set of data (e.g., by learning habits and signatures of the object 104 over time) before determining whether the object 104 is experiencing the event involving the object 104 within the area 100 based on the set of data. For example, over time, when the processor may be able to distinguish between the object 104 and the another object 104 in the area 100, the processor may determine whether the event is custom (or unique) to the object 104 based on distinguishing the object 104 from the another object 104 based on the set of data.

One use case of the device 102 is to detect evidence of illness via the processor. For example, if the object 104 is an elderly human, then some illnesses may be dangerous to health and safety thereof. A number of illnesses are evidenced by abnormalities which the processor can identify based on the set of data from the radar and call attention to (e.g., electronically notifying an individual, a family member, or a physician by a sound prompt, a warning message, or a mobile app). The processor (e.g., running various AI algorithms) and a cloud analytics logic (e.g., running within a cloud computing instance) permit correlation of various factors (as sent by the device 102 via a communication unit) that can be helpful in recommending or suggesting, by an output device (e.g., a speaker, a display) of the device 102 as requested by the processor, at least some medical evaluation. Examples of these illnesses include cardiorespiratory illnesses—an irregular heart rhythm (via cardiac rate analysis as detected by the processor from the set of data sent by the radar), a lack of cardiac reserve (increased heart rate over baseline during usual activity as detected by the processor from the set of data sent by the radar), or a lack of respiratory reserve (increased respiratory rate over baseline during usual activity as detected by the processor from the set of data sent by the radar). Examples of these illnesses include sleep disorders—a nocturnal awakening (via atypical rising during nighttime as detected by the processor from the set of data sent by the radar), a snoring pattern (via a microphone as detected by the processor), a sleep apnea (via analysis of respiratory rate and pauses as detected by the processor from the set of data sent by the radar or the microphone). Examples of these illnesses include neurocognitive illnesses—a cognitive decline (unusual repetition of behaviors as detected by the processor from the set of data sent by the radar), a retracing pattern (as detected by the processor from the set of data sent by the radar), an omission of cooking (as detected by the processor from the set of data sent by the radar), or a reduced self-care (as detected by the processor from the set of data sent by the radar). Examples of these illnesses include neuromuscular illnesses—movement disorders—via a gait analysis (as detected by the processor from the set of data sent by the radar), a time to rise analysis (as detected by the processor from the set of data sent by the radar) and ambulation speed analysis (as detected by the processor from the set of data sent by the radar), or a seizure detection (unusual movement, unusual movement preceding fall, post-seizure state as detected by the processor from the set of data sent by the radar). Examples of these illnesses include infectious illnesses—cough detection (as detected by the processor from the set of data sent by the radar or the microphone) may indicate an onset of influenza, pneumonia, upper respiratory infection, COVID; a bathroom or toileting frequency (as detected by the processor from the set of data sent by the radar) may indicate a presence of urinary tract infection or diarrhea or constipation. Examples of these illnesses include metabolic illnesses—bathroom use frequency (as detected by the processor from the set of data sent by the radar) may indicate uncontrolled diabetes or signs of urinary problems or gastro problems, or thyroid conditions may subtly alert a resting heart rate over time (as detected by the processor from the set of data sent by the radar). For example, with respect to various illnesses disclosed herein, the processor may be programmed to identify potential signs, onsets, or signatures of certain diseases (e.g., neurological diseases, neurodegenerative diseases, Parkinson's disease, Alzheimer's disease, facioscapulohumeral muscular dystrophy, Crohn's disease, chronic obstructive pulmonary disease, atopic dermatitis) based on the set of data from the radar.

One use case of the device 102 is to monitor chronic conditions (by the processor from the set of data sent by the radar). For example, if the object 104 is an elderly human, then some chronic conditions may be dangerous to health and safety thereof. A variety of factors contributing to the successful management of chronic conditions are related to an individual's behaviors, as, without their participation in care, that individual will deteriorate. In addition to understanding whether that individual's activities are promoting their wellness, the device 102 can detect changes (by the processor from the set of data sent by the radar) suggestive of that individual suffering from worsening in their conditions. There are various chronic conditions that may be monitored by the device 102 (the processor). For example, some heart failure or rhythm disturbances may be monitored by heart and respiratory rates (by the processor from the set of data sent by the radar), movement speed (by the processor from the set of data sent by the radar), time in physical activities (by the processor from the set of data sent by the radar), or medication use (by the processor from the set of data sent by the radar). Some asthma and chronic obstructive pulmonary disease (COPD) may be monitored by heart and respiratory rates (by the processor from the set of data sent by the radar), cough and wheezing measures (by the processor from the set of data sent by the radar), movement speed (by the processor from the set of data sent by the radar), or medication use (by the processor from the set of data sent by the radar). Some sleep disorders may be monitored by time spent sleeping (by the processor from the set of data sent by the radar), interruptions (by the processor from the set of data sent by the radar), snoring detection (by the processor from the set of data sent by the radar or the microphone), or heart and respiratory rate (by the processor from the set of data sent by the radar). Some neurobehavioral conditions may be monitored by tracking of potential declines of daily living (by the processor from the set of data sent by the radar), movement speed (by the processor from the set of data sent by the radar), medication use (by the processor from the set of data sent by the radar), or near-falls or falls (by the processor from the set of data sent by the radar). For example, the processor based on the set of data from the radar or augmented by data from other sensors, as disclosed herein, may fuse such data to detect not only falls (or other events), but at least estimate or forecast some emotional health, mood, and stress level of the object 104.

Figure 3:
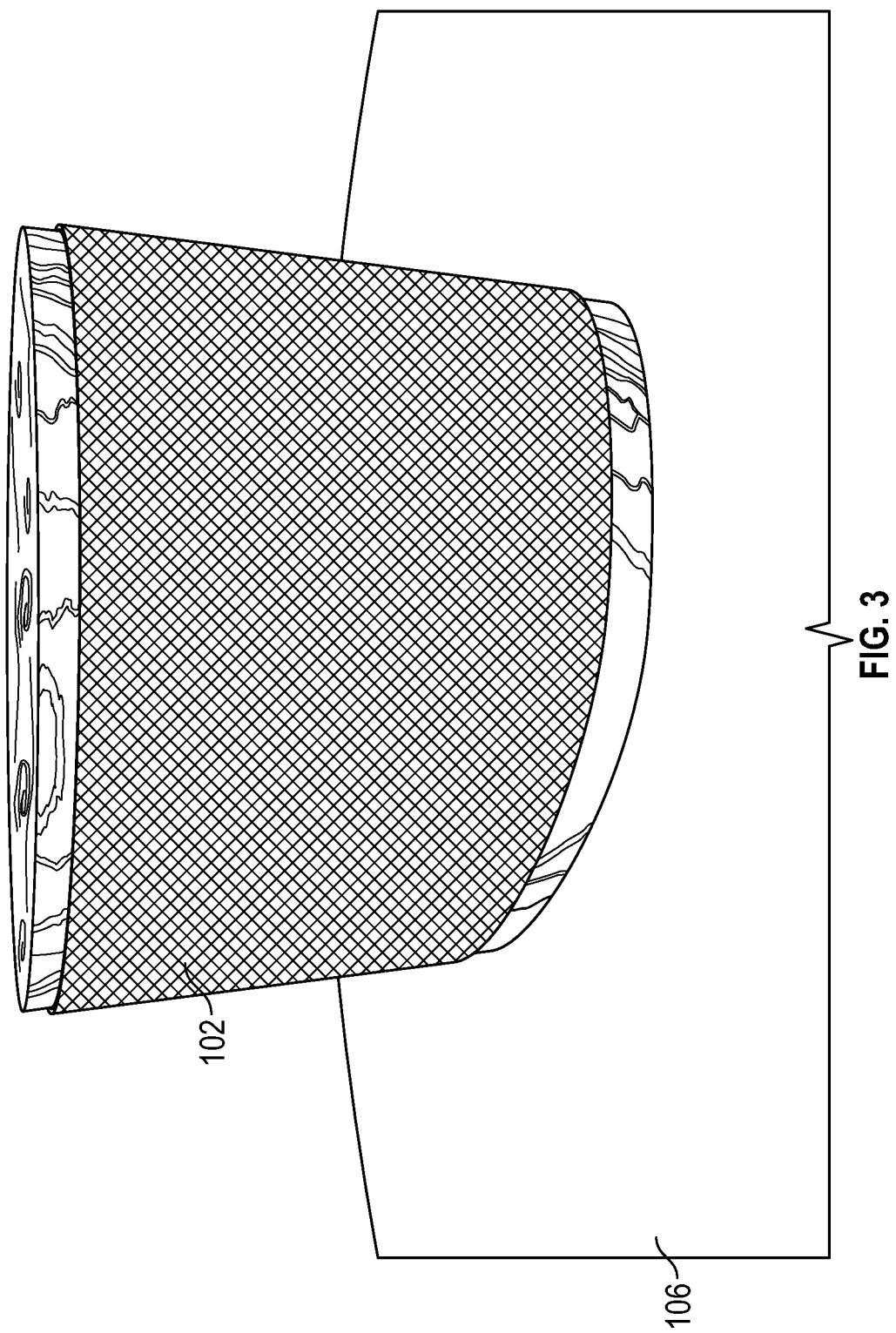
FIG. 3 shows an embodiment of a device including a radar according to this disclosure.
Figure 4:
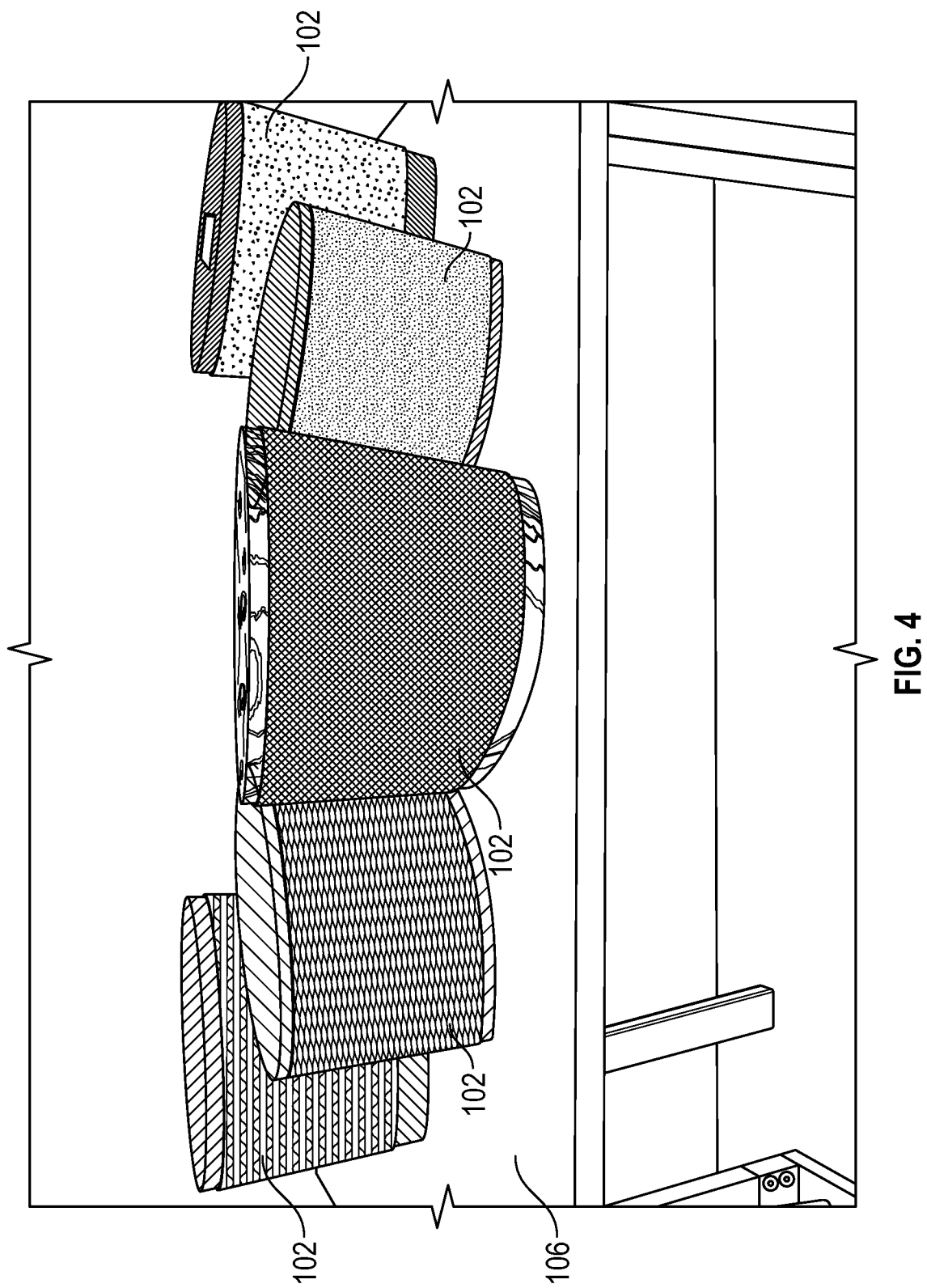
FIG. 4 shows a set of embodiments of a set of devices each including a radar or a sensor according to this disclosure.

FIG. 3 shows an embodiment of a device including a radar according to this disclosure. FIG. 4 shows a set of embodiments of a set of devices each including a radar or a sensor according to this disclosure. In particular, the device 102 is positioned on the stand 106. The device includes a housing having a top side, a bottom side, and a middle portion spanning between the top side and the bottom side. Note that the top side or the middle portion may be omitted.

The top side includes wood, but can include other suitable materials (e.g., plastic, metal, rubber, fabric, glass). The bottom side includes wood, but can include other suitable materials (e.g., plastic, metal, rubber, fabric, glass). The middle portion includes a fabric, but can include other suitable materials (e.g., plastic, metal, wood, rubber, glass). Note that the top side, the bottom side, and the middle portion can be selectively interchanged to create different visual appearance, as desired, as shown in FIG. 4.

Although the housing has an oval shape when viewed from top, this is not required and the housing (or another form of support) may be embodied in other ways (e.g., a container, an enclosure, a box, a frame, a base, a cube, a cuboid, a pyramid, a cone, a sphere, an ovoid, a television unit, a soundbar, a speaker, a bookend, a flowerpot, a planter pot, a vase, a furniture item, a table, a chair, a sofa, a bed, a crib, a shelf, a bookcase, a television stand, a house appliance, a dishwasher, a refrigerator, an oven, a stovetop, a toy, an exercise equipment item, a treadmill, a rowing machine, a musical instrument, a fixture, an electrical fixture, a plumbing fixture).

Figure 5:
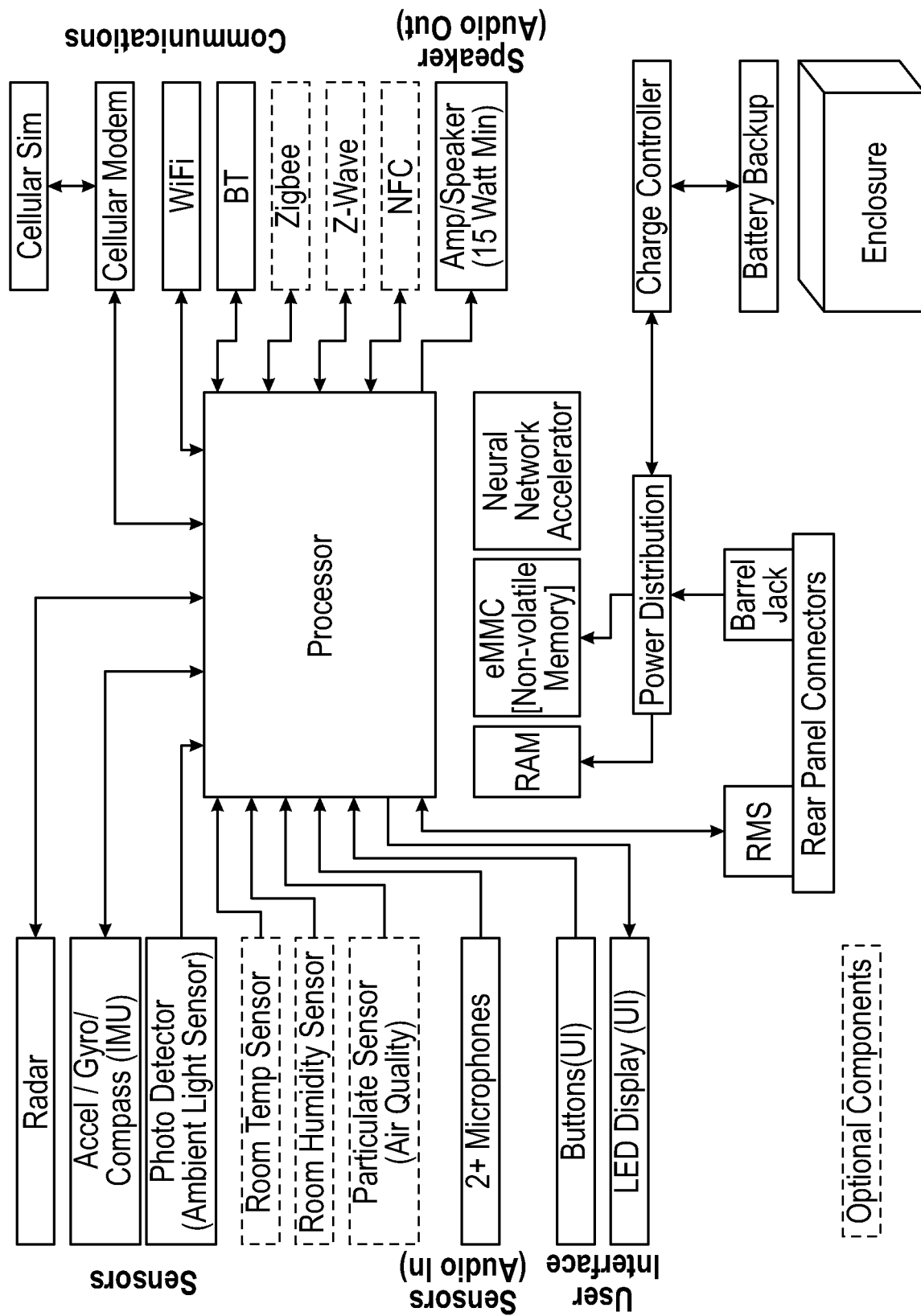
FIG. 5 shows a logic diagram of an embodiment of a device including a radar according to this disclosure.

FIG. 5 shows a logic diagram of an embodiment of a device including a radar according to this disclosure. In particular, the device 102 includes a housing (e.g., an enclosure) hosting (e.g., internally or externally) a power unit, a logic unit powered via the power unit, a communication unit (optional itself or any components thereof) controlled (any component) via the logic unit and powered (any component) via the power unit, a speaker unit (optional itself or any components thereof) controlled (any component) via the logic unit and powered (any component) via the power unit, a connector unit (optional itself or any components thereof) controlled (any component) via the logic unit and powered (any component) via the power unit, a user interface unit (optional itself or any components thereof) controlled (any component) via the logic unit and powered (any component) via the power unit, a microphone unit (optional itself or any components thereof) controlled (any component) via the logic unit and powered (any component) via the power unit, and a sensor unit (optional itself or any components thereof) controlled (any component) via the logic unit and powered (any component) via the power unit.

The logic unit includes a processor, a random access memory (RAM), a persistent storage (e.g., an embedded multimedia card, a solid-state drive, a flash memory), and a hardware accelerator (e.g., a neural network accelerator, a machine learning accelerator), although the hardware accelerator is optional. The communications unit (optional itself or any components thereof) includes a cellular SIM unit (e.g., a SIM card receiver and corresponding circuitry), a cellular modem, a Wi-Fi unit (e.g., a Wi-Fi chip), a Bluetooth (or another short-range wireless communication standard) unit (e.g., a Bluetooth chip), a Zigbee (or another short-range automation wireless communication standard) unit (e.g., a Zigbee chip), a Z-wave (or another short-range automation wireless communication standard) unit (e.g., a Z-wave chip), a Near Field Communication (NFC) unit (e.g., an NFC chip), and a registered jack (RJ). The communication unit is used in various communications, as disclosed herein. For example, if the device 102 needs to be paired (e.g., for configuration or setup) with a desktop or a mobile device (e.g., a phone, a laptop, a tablet, a wearable computer) or another device 102 or a sensor, as disclosed herein, then the Bluetooth or the Wi-Fi unit may be used. If the device 102 needs to be connected to Wi-Fi (e.g., for sending data formed by the processor to a cloud computing service or receiving data from a cloud computing service) or a desktop or a mobile device (e.g., a phone, a laptop, a tablet, a wearable computer) or another device 102 or a sensor, as disclosed herein, then the Wi-Fi unit or the RJ may be used. For example, if the device 102 has (e.g., internally or externally hosted by its housing) and needs to turn on an indicator light (of itself or another device), sound a general alarm (of itself or another device), or wants to measure characteristics of the object 104 (e.g., vitals) using another device, then Zigbee or Z-wave protocols (or other suitable automation communication protocols) may be used by lamps (of itself or another device), alarms (of itself or another device), health monitoring devices (of itself or another device), and general smart home automation (of itself or another device). If the device 102 needs to be configured for various operations, as disclosed herein, then such configuration can be done via a mobile app running on a mobile phone, a tablet computer, a wearable computer or another computing unit (e.g., a laptop, a desktop) operated by the object 104 or the user and in communication with the device 102, as disclosed herein. This arrangement simplifies gathering configuration information (e.g. a Wi-Fi password, an authorization code). Whatever computing unit is used can then use its NFC unit to transmit (e.g., wirelessly) that configuration information to the device 102 (e.g., to its NFC unit), which may in turn allow the device 102 to use other communication standards. Note that Bluetooth communication technology (or other short range communication protocols) may additionally or alternatively be used to transmit such configuration information (and the computing unit and the device 102 may be configured accordingly). If the device 102 needs to synchronize its operation or exchange data with another device 102 (e.g. when two radars are cooperating to scan the area 100), then any communication components in the communications unit (e.g., the Bluetooth unit, the Z-wave unit, the Zigbee unit, the Wi-Fi unit, the RJ unit) can be used. The speaker unit (optional itself or any components thereof) includes an amplifier or a speaker. The speaker unit is used in various sound, vocal, or audio outputs, as disclosed herein. For example, configurations, health, safety, suggestions, recommendations or wellness content may be output by the speaker unit, as disclosed herein. The power unit includes a rear panel connector (optional), a barrel jack (optional), a power distribution/supply, a charge controller (optional), and a battery backup (optional). The user interface unit (optional itself or any components thereof) includes a physical interface (e.g., a button, a dial, a lever, a switch) and a virtual interface (e.g., a touch or non-touch display presenting a graphical user interface). The user interface unit is used in various tactile or visual outputs, as disclosed herein. For example, configurations, health, safety, suggestions, recommendations or wellness content may be output by the user interface unit, as disclosed herein. The microphone unit (optional itself or any components thereof) includes a set of microphones. The microphone unit is used in various capture of sounds, vocals, or audio inputs, as disclosed herein. For example, vocal commands or sounds identified in the area 100, whether from the object 104 or others, may be input by the microphone unit, as disclosed herein. The sensor unit includes the radar, an accelerator (optional), a gyroscope (optional), an inertial measurement unit (optional), a photo detector (optional), a local temperature sensor (optional), a local humidity sensor (optional), and a particulate sensor (optional). The sensor unit is used in various sensory capture of inputs, as disclosed herein. For example, sensory inputs identified in the area 100, whether from the object 104 or others, may be input by the sensor unit, as disclosed herein. For example, the photo detector, the local temperature detector, the local humidity detector, or the particulate sensor may sense its ambient environment and its data for the processor to act or determine to act accordingly. For example, the photo detector, the local temperature detector, the local humidity detector, or the particulate sensor may sense fire, smoke, carbon monoxide, pollution, or other events such that the processor issues alerts via the communications unit (e.g., call emergency services or predetermined phone number, turn off or deactivate gas supply, electrical panel, or water main valve) or the speaker unit (e.g., guide the object 104 out of the area 100) or the user interface unit. As such, when the device 102 includes the communication unit, where the processor is coupled (e.g., mechanically, electrically, logically) to the communication unit, the processor may take the action including instructing the communication unit to send a message to another device 102 (e.g., local) or a computer (e.g., a desktop, a laptop, a mobile phone) remote from the area 100, where the message contains a content relating to the object 104, the area 100, or the event.

Figure 6:
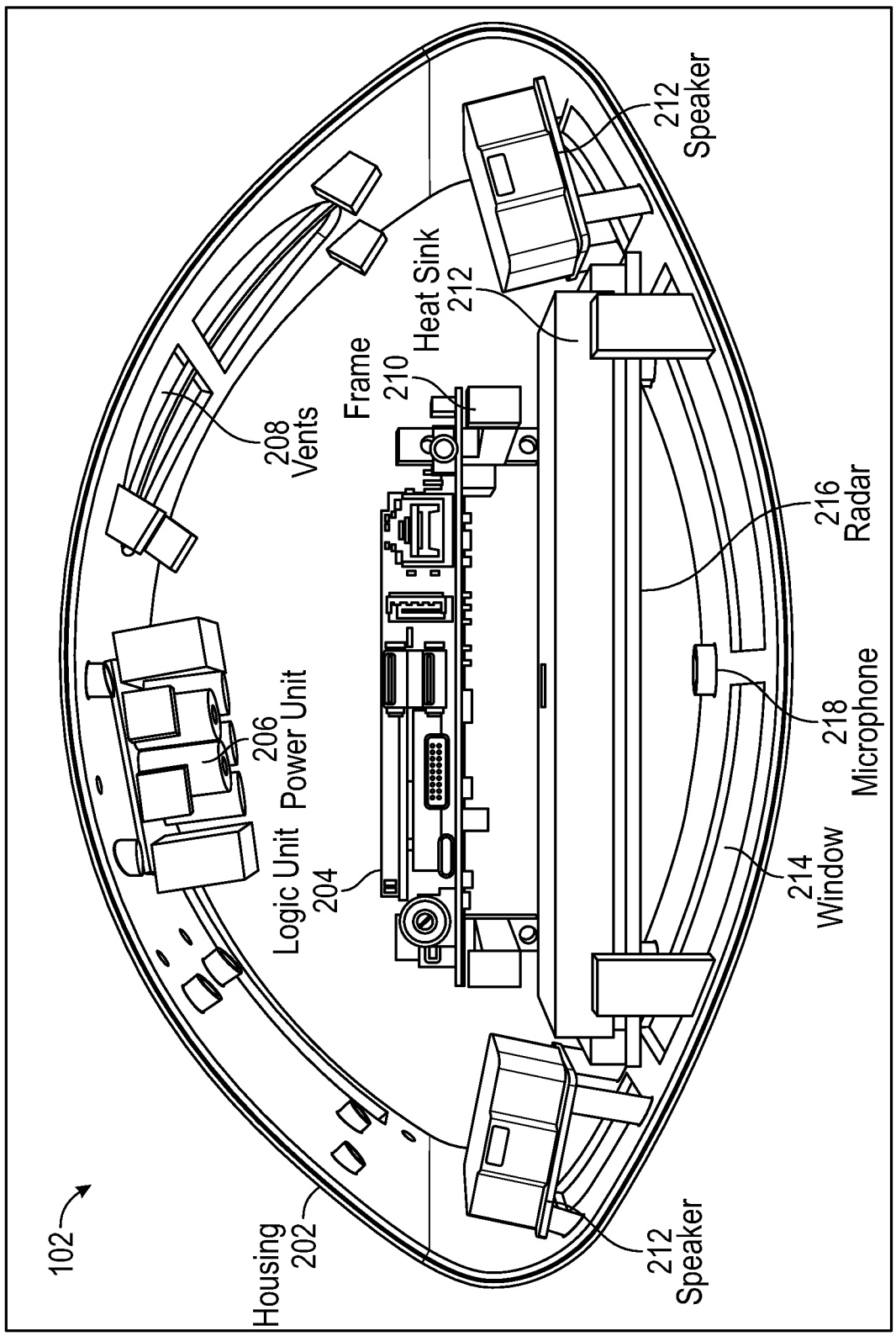
FIG. 6 shows an internal diagram of FIG. 3 according to this disclosure.
Figure 8:
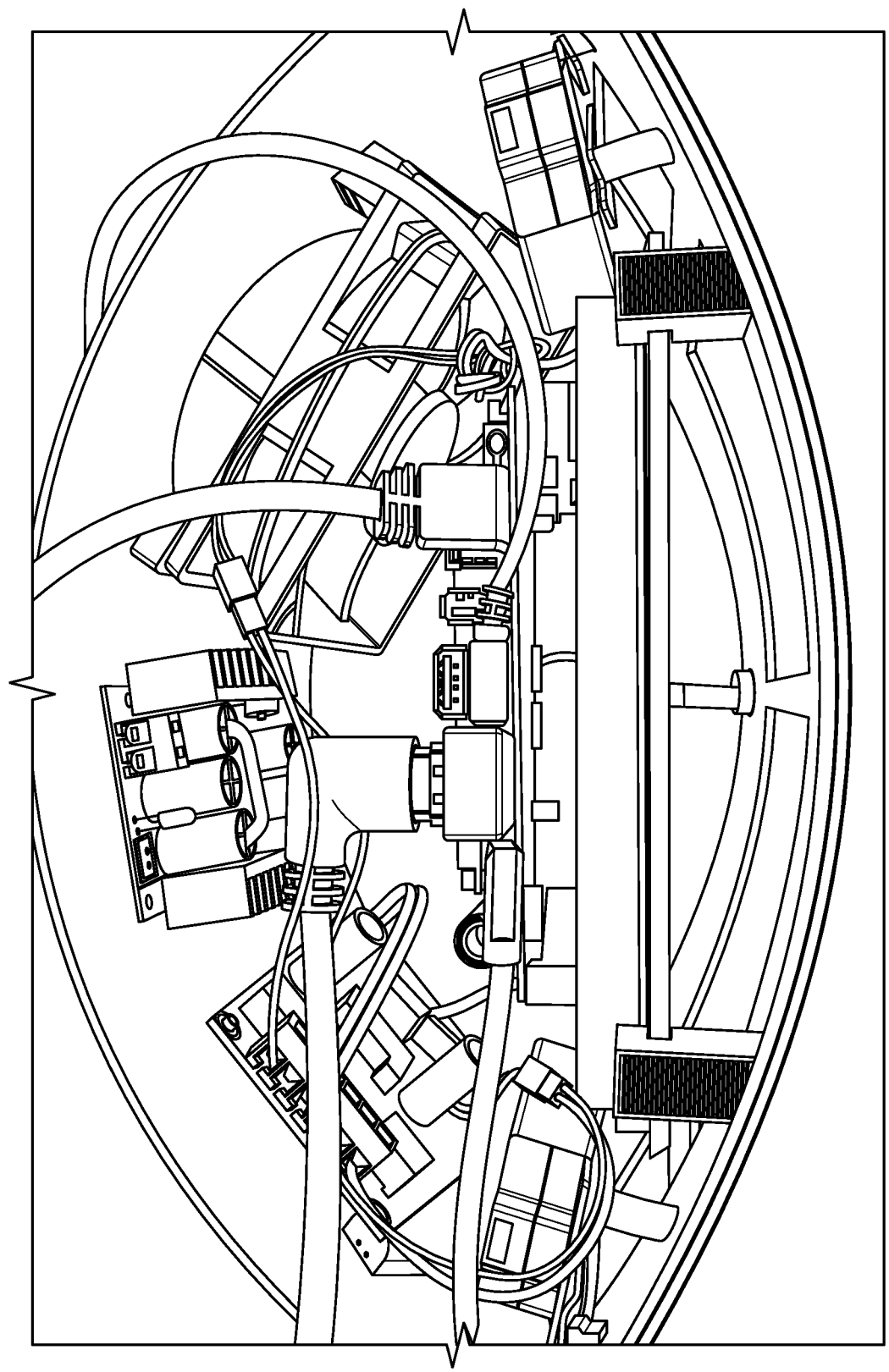
FIG. 8 shows a photograph of an internal cavity of FIG. 3 based on FIG. 6 according to this disclosure.

FIG. 6 shows an internal diagram of FIG. 3 according to this disclosure. FIG. 8 shows a photograph of an internal cavity of FIG. 3 based on FIG. 6 according to this disclosure. In particular, the device 102 includes a housing 202, a logic unit 204, a power unit 206, a vent 208, a frame 210, a heat sink 220, a speaker 212, a window 214, a radar 216, and a microphone 218, some of which are shown in FIG. 5. The housing 202 hosts the frame 210. The logic unit 204 is secured or mounted (e.g., fastened, mated, interlocked, adhered) onto the frame 210 such that the logic unit 204 extends between the power unit 206 and the window 214, although this positioning can vary. The power unit 206 powers the logic unit 204. The power unit 206 is secured or mounted (e.g., fastened, mated, interlocked, adhered) to the housing 202 such that the logic unit 204 extends between the power unit 206 and the heat sink 220 or the radar or the window 214. The power unit 206 faces the logic unit 204, although this positioning can vary. The vent 208 is defined by the housing 202 such that the logic unit 204 extends between the vent 208 and the window 214 the speaker 212 (on left), although this positioning may vary. Although the vent 208 is formed by a set of symmetrical openings, this is not required and can vary as needed (e.g., asymmetrical openings). The heat sink 220 is positioned between the radar 216 or the window 214 and the logic unit 204 or the power unit 206, although this positioning may vary.

The vent 208 and the heat sink 220 are collectively used as a group of passive cooling components, which may impact how the heat sink 220 is designed (e.g., size, shape) or positioned, or how the housing 202 is designed (e.g., size, shape), or how the vent 208 is designed (e.g., size, shape) or positioned, each to optimize convection (e.g., move rising heat away). This may be technologically advantageous because the vent 208 and the heat sink 220 operate with minimum or no noise, which may be desired in certain environments (e.g., elderly care recipients). However, the group of passive cooling components may be technologically disadvantageous due to the heat sink 220 potentially being larger than desired, which may be financially expensive, space limiting, or not readily available due to supply shortages. Likewise, the group of passive cooling components may be technologically disadvantageous since the logic unit 204 or the radar 216 may run hotter, as an amount of heat that the vent 208 or the heat sink 220 removes is more dependent on an ambient temperature of an air around the heatsink 220 or the housing 202 (e.g., next to a radiator, a heater, or a vent in wintertime). Therefore, in situations where the group of passive cooling components may be technologically disadvantageous, an active coolant may be used. The active coolant may be a cooling fan, a cooling liquid circulation system, or another suitable coolant. The active coolant, when embodied as the cooling fan, may force ambient air over the radar 216 or the logic unit 204 to be dispersed, which may enable more effective cooling that the group of passive cooling components. However, the active coolant (e.g., a cooling fan) may have moving parts or balanced parts, which may produce noise due to the ambient air that is moved. Likewise, the active coolant may also wear out or rattle, which may be undesired in certain environments (e.g., elderly care recipients). Similarly, the active coolant may reduce long-reliability of the device 102, increase rate of dust collection, increase potential for mechanical failure or part misbalancing, increase wear on connectors, and add noise to radar measurements, which may require more filtering and compensation thereof, if possible. As such, depending on use case, the radar may be actively cooled or passively cooled.

When the housing 202 includes two speakers 212, as shown in FIG. 6, the logic unit 204 or the heat sink 220 or the radar 216 can extend between those speakers 212, although those speakers 212 can be positioned in other locations, whether internal or external to the housing 202. Note that there may be more than two speakers 212 or one speaker 212 or no speakers 212 at all. The speaker is powered via the power unit 206 and controlled via the logic unit 204.

The radar 216 (e.g., a circuit board having a receiver with an antenna and a receiver with an antenna or a transceiver with a transmitting antenna and a receiving antenna) extends between the window 214 and the heat sink 220 or the logic unit 204 or the power unit 206, although this positioning may vary. The radar 216 tracks (e.g., transmits and receives) through the window 214, which minimizes occlusion, interference, and noise, although the window 214 may be absent. As shown in FIG. 6, the housing 202 includes two windows 214 that are symmetrical to each other, but there may be more than two windows 214 or the windows 214 may be asymmetrical to each other.

The microphone 218 is positioned adjacent to the window 214 such that the radar 216 or the heat sink 220 or the logic unit 204 extend between the microphone 218 and the power unit 206, although the microphone 218 may be omitted or positioned elsewhere. The microphone 218 is powered via the power unit 206 and controlled by the logic unit 204 to supplement, enhance, or augment the radar 216 or receive user inputs, as disclosed herein.

Figure 10:
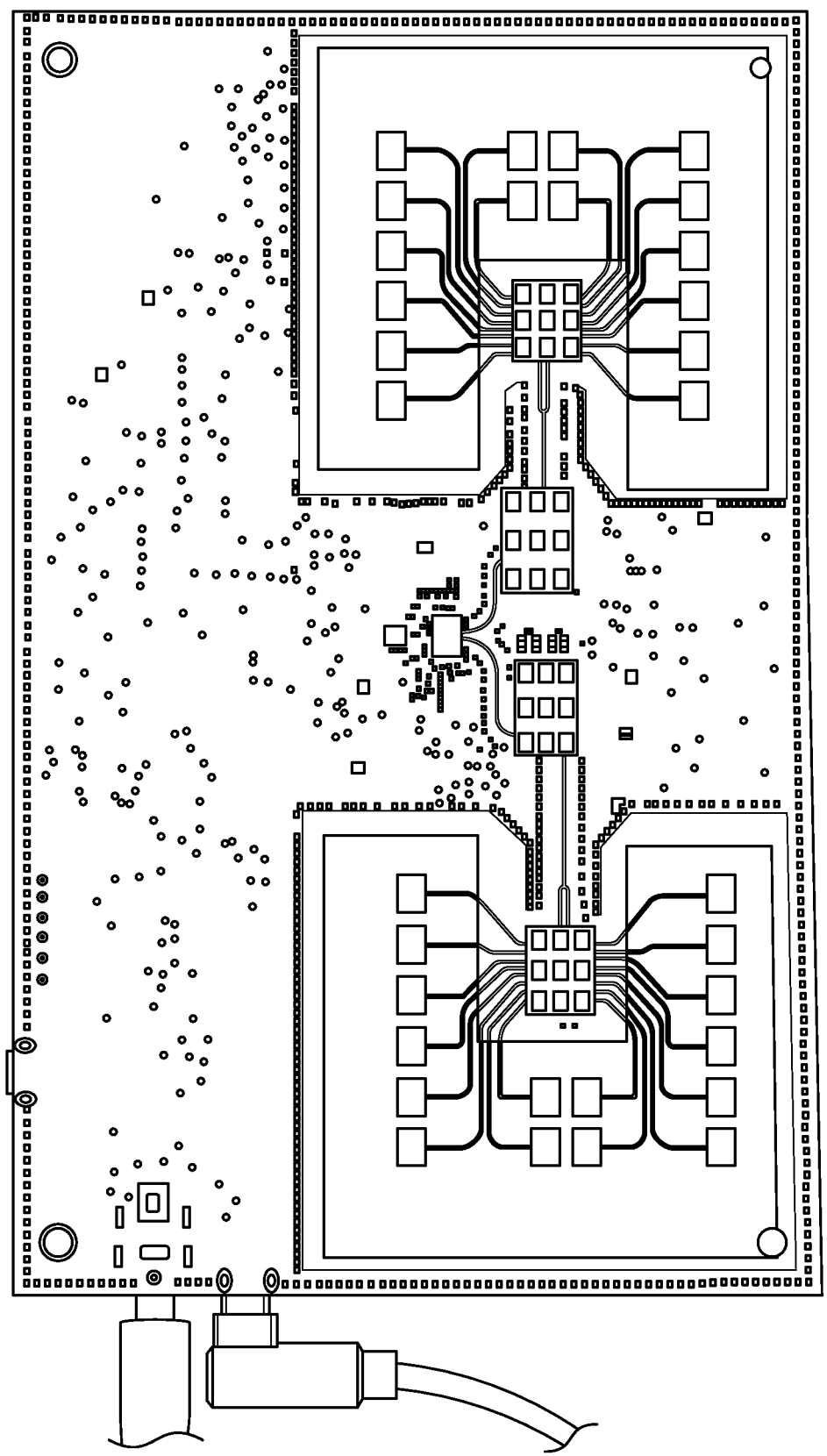
FIG. 10 shows an embodiment of a circuit board with a set of antennas of a radar according to this disclosure.
Figure 11:
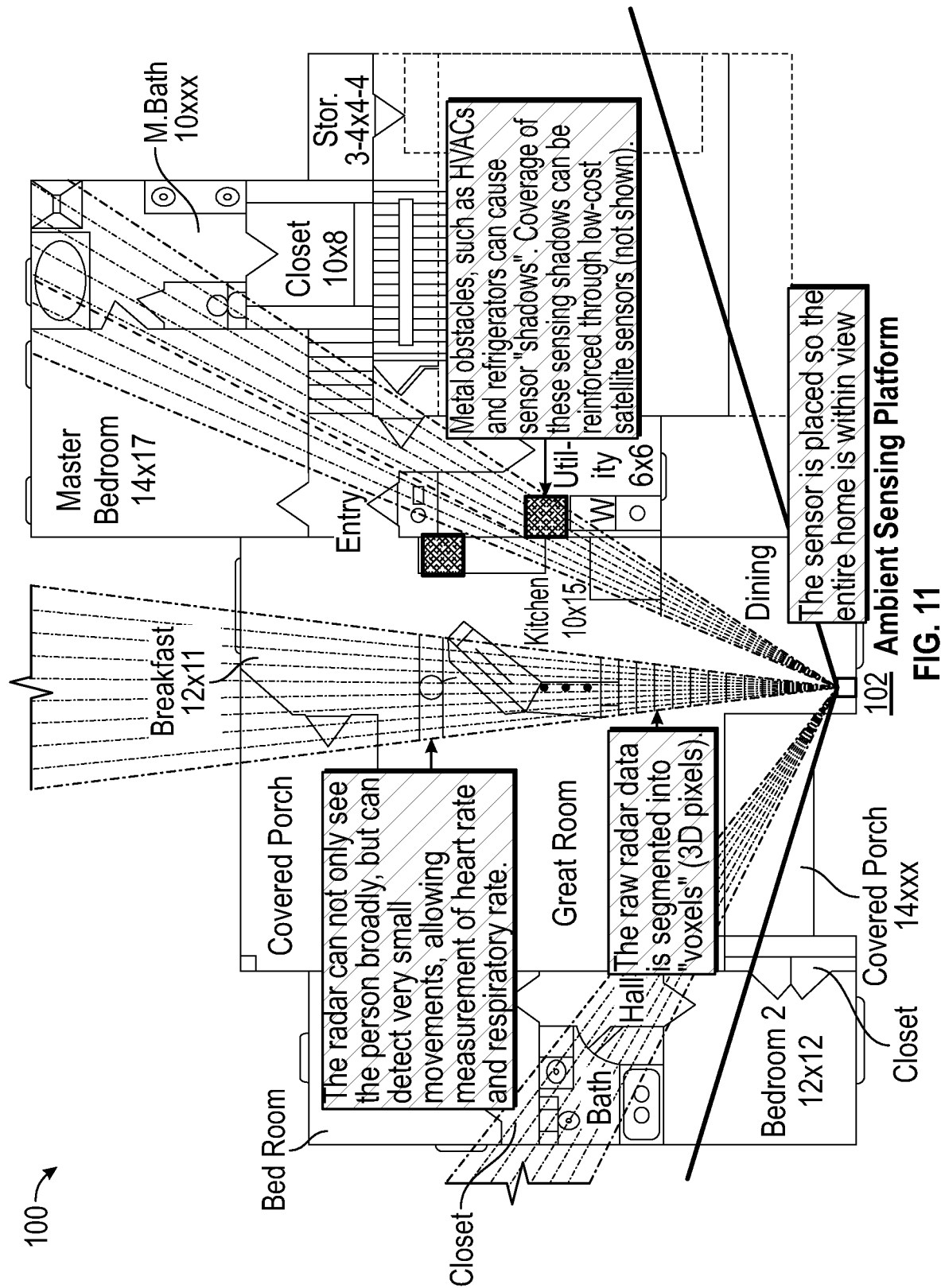
FIG. 11 shows an embodiment of a field of coverage of the device of FIG. 3 according to this disclosure.

FIG. 10 shows an embodiment of a circuit board with a set of antennas of a radar according to this disclosure. FIG. 11 shows an embodiment of a field of coverage of the device of FIG. 3 according to this disclosure. In particular, as explained herein, the radar may operate on a digital-encoded time-of-flight principle, which can be embodied in various ways. The radar can be used to track or monitor safety, health, well-being or care of individuals, as controlled by the processor. For example, the radar can transmit pulses and then measure a time for reflections (e.g., echoes) off objects (e.g., humans, furniture, home appliances, walls, floor, ceiling) to return thereto (e.g., receiver, transceiver, sensor, distance sensor). For example, the radar can be operating through phased arrays of transmit and receive antennas to create highly directional measurements. This is shown in FIG. 10, where the radar includes a circuit board having two arrays of antennas (small golden rectangles although other color or shapes are possible) and heat sinks (small black rectangles although other color or shapes are possible) covering main radiofrequency processing chips. For example, the radar can include a set of phased arrays each comprising a set of patch antennas enabling the radar to track the object 104 living or present within the area 100.

The device 102 includes the processor coupled (e.g., electrically, logically, mechanically) to the radar to achieve various design goals or performances. Some of these goals or performances may enable edge computing and hardware-accelerated artificial of neural networks (ANNs), which may include various corresponding models thereof, to enable various raw sensing and processing capabilities to build a variety of software-based applications to support various types of use cases, as described herein. For example, some of ANNs can include a convolution neural network, a recurrent neural network, a long short term memory neural network, or other suitable forms of ANNs. These forms of edge computing and hardware-accelerated ANNs may enable the processor to handle various use cases based on the set of data from the radar. These use may include the processor tracking a heart rate or beat of the object 104 based on the set of data from the radar by using various penetrating properties of the radar, capture part of at least some "back-scatter" (aka reflected signal) that is reflected by the object 104, and allowing tracking the heart rate or beat of the object 104. These use cases may include the processor tracking a respiratory rate based on the set of data from the radar, which may be tracked similar to the heart rate, as described herein, or process the signal to identify some slower respiratory variations based on the set of data from the radar. These use case may include the processor tracking the location of the object 104 within the area 100 based on the set of data from the radar, i.e., persistent knowledge of the location of each individual moving through the area 100 (within the field of view 130). These use cases may include the processor tracking fall detection based on the set of data from the radar—an ability to detect an orientation of the object 104 and its velocity of change. These use cases may include the processor being programmed for a specific room geometry based on the set of data from the radar—a location of large planar surfaces (e.g., floor, walls, ceiling, furniture, home appliances). These use cases may include the processor tracking pose of the object 104 based on the set of data from the radar—an orientation of the object 104. These use cases may include the processor performing object classification based on the set of data from the radar—identification of furniture or home appliances can provide context to whether someone is sleeping in a bed or lying on a table. These use cases may include the processor tracking various activities of daily living based on the set of data from the radar—an ability to accurately determine timing and frequency of living patterns including sleeping, drinking, eating, toileting, socializing, and micro behaviors, such as taking medications.

Given current ongoing chip shortage, the device 102 may be designed to leverage 5G chips to reduce or mitigate this risk. For example, since the radar may be an all-digital design (although non-all-digital or hybrid design is possible), the radar can leverage existing communications chips (e.g., wireless RF receivers, wireless RF transmitters, wireless radiofrequency transceivers, wired interface cards, waveguides). For example, 5G (or 3G, 4G, 6G) cellular technologies may operate in the same or similar bands as the radar operating within the Ku-band, the K-band, or the Ka-band, leading to enormous, and ongoing, investment into components for radio systems at these frequencies. Leveraging these components provides the device 102 with an ability to achieve performance targets by minimizing or without requiring expensive and potentially risky design cycles for custom hardware; similarly, further improvements in performance driven by competition in a cellular market may impact the radar. In contrast, some radars rely on complex analog designs that will only see tangential benefits from these external market developments.

As explained herein, the device 102 may be used for tracking where the object 104 is located within the area 100 based on the set of data received by the processor from the radar and processed by the processor and detect falls of the object 104 within the area 100 based on the set of data received by the processor from the radar and processed by the processor. For example, when the object 104 is a human, the radar can detect the human's location and posture through at least one or two standard US walls (e.g., drywall), allowing the radar to "see" into adjacent rooms, bedrooms, bathrooms, hallways, pantries, or other areas 100 within the field of view 130, as shown in FIG. 11. However, since the radar may have coverage gaps (e.g., occlusions), the device 102 may be supplemented by another device 102 ("satellite" unit), which may be positioned within the area 100 or tracking the area 100, or a sensor (e.g., a camera, a microphone, a motion sensor, a proximity sensor, a distance sensor), which may be positioned within the area 100 or tracking the area 100. The devices 102 (e.g., housings) or the sensor may be spaced apart from each other to enhance resolution or coverage of the object 104 or the area 100. This may enable the device 102 to verify, corroborate or check its data, analysis, or conclusion or infer something about the object 104 or the area 100 that the device 102 cannot track or identify. For example, bathrooms are a common location for falls in a home when the object 104 is a human. The radar may generate the set of data with quality or resolution that degrades somewhat while the object 104 is under a running shower, but this does not interfere with detecting falls. Although some bathtubs can create sensor shadows, but the radar detects falls as those happen when the radar's view of the object 104 is not obstructed or occluded. However, when the radar's view of the object 104 is obstructed or occluded, the device 102 can communicate (e.g., wired, wirelessly, waveguide) with another device 102, which may be positioned within the area 100 or tracking the area 100, or a sensor, which may be positioned within the area 100 or tracking the area 100, to determine alone or collectively whether the object 104 is experiencing the event, as disclosed herein, such as a fall. For example, the second device 102 may track in the Ku-band, the K-band, or the Ka-band, as disclosed herein. Therefore, this configuration provides a complementary tracking or sensing ability, which may include using low-resolution infrared sensing (or other sensing modality, whether line-of-sight or non-line-of-sight, whether low-resolution or high-resolution, including ultrasonic sensors, LIDAR, radar, motion sensors, proximity sensors, distance sensors, or others). The "satellite" device 102 can be deployed to distant rooms and provides coarse or fine sensing of a person's location within the area 100, extending coverage into adjoining spaces that may be occluded (e.g. due to metal walls). The "satellite" device 102 can also have a microphone or a set of microphones, which can help detect certain falls, and provide for two-way communication (e.g., via the Bluetooth unit, the Wi-Fi unit, the RJ). Some, many, most, or all computations happens on the main unit 102, although these computations may be distributed or shared with other devices 102 (e.g., via the communication unit). Further, multiple main units or "satellite" units can be deployed as well to extend tracking range and provide coverage "behind" occlusions.

As such, if the device 102 is a first device 102 (with the first radar sending the first set of tracking data to first processor) positioned within the area 100 to track the object 104 living or positioned therein, there may be a second device 102 (with the second radar or sensor sending the second set of tracking data to the second processor) positioned within the area 100 to track or sense the object 104 living or positioned therein. The first device 102 and the second device 102 may be spaced apart from each other. For example, the first device and the second device may oppose each other. Therefore, the second device 102 may operate within the area 100, without interfering with the first device 102 (e.g., radar interference) operating in the area 100, such that the second radar (e.g., time-of-flight) or sensor (e.g., the sensor unit, the audio unit, the vision unit) operating within the area 100 tracks or senses the object 104 living or positioned in the area 100 when the first radar tracking the object 104 within the area 100 is or is not occluded from tracking the object 104 living or positioned within the area 100. The second radar or sensor generates a second set of data based on tracking or sensing the object 104 living or positioned in the area 100 when the first radar operating within the area 100 is or is not occluded from tracking the object 104 living or positioned within the area 100. The second radar or sensor sends the second set of data to the second processor when the first radar operating within the area 100 is or is not occluded from tracking the object 104 living or positioned within the area 100 such that the second processor determines whether the object 104 is experiencing a second event within the area 100 based on the second set of data and takes a second action responsive to the second event determined to be occurring within the area 100. The first radar and the second radar can both operate in a same band (e.g., the K-band, the Ku-band, the Ka-band) or within a same range in the same band (e.g., inclusively between about 23 GHz and about 25 GHz). The first event and the second event may or may not be the same event, or the first action and the second action may or may not be the same action. The first radar and the second radar or sensor may or may not overlap in their field of views. The first device 102 and the second device 102 can be configured such that the second processor communicates with the first processor (e.g., via the communication unit, the Bluetooth unit, the Wi-Fi unit) thereby enabling the first processor to confirm or validate the first set of data based on the second set of data and determine whether the object 104 is experiencing the event in the area 100 based on the second set of data confirming or validating the first set of data and take the action responsive to the event determined to be occurring in the area 100. The second processor may be configured to directly (e.g., housed in a common housing or having a common controller) or indirectly communicate with the first processor.

As explained herein, the radar may operate in the Ku-band, the K-band, or the Ka-band to track the object 104 in the area 100 by emitting waves. These waves are a non-ionizing form of radiation, which is regulated by Federal Communications Commission and other international regulatory bodies with respect to exposure to high-frequency non-ionizing radio waves by limiting a "dose" in terms of how much energy a body (e.g., the object 104) absorbs. Therefore, in some embodiments, transmit power of the radar is programmable, and the radar can conform or be configured to conform to all appropriate regulations, following guidance for uncontrolled exposure for the general public (i.e., everyday use), which can occur via the over-the-air update.

As explained herein, the radar may sense through typical walls found in common residences (e.g., a wooden or metal frame with a drywall and siding or a wooden or metal frame with a pair of drywalls). The radar may be a time-of-flight radar, a Doppler radar, or another suitable type of radar. The time-of-flight radar may measure a time for a pulse to travel to a reflecting object and back (e.g., echoes) or enables a direct observation of a static object. For example, a typical household item (e.g., a furniture item, a house appliance) is static and if the object 104 is an elderly or frail human, then the object 104 may be slow moving as well. The Doppler radar may measure a motion of a reflecting object as that object moves towards or away from the Doppler radar; "sideways" motion is generally not visible (although this may be possible with other radar technologies). When using the Doppler radar, the faster the motion of the object, the more something is seen (e.g., more data available). In general, observing humans relies on the argument that a human is never motionless, so something about their presence is always detectable. However, that also means fluttering fabrics are detected and can be distracting. Motionless objects can be or are missed. Between these two radar modalities, time-of-flight radar is much better suited to observe the relatively slow-moving home environment. Naturally, motion can be seen with time-of-flight systems by creating a "video" out of still frames. Hybrid designs are possible (e.g., radar mode switching), where Doppler radar is used to augment, supplement, substitute, enhance, or replace time-of-flight radar in detecting oscillating movements, such as tremors, skin-movement due to heart beat, chest deflection due to breathing, or others, as disclosed herein. In general, such oscillatory movements are slow relative to the wavelength of the radar, so the Doppler shift is often small and difficult to detect, but possible. However, higher frequency harmonics that result from the oscillatory motion can be more easily detected. For example, if the object 104 is a human, then a heart beating at 60 beats per minute can create a characteristic harmonic oscillation in the hundreds of Hz. Doppler radars can detect these harmonics and allow the device 102 (e.g., the processor) to disambiguate some or various oscillatory motions from intentional movement. For example, this disambiguation may manifest itself from detecting breathing where a natural human respiratory rate is on the order of a few Hz. However, human movement, such as swinging arms while walking also occur at a similar frequency. Detecting higher frequency harmonics that result from breathing but not arm-swinging can give the Doppler radar a technical advantage in detecting respiratory rate despite movement. Note that the Doppler radar (and Doppler information) can be used for monitoring people, as disclosed herein. Note that some versions of existing Doppler radar products tend to have fairly limited performance on human-monitoring tasks. These products can lose their ability to detect activity within about five feet from the source. Likewise, these products also require people to stand within about one-to-two feet away, and very still, to be able to measure heart rate and respiration. Regardless, the time-of-flight radar, the Doppler radar, or any other suitable radar may be used.

As explained herein, the device 102 may be supplemented, enhanced, or augmented by data from line-of-sight sensing (e.g., cameras, LIDAR, high-frequency radar). For example, many technologies rely on having a direct line-of-sight between a sensor and the object 104 being detected. Some optical camera-based, infrared, acoustic, or LIDAR-based solutions rely on line-of-sight; some high-frequency radars (specifically, some versions at about 60 GHz or about 76 GHz to about 81 GHz) penetrate materials very poorly and are effectively limited to line-of-sight as well, but can be used to supplement the device 102. Some line-of-sight-based systems have difficulty providing uniform coverage of typical room environments. Rooms are not rectangular and furniture creates occlusions, creating significant challenges. For example, someone who falls behind a table or countertop is likely not in view of a single in-room sensor. In contrast, the radar, as disclosed herein, will still be able to directly track the person behind that obstacle. Moreover, some line-of-sight technologies can only operate in a single room, requiring their units to be set up in each room and space in living areas to provide adequate coverage. In addition to various financial costs of these devices, there is also professional installation cost for such setups that makes business models untenable. In contrast, the device 102 may cover living spaces up to about 2000 sq ft (although more or less is possible based on various factors), works through walls, and can be extended with additional base units (e.g., another device 102 or a sensor) for broader coverage (e.g., for larger homes, multiple floors) or "satellite" device 102 to provide coverage in occluded adjoining spaces. Further, computer vision-based systems require people to accept a camera in their most private spaces, which is hard to achieve (e.g., US user surveys have proven that fewer than 42% of seniors are willing to accept this in their bedrooms and in Europe, the numbers are even lower).

Figure 12:
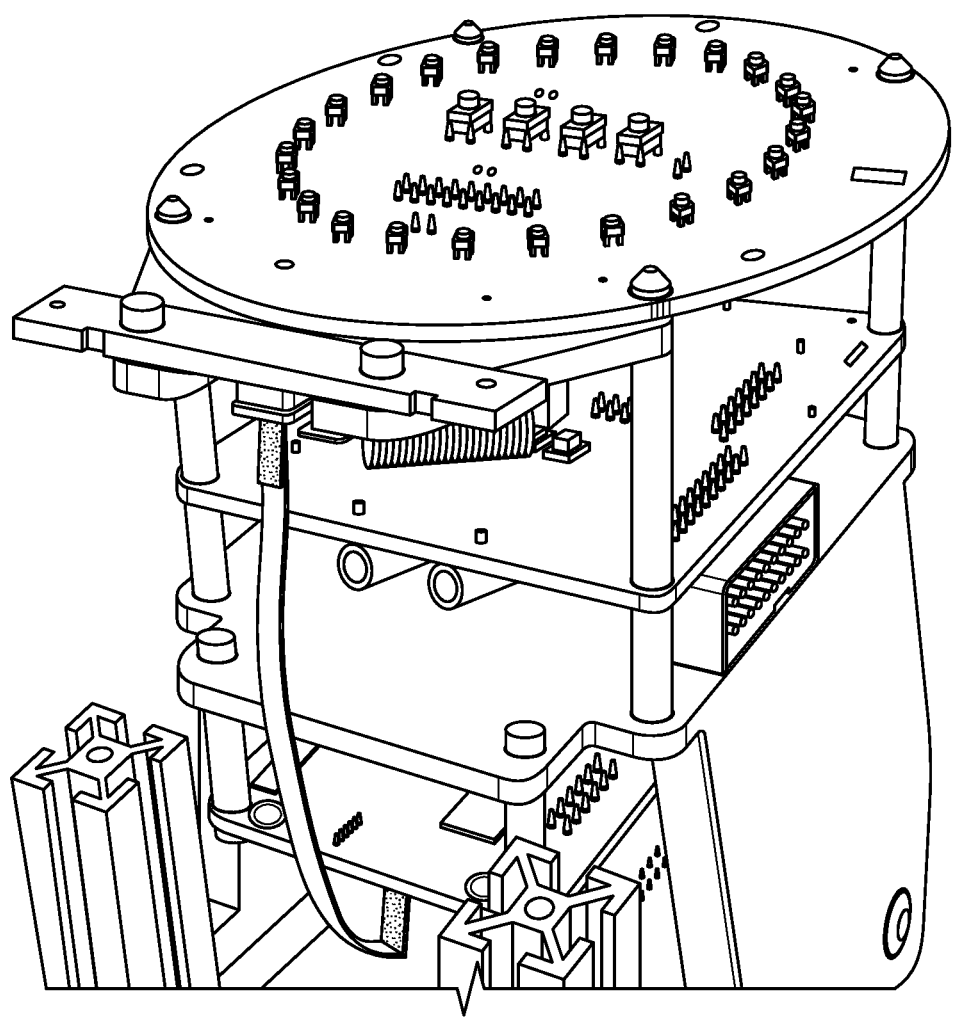
FIG. 12 shows an embodiment of a set of microphones of the device of FIG. 7 according to this disclosure.

FIG. 12 shows an embodiment of a set of microphones of the device of FIG. 7 according to this disclosure. FIG. 13 shows an embodiment of a microphone of the device of FIG. 7 according to this disclosure. FIG. 14 shows an embodiment of a raw reading from the device of FIGS. 1-7 and a virtual skeleton formed by the device of FIGS. 1-7 from the raw reading according to this disclosure. In particular, the device 102 may include the microphone unit, as shown in FIG. 5 and controlled by the processor for various purposes. For example, one of these purposes is to supplement (e.g., verify, validate, confirm, corroborate) the set of data generated by the radar and sent to the processor for processing, as disclosed herein. For example, the microphone unit may be used to receive vocal commands from the object 104 to control a voice assistant (e.g., Siri, Google Assistant) running on the processor. The microphone unit may include a microphone or a set of microphones. The microphone unit is configured to be sensitive and robust so that the microphone unit is accurate and satisfying to use, and extensible to support an increasing range of capabilities overtime, while also being cost-effective. The microphone unit delivers a "voice-first" conversational user experience, enables multi-party communication (e.g., device 102 to device 102 or device 102 to a remote phone or computer), and provides rich context—with user consent—about people and their activity. In such situations, the device 102 includes the speaker unit correspondingly controlled by the processor.

The device 102 uses the microphone unit and the speaker unit to talk to the object 104 (or its agent) for easy setup, without the device 102 needing to download any dedicated apps; respond to conversational voice commands; enable communication with loved ones, caregivers, and care providers (e.g., pre-programmed call numbers, chat names); and get the object 104 help when the device 102 detects imminent danger or when the object 104 asks for help. However, note that other embodiments, can involve apps downloaded from an app store (e.g., Google Play, iTunes).

The microphone unit may be used to capture sounds that indicate falls, as determined by the processor, and that can help confirm or validate what the radar detects to reduce false positives. For example, in case of data, information, or indication from the radar conflict with the microphone unit, then the radar can control (although this can be reversed or no controlling default is currently selected or unavailable), as determined by the processor. The microphone unit can capture loud sounds, such as crashes or breaking glass, that might indicate, as determined by the processor, other safety-critical situations or break-ins or fire or weather events. The microphone unit can capture sounds from kitchens and bathrooms that indicate, as determined by the processor, various daily routines and self-care. The microphone unit can capture voices that may indicate, as determined by the processor, social activity or media consumption. The microphone unit can capture airway sounds, such as coughing, wheezing, difficulty breathing, or snoring, that may indicate, as determined by the processor, whether a pulmonary disease is starting or deteriorating. The microphone unit can capture tone of voice that may indicate, as determined by the processor, emotion—sadness, anger, frustration, happiness—or signs of increasing depression. The microphone unit can capture additional audio context learned from the object 104 over time and associated with certain behaviors or symptoms of the object 104.

The microphone unit can include an array of three (although two or four or more) digital microphones (although analog microphones are possible). These microphones have a good signal-to-noise ratio, which will assist the device 102 in hearing commands and other sounds from as far as possible (e.g., within about 15, 14, 13, 12, 11, 10, 9, 8, 7, 6, 5, 4, 3, 2, 1 feet or meters indoors). In addition to these microphones, the microphone unit subsystem may include a signal processing chip that provides 3D direction-of-arrival information for sound sourcing.

The microphone unit can include two distinct microphone processing chains, any of which may be executed by the processor for the microphone unit. First is a voice processor, which performs echo cancellation and voice isolation, in preparation for processing by the voice assistant. Second is a direction-of-arrival analysis processor, which uses all three microphones to isolate multiple sources of sound and localize where those sounds originate within the area 100 being monitored. Therefore, the processor may localize sources of sounds (e.g., voices, falls) to allow the processor (e.g., its edge AI algorithms) to correlate those sources or sounds with radar data—or vision data during training. Likewise, the processor may use this sound information as location information that will augment activity recognition. Similarly, the processor may isolate separate sounds. For example, background noise from a TV or vacuum isolated from a person speaking, to improve the processor's ability to hear commands and recognize sounds. As such, when the device 102 includes the set of microphones, where the processor is coupled to the set of microphones to control the set of microphones (e.g., receive data), the processor may be programmed to activate the set of microphones such that the set of microphones receives a set of acoustic inputs generated from the object 104 living or positioned within the area 100 and sends the set of acoustic inputs to the processor such that the processor isolates the set of acoustic inputs, localizes where the set of acoustic inputs originated from within the area 100 based on the set of acoustic inputs being isolated, confirms or validates the set of data based on localizing where the set of acoustic inputs originated from within the area 100, and takes the action responsive to the event determined to be occurring within the area 100 based on the set of data being confirmed or validated by the set of acoustic inputs. Note that although the microphone unit may have its circuit board mounted on top, as shown in FIG. 12, this is not a requirement and this circuit board may be positioned elsewhere.

As explained herein, the device 102 may include a vision unit (e.g., an optical camera, an infrared camera) and controlled by the processor for various purposes. For example, one of these purposes is to supplement (e.g., verify, validate, confirm, corroborate) the set of data generated by the radar and sent to the processor for processing, as disclosed herein. For example, the vision unit may be used to receive gesture commands from the object 104 to supplement control of the voice assistant running on the processor. For example, the vision unit can include a high-resolution (e.g., 4K, 8K) video camera (e.g., red-green-blue) that the processor can optionally enable as needed, which can be with user consent. This video camera, which may work in a variety of lighting conditions, augments various datasets available to the processor to enhance training of various edge AI algorithms, especially to identify people via the radar subsystem. Although the device 102 can include this resulting edge AI algorithm, this is not required and the object 104 (or its agent) can exclude or disable the vision unit, if desired.

The video camera may use a wide-angle lens, which can be a fisheye lens, to provide good visibility of the room the video camera is placed in. Such cameras can be integrated modules including sensors, lenses, and supporting electronics. Note that prior to image processing, the imaging data can be pre-processed (e.g., dewarping). The video camera can provide the imaging data to the processor to complement the set of data the processor receives from the radar. The imaging data may be used to support training and validation of a location, body position, or identity of people within view of the video camera. The processor can compare this imaging data to the set of data received from the radar or data received from the audio unit at least within the area 100 the device 102 is positioned. Additionally, the imaging data can also be useful for recognizing daily activities and training the radar before the radar is used by the object 104 or while the radar is tracking the object 104. Also, there are technologies for extracting vital signs, such as heart-rate, directly from the imaging data, which may be integrated for training use for various edge AI algorithms. Since there is a possibility that the vision unit may be used in various conditions (e.g., daytime, nighttime), the video camera may operate in lighting conditions ranging from full-sun to completely dark. To meet this need with a single camera (although multiple cameras can be used feeding the processor), the video camera may use a dual-band filter, which allows the video camera to observe both visible-spectrum (red-green-blue) and near-infrared light. The device 102 can also include its own near-infrared light source for operation at night. Although there may be a disadvantage of using this dual-band filter (e.g., red-green-blue colors are mildly distorted), this may be compensated for or may not impact various uses, as disclosed herein. As such, when the device 102 includes the camera (e.g., optical or infrared) and the processor is coupled (e.g., mechanically, electrically, logically) to the camera to control the camera (e.g., receive imagery), then the processor may be programmed (or the user may be instructed) to activate the camera such that the camera receives an imagery generated from the object 104 living within the area 100 and sends the imagery to the processor such that the processor confirms or validates the set of data and takes the action responsive to the event determined to be occurring within the area 100 based on the set of data being confirmed or validated. The camera may include a dual-band filter configured to allow the camera to observe in a visible-spectrum (RGB) and in a near-infrared light.

As explained herein, the device 102 includes the processor (e.g., a controller, an edge processor, a single core processor, a multicore processor, a system-on-chip, a graphics processing unit, a hardware accelerator, a neural network accelerator, a machine learning accelerator) and the radar (e.g., a time-of-flight radar, a Doppler radar), where the processor is coupled (e.g., electrically, logically, mechanically) to the radar to control the radar (e.g., receive tracking data). For example, the processor may enable local or edge computing to enhance processing speed or provide data privacy or data security. For example, the sensors (e.g., radar, acoustic, vision) feed data (e.g., radar, acoustic, vision) to an edge processor. This is technologically advantageous for several reasons. First, this enables respect for people's privacy, as some, many, most, or all data (e.g., radar, acoustic, vision) collected rarely or never leaves the device 102 (although that is possible for cloud computing). Second, this minimizes bandwidth utilization, power usage, thereby reducing costs. Third, on-board processing minimizes latency and improves the responsiveness of user experience and the sensor platform to identify events as those occur.

The processor enables an edge computing platform, which can include a single core processor or a multi core processor, irrespective of whether these cores are local or remote to each other within the physical area being monitored. The multicore processor can include a plurality of independent cores. For example, the multicore processor is a computing component with two or more independent processing units, which are the units that read and execute program instructions, such as a front-end application, such as via multiprocessing or multithreading. The program instructions are processing instructions, such as add, move data, or branch, but the cores can run multiple instructions concurrently, thereby increasing an overall operational speed for the front-end application, which is amenable to parallel computing. The cores can process in parallel when concurrently accessing a file or any other data structure, as disclosed herein, while being compliant with atomicity, consistency, isolation, and durability (ACID) principles, which ensure that such data structure operations/transactions, such as read, write, erase, or others, are processed reliably. For example, a data structure can be accessed, such as read or written, via at least two cores concurrently without locking the data structure between such cores. For example, a figure and a text can be concurrently processed, as disclosed herein. Note that there can be at least two cores, such as two cores, three cores, four cores, five cores, six cores, seven cores, eight cores, nine cores, ten cores, twelve cores, tens of cores, hundreds of cores, thousands of cores, millions of cores, or more. The cores may or may not share caches, and the cores may or may not implement message passing or shared-memory inter-core communication methods. Common network topologies to interconnect cores include bus, ring, two-dimensional mesh, and crossbar. Homogeneous multi-core systems include only identical cores, heterogeneous multi-core systems can have cores that are not identical. The cores in multi-core systems may implement architectures, such as very long instruction word (VLIW), superscalar, vector, or multithreading. Whether additionally or alternatively, the edge computing platform can include a graphics card, a graphics processing unit (GPU), a programming logic controller (PLC), a tensor core unit, a tensor processing unit (TPU), an application specific integrated circuit (ASIC), or another processing circuit, whether on a stationary or mobile platform.

The processor may use the latest generation of edge-processing chips to power edge advanced AI on, balancing cost and performance. As shown in FIG. 5, the processor may include both, a high-powered central processing unit (or another form of processing logic) and a discrete ANN accelerator, allowing a diverse set of workloads. The processor may be paired with enough memory (RAM) and persistent storage to provide a well-balanced platform. For example, there can be 4, 6, 8, 12, 16, 32, 64, 128 gigabytes of RAM or persistent memory (e.g., flash memory) or more.

As also shown in FIG. 5, the device 102 may include the communications unit for a partial or full complement of connectivity options (e.g., wired, wireless, waveguide). Internet (or LAN or WAN or network) connectivity may be provided through either Wi-Fi or cellular modems or other suitable communication devices. The communications unit may enable the device 102 to act as a hub for multiple devices, which connect thereto over either Bluetooth (e.g., low power or other suitable personal networks) or Wi-Fi (or Li-Fi or other suitable connections). To keep the device 102 up-to-date, the communications unit supports over-the-air updates over either Wi-Fi or Cellular data connections (or other suitable connections). Similar to how Tesla updates its cars, the device 102 is configured to support evolving and expanding use cases, unlocking latent capability in each version or device 102 as various edge AI algorithms evolve and software evolve and are delivered transparently to users. For example, the radar may provide coverage across a typical about 2000 sq ft home (although less or more is possible as well) with standard American drywall construction; detect falls in-room and through walls; detect respiration rate and heart rate in-room while up to about 20 feet away (although less or more is possible as well) and not very still; and continuously detect pose for individuals—sitting, standing, and lying down. Likewise, the device 102 can include wearable biosensor patches (e.g., arm, torso, neck, leg) to provide (e.g., wirelessly communicate) tagged data to further train and validate various edge AI algorithms to detect heart rate, respiration, pose, and falls. Similarly, the device 102 may include training AI to account for the variety of home configurations encountered that may not have been anticipated in testing (e.g., to future proof against unforeseen scenarios)—this training can continue indefinitely into the future.

As explained herein, the processor may use geofencing for various purposes. Since the radar can see through walls, the radar may see into spaces that the radar should not, such as a neighbor's property. To prevent this, the processor may be programmed to allow the user to geofence or define an area of interest outside of which the data is ignored. The object 104 (or its agent or the user) may define the boundaries of the geofence. One way to do so may be when the user walks around the interior perimeter of the area 100: notifying the radar as to when the radar should take a measurement of the user's position. Notification can happen through a computing device (e.g., a handheld unit, a wearable unit) having a button where the computing unit communicates (e.g., wired, wireless, waveguide) with the device 102 (e.g., a clicker), a mobile app that communicates with the radar (e.g., via a mobile phone or a tablet), a sound picked up by the microphone unit, a gesture by the user capture by the vision unit. For example, the device 102 may include a clicker (e.g., a handheld unit, a wearable unit) in communication (e.g., wired, wirelessly, or waveguide paired) with the device 102 (e.g., via the communication unit, the Bluetooth unit, the Wi-Fi unit) or a mobile application runnable on a mobile device (e.g., a mobile phone, a tablet computer) in communication (e.g., wired, wirelessly, or waveguide paired) with the processor (e.g., via the communication unit, the Bluetooth unit, the Wi-Fi unit). As such, the user may be instructed or the processor may be programmed to define the defined area based on (a) moving the clicker within or outside of the area 100 (e.g., walking around the periphery of the area 100) and activating the clicker (e.g., stopping and activating or walking and activating or walking when active) within or outside of the area 100 or (b) interacting with the mobile application positioned within or outside of the area 100 (e.g., a mobile phone, a tablet computer) before the processor takes the action responsive to the event determined to be occurring within the area 100.

Another way to geofence may involve recording of room geometry and identification. Through a mobile application running on a mobile phone or a tablet computer communicating with the communication unit of the device 102, various rooms/locations within the area 100 are indicated as part of a setup or re-setup, calibration or re-calibration, or onboarding or re-onboarding. The object 104 may be guided by the mobile app to walk around with a pressed button on the mobile phone or the tablet computer to mark the area 100. Note that a clicker may be used, whether additionally or alternatively, and the setup or re-setup, calibration or re-calibration, or onboarding or re-onboarding may be guided by the user interface unit or the speaker unit of the device 102. Further, a similar approach (e.g., walking with a pressed down button of a clicker or a mobile phone or a tablet or a hand signal captured by the vision system or voice commands captured by the microphone unit) may be employed to mark the borders for geofencing or blocking from monitoring or observations. The marked areas may be represented as room geometry or floor plan from the radar's perspective for indicating viewing. Additionally, there may be an installer based setup which may include a beacon device (e.g., an radio beacon) for better tracking the room boundaries and fencing. The device 102 may support a setup mode where the device 102 (e.g., the communication unit) listens for the beacon transmission of a code that is consistent with the setup during setup mode for better fencing accuracy. As such, when the device 102 includes a beacon (e.g., a housing) with a transmitter (e.g., wireless) configured to transmit a signal (e.g., wireless), where the device 102 includes a receiver (e.g., wireless) configured to receive the signal, and the processor is coupled (e.g., mechanically, electrically, logically) to the receiver, and the user may be instructed or the processor may be programmed such that the radar and the beacon be spaced apart from each other (e.g., within about 5, 4, 3, 2, 1 foot or meters), the transmitter can send the signal, and the receiver can receive the signal and send the signal to the processor such that the processor determines whether the object 104 is experiencing the event within the area 100 based on the set of data and the signal, and takes the action responsive to the event determined to be occurring within the area 100.

Yet another way to do so may be during a setup process, when the processor is put into a geo-fencing mode, in which the processor assumes the user is only moving in the desired recording area 100. The user then moves freely through the area 100 to be tracked by the radar. The processor records the extreme edges or corners of this movement (e.g., voxel-based processing). When done moving, the user returns to the device 102 to notify the device 102 that the user is done. The processor then does additional processing on the data to determine the extremes of the geofence. Yet another way to do so may be when the user walks around the area 100 carrying a mobile app (e.g., a mobile phone, a tablet, a wearable)—which instructs the user (e.g., via a speaker, a display, a vibrator) as to how the user should walk around the area 100, when the user is in-range of the radar and out of range, based on the mobile app communicating with the processor through the communication unit. This allows the radar to use the user as an active probe, and the mobile app can inform the user (e.g., via a speaker, a display, a vibrator) when the user is in a sensor shadow, or out of range of the radar (such that their movement in the area 100 is undetectable), or to dwell in a location within the area 100 longer so the radar may collect additional measurements to reduce sensing noise. In lieu of or in addition to the above, the user may walk inside or outside the area 100 that the radar should not see. This might be outside the area 100 (e.g., residence, home) and could help reinforce boundaries where the radar should see, or to define specific areas where the user does not want the radar to see (i.e. for privacy reasons), as shown in FIGS. 1-2. This allows the user to define a geofenced area with holes (i.e. "polygon with holes"). In lieu of or in addition to the above, the user may be instructed to carry a large reflective object (e.g., a metal item, a mirror) while walking around the area 100 to simplify for the radar to track the user. Further, the user may be instructed to input the radar's height above the floor and below the ceiling within the area 100, or the processor may assume these heights as a default. Also, the user may provide or draw a map of the area 100 on a computing device (e.g., a touchscreen of a mobile phone or tablet), and place the radar in the map for the processor of the device 102 to access. Therefore, the user may be instructed or the processor may be programmed to define the area 100 before the processor takes the action responsive to the event determined to be occurring within the area 100. This may occur based on the user moving within the area 100 before the processor takes the action responsive to the event determined to be occurring within the area 100. This may occur based on the user moving outside the area 100 before the processor takes the action responsive to the event determined to be occurring within the area 100. This may occur based on the user hosting a reflector trackable by the radar before the processor takes the action responsive to the event determined to be occurring within the area 100. This may occur based on the processor accessing a value corresponding to the height above the floor before the processor takes the action responsive to the event determined to be occurring within the area 100. This may occur based on the processor accessing a map of the area 100 before the processor takes the action responsive to the event determined to be occurring within the area 100. The user may be instructed to create the map of the area 100 (e.g., on a personal computing device in communication with the communication unit of the device 102) before the processor takes the action responsive to the event determined to be occurring within the area 100.

As explained herein, the processor may ignore a section of the area 100 when processing the set of data received from the radar. This may occur on a per beam position (aka steer) basis where the radar scans its field of view in a 'lawnmower' pattern. Each position of the scan is referred to as a steer. Each position of the scan returns a numerical list in which each element of the list represents a reflector at some distance away from the radar. This scanning process results in a voxel-like 3D map of the space, as formed by the processor. Voxels in this map can be zeroed if outside the geo-fenced area. If all voxels in a steer should be zeroed, then the scan pattern can be adjusted by the processor to avoid a particular steer to increase the sensing speed of other scanned areas. During background subtraction, once the 3D voxel map is at the processor, the map can be compared against a voxel map representing areas the radar should not record. Voxels that should not be recorded can be zeroed. After location detection, after the set of data from the radar is processed by the processor to compute human/object locations, if a human/object's location is outside the area 100 (e.g., polygonal area), then no additional processing is done on that human/object and its location is not reported/saved. After machine learning, after the set of data from the radar is processed by the processor to compute virtual skeletal key points of the object 104 living or positioned within the area 100 as formed by the processor based on the set of data from the radar, the virtual skeleton's key points may not be reported depending on a threshold of how many virtual skeleton key points are outside the allowed sensing area, as shown in FIG. 14. As such, the processor may form a three-dimensional map of the area 100 based on the set of data such that the three-dimensional map has a zeroed region based on the radar and scanning from within the area 100 outside of the area 100 before the processor takes the action responsive to the event determined to be occurring within the area 100. The defined area may contain a first volume of space and a second volume of space and the processor may be programmed to access a threshold associated with the first volume and request the radar to adjust based on the zeroed region satisfying the threshold such that the radar does not track the first volume to expedite tracking the second volume before the processor takes the action responsive to the event determined to be occurring within the area 100. The processor may access a scan map of the area 100 formed based on the set of data and having a set of voxels, access a no-scan map of the area 100 for the radar, compare the scan map against the no-scan map, identify a subset of voxels from the set of voxels, and zero the subset of voxels before the processor takes the action responsive to the event determined to be occurring within the area 100. The radar operating within the area 100 may track the object 104 outside of the area 100, generate another set of data based on tracking the object 104 outside of the area 100, and sends that another set of data to the processor such that the processor determines whether the object 104 is outside of the area 100 and takes another action (e.g., discarding, removing, deleting, or ignoring that another set of data) responsive to the object 104 being determined to be outside of the area 100. For example, as shown in FIG. 14, the processor may form a three-dimensional skeletal model simulating the object 104 based on the set of data, determine whether the object 104 is experiencing the event within the area 100 based on the three-dimensional skeletal model satisfying or not satisfying a threshold (e.g., matching a virtual skeletal signature for a predetermined event), and takes the action responsive to the event determined to be occurring within the area 100 based on the three-dimensional skeletal model satisfying or not satisfying the threshold. For example, the processor may form a three-dimensional area model simulating the area 100 based on the set of data and a three-dimensional skeletal model simulating the object 104 within the three-dimensional area model based on the set of data, determine whether the object 104 is experiencing the event within the area 100 based on the three-dimensional skeletal model within the three-dimensional area model satisfying or not satisfying a threshold (e.g., matching a virtual skeletal signature within a virtual model area for a predetermined event), and takes the action responsive to the event determined to be occurring within the area 100 based on the three-dimensional skeletal model within the three-dimensional area model satisfying or not satisfying the threshold. The processor may determine whether the object 104 is experiencing the event within the area 100 based on the three-dimensional skeletal model (whether with or without the virtual model area) satisfying or not satisfying the threshold based on a set of virtual movements of the three-dimensional skeletal model (e.g., joint movements, torso movements, head movements, arm movements, leg movements, neck movements, end effector movements), identifying a set of atomic movements of the three-dimensional skeletal model corresponding to the set of virtual movements (e.g., a bending of a joint, a bending of an elbow, a bending of a leg, moving a torso), and correlating the set of atomic movements to the event.

As explained herein, the processor may reset the geofence based on the radar being moved. The radar may work with an accelerometer, gyro, inertial measurement unit, a geolocation unit (e.g., GPS, GLONASS) to detect its own movement, and asks the user (e.g., via the speaker unit, the user interface unit, via a mobile app communicating with the communications unit) to redo the geofencing routine. Alternatively, the device 102 uses its sensors to determine how the radar has moved and updates its internal representation of the geofence. The processor may save a master voxel map representing the space (without moving humans/objects) during the preceding geo-fence measurements. This can be done by averaging the voxel maps recorded during the previous geo-fence, or by explicitly detecting the object 104 and subtracting their impact from the voxel map. The processor then computes the same voxel map in its new location, and computes the coordinate transform to re-align the master voxel map with its new voxel map. The learned transform can be used to transform the original geofence information into the processor's new coordinate frame. As such, the processor may access a movement threshold before the processor takes the action responsive to the event determined to be occurring within the area 100, access a geofence created by the user (e.g., via the user interface unit or the mobile app communicating with the communications unit of the device 102) before the processor takes the action responsive to the event determined to be occurring within the area 100, and takes another action involving the geofence based the movement threshold being satisfied before the processor takes the action responsive to the event determined to be occurring within the area 100. That another action may include modifying the geofence, resetting the geofence to a default state, initiating a user guide (e.g., via the user interface unit or the speaker unit or via the mobile app communicating with the communications unit of the device 102) to re-geofence. That another action may include determining how the radar has moved within the area 100 before the processor takes the action responsive to the event determined to be occurring within the area 100 and modifying the geofence based on how the radar has moved within the area 100 before the processor takes the action responsive to the event determined to be occurring within the area 100.

As explained herein, the processor may adjust the geofence due to a change in environment (e.g., purchase or built new space, or permission of adjacent property owner to see into their space, as shown in FIGS. 1-2, or reconsideration of previous spaces owned by user but removed from sensing due to another concern such as personal privacy or visiting guest). This may occur in various ways. The user can be presented with a map of their space (e.g., via the user interface unit or the mobile app communicating with the communications unit of the device 102) as formed based on the set of data from the radar. The user can then delete or add spaces (e.g., via the user interface unit or the mobile app communicating with the communications unit of the device 102). The user can repeat the geofencing procedure outlined above. The user can notify the processor (e.g., via the user interface unit or the mobile app communicating with the communications unit of the device 102) whether the user is adding or removing a space, and repeat the geofencing procedure outlined above for only the new space the user wants to add or delete. As such, the processor may access a geofence before the processor takes the action responsive to the event determined to be occurring within the area 100 and modifies the geofence before the processor takes the action responsive to the event determined to be occurring within the area 100 and responsive to the processor accessing a user input (e.g., the user interface unit or the microphone unit) indicating the geofence be modified.

As explained herein, the processor functions to recognize activities of daily living, such as toileting, getting dressed, eating, or others. Recognizing these activities is simplified if the radar knows how the space was designed. For example, toileting will occur in the bathroom with high probability and cooking will likely occur in the kitchen, or eating may happen in the kitchen or dining room, but is less likely to occur in a bedroom. Therefore, the processor may be programmed to identify functional space within the area 100. Room identification can proceed similarly as setting up room geometry or defining the area 100 (e.g., geofencing). The user would then explicitly label each space identified (e.g., via the user interface unit or the mobile app communicating with the communications unit of the device 102). The labeling could be done through an app via the mobile phone or tablet operated by the user, by the user saying the name of the room and microphone unit recording that statement, or the user looking at a map (e.g., via the user interface unit or the mobile app communicating with the communications unit of the device 102) generated by the processor to draw and define spaces. The use of a space can be inferred by the processor from multiple probabilistic priors (i.e. statistics learned from the general population). For example, a person that stays relatively motionless in a horizontal pose for several hours in the evening is likely sleeping, as inferred by the processor. The area around them is likely a bedroom, as inferred by the processor. As a more complex example, a certain type of radar return corresponds to a person sitting, as inferred by the processor. A space where a person regularly sits could be a toilet, a favorite chair, or a dining table, as inferred by the processor. If the person only sits in that location for a short period, as determined by the processor, then more likely they are toileting, as inferred by the processor and the region immediately around that activity is a bathroom, as inferred by the processor. Note that a space does not have to be defined by walls or steps or straight-lines. Rather, a space could also be a more general notion of a probability density—where certain activities are more likely to happen in certain areas of a home, as inferred by the processor. Just as activities can be used to identify or infer a space type, as inferred by the processor, knowing the common name for a space can be used as a prior to identify an activity by the processor. If a space is known to be a kitchen by the processor, then the space is less likely to have someone sleeping or toileting there, as inferred by the processor, and more likely they are preparing a meal, opening a refrigerator, or eating a meal, as inferred by the processor. This type of inference can be solved with a Bayesian network. As such, the user may be instructed or the processor may be programmed to assign an identifier (e.g., a kitchen, a bathroom) to a subarea within the area 100 such that the processor determines whether the object 104 is experiencing the event within the subarea based on the set of data and the identifier, and takes the action responsive to the event determined to be occurring within the subarea. The identifier can be assigned to the subarea via the user operating a computing unit in communication with the device 102 (e.g., via the communications unit, the Bluetooth unit, the Wi-Fi unit) such that the processor determines whether the object 104 is experiencing the event within the subarea based on the set of data and the identifier, and takes the action responsive to the event determined to be occurring within the subarea. If the device 102 includes a microphone, where the processor is coupled (e.g., mechanically, electrically, logically) to the microphone to control the microphone (e.g., receive data), then the processor may assign the identifier to the subarea via instructing the user to output (e.g., speak) a sound corresponding to the identifier such that the microphone captures the sound as an acoustic input and sends the acoustic input to the processor such that the processor determines whether the object is experiencing the event within the subarea based on the set of data and the identifier, and takes the action responsive to the event determined to be occurring within the subarea. The processor may identify a subarea within the area 100 based on the set of data, infers an area type (e.g., a kitchen, a bathroom) for the subarea, classify the subarea based on the area type, and assigns an identifier (e.g., a kitchen, a bathroom) to the subarea based on the area type such that the processor determines whether the object 104 is experiencing the event within the subarea based on the set of data and the area type, and takes the action responsive to the event determined to be occurring within the subarea based on the identifier. The user may assign an identifier to the area 100 (e.g., via the user interface unit, the microphone unit, or the mobile app communicating with the communications unit of the device 102) such that the processor determines whether the object 104 is experiencing the event within the area 100 based on the set of data and the identifier, and takes the action responsive to the event determined to be occurring within the area 100. The user may assign the identifier to the area 100 via operating a computing unit (e.g., a mobile phone, a tablet computer, a wearable computer) in communication (e.g., wireless, waveguide, wired) with the device 102 such that the processor determines whether the object 104 is experiencing the event within the area 100 based on the set of data and the identifier, and takes the action responsive to the event determined to be occurring within the area 100. If the device includes a microphone, where the processor is coupled (e.g., mechanically, electrically, logically) to the microphone, then the processor may be instructing (e.g., via the user interface unit, the speaker unit) the user to assign the identifier to the area 100 via the user outputting (e.g., speaking) a sound corresponding to the identifier such that the microphone captures the sound as an acoustic input and sends the acoustic input to the processor such that the processor determines whether the object 104 is experiencing the event within the area 100 based on the set of data and the identifier, and takes the action responsive to the event determined to be occurring within the area 100.

As explained herein, the device 102 is positioned within the area 100 for the radar to track the object 104 living or positioned within the area 100. While the radar can be placed anywhere in the area 100, a desired placement is in a corner or a preset distance from the corner. This offers various technical advantages. For example, radar antennas can be cheaply made from a flat circuit board, but some antennas placed on a flat circuit board cannot physically achieve a 180 degree field of view (although others can). In practice, this field of view 130 does not extend much beyond about 120 degrees horizontally, without 3D antenna structures. Therefore, the radar placed in the corner maximizes or ensures that the most accurate part of the radar's field of view 130 is oriented directly at the region of interest. Further, the radar operates by transmitting light in radio frequencies and measuring how signals are reflected from objects in space. If the radar were to directly transmit into a wall, then the wall would act as a prominent reflector, bouncing most of the radar's light back into the radar, blinding the radar. Since in many homes, some, many, most, or all walls are built orthogonally, by placing the radar in the corner, the center of the radar's field of view 130 will be at about 45 degree angle to most walls, which greatly reduces an amount of radar energy reflected off walls. Further, the processor may be programmed to recommend where to position the radar. For example, after the radar has operated in the area 100 for a predetermined time period, the processor can learn where the object 104 spends most of its time within the area 100. Based on the geofenced area in which the radar should operate and where the humans spend most of their time, the processor can recommend a different position that decreases a distance to the object 104, or reduces a number of obstructions between the radar and the object 104. As such, when the area 100 has a corner, the processor may be instructing the user (e.g., via the user interface unit, the speaker unit, via the mobile app communicating with the communication unit of the device 102) to position the device 102 within at the corner or within a preset distance (e.g., within about 3, about 2, about 1 feet or meters or co-aligned with the corner or for the window 214 or its central partition to be at about 45 degrees to the corner) from the corner within area 100 having the object 104 living or positioned therein. The processor may be programmed to generate a recommendation on where to position or re-position the device 102 or the radar based on the data. The recommendation may optimize for a minimum average spacing between the object 104 and the radar within the area 100 or a minimum number of occlusions or obstacles between the object 104 and the radar within the area 100. The recommendation may be output (e.g., via the user interface unit, the speaker unit, via the mobile app communicating with the communication unit of the device 102) to the user.

As explained herein, the processor is programmed to handle occlusions in the field of view 130. These occlusions induce shadows (e.g., coverage gaps), areas where the radar's tracking accuracy is diminished or non-existent. However, the processor may still recover as much information as possible in these circumstances. With respect to measuring and representing the shadow, while setting up geofencing, the reflectivity of the object 104 is recorded as the object 104 moves through the area 100, generating a 3D average-reflectivity voxel map, in which each voxel records the average reflectivity of the object 104 at that point or that nothing was detected. One way to approach this is to use the 3D average-reflectivity model directly as the representation of shadows. Voxels that do not have direct measurements can take the reflectivity value of the voxel closer to the radar. Another way to approach this is to draw a polar frustum that approximates the shadow cast by an occlusion. Such a frustum is defined by 5 planes. Four planes can be drawn, with each plane containing a point representing the center of the radar. One plane is orthogonal to the vector radiating from the center of the radar. Each plane can be computed to align to an edge in the 3D average reflectivity model, where the edge corresponds to a transition in voxels from high to low reflectivity. Edge detection can be done via the 3D Sobel edge detector (or another suitable technique). Further, the processor may track through occlusions. The processor can use induction through observed information about virtual skeletal movement (e.g., running, walking, crawling), blob or skeletal centroid velocity, blob or skeletal centroid acceleration, and a room's geometry to determine a likelihood that the object 104 has fallen behind an occlusion, as shown in FIG. 14. The virtual skeletal movement can be recorded by recording the x-y-z position of skeletal key points over time and the virtual blob is a primitive form of radar direction in which large reflectance not attributable to static objects is detected in the 3D voxel map of radar data, as shown in FIG. 14. For example, the radar observes the person's virtual skeletal key points, velocity, and acceleration, transiting into a shadow and out of the shadow within an X amount of time (e.g., about 15 seconds, about 30 seconds), as shown in FIG. 14. This may not need to raise any alerts, but the processor can back-compute the person's location when in the shadow. However, if the person does not transition out of the shadow within a Y amount of time (e.g., about 20 second, about 40 seconds), then if the processor has observed this behavior before, then the processor can choose to suppress an alert. Otherwise, the processor can elevate or escalate alerts to see if the person is okay. For example, the processor can request the speaker unit to play a sound asking if the human is alright, the processor can request the communication unit to contact the person via a phone or call/notify/message emergency contacts or can contact emergency services. The processor may handle occlusion based on manifestation of human locomotion models to infer activity patterns for prediction and classification. Tri-axial spatial information together with the time-stamp, velocity, acceleration, rotational angle, and relative distance in the time series, represent the temporal-spatial displacement of a body part in motion which is effectively used to handle occlusions or shadows to alert on events. Further, as explained herein, multiple devices 102 may be used to minimize these shadows by having non-overlapping fields of view 130 since their transmissions do not interfere, although overlap is possible.

As explained herein, the device 102 may have the radar housed in a single housing or the device 102 may have the radar distributed over multiple housings or there may be multiple devices 102 interoperating or operating in concert with each other. For example, the device 102 may include a transmitter or a transmitter antenna in a first housing and a receiver or a receiver antenna in a second housing, which may be spaced apart from the first housing. These forms of distributing operation of the radar, for example, by having one or more transmitter antennas and one or more receiver antennas in separate housings, enables placement of such antennas at different locations in the area 100. This location diversity allows a greater field of view to be covered and an increase in accuracy with which objects 104 are detected within the area 100 due to differing perspectives of each transmitter/receiver pair, an increase in spatial information (e.g., more accurate measurements to various sides of a human/object), and helps cover sensor shadows. These antennas can be placed in a variety of ways. For example, there may be one set of transmitter antennas in one housing and another set of receiver antennas in another housing. For example, there may be a first set of transmitter antennas and a first set of receiver antennas in a first housing and a second set of transmitter antennas or a second set of receiver antennas in a second housing. For example, the device 102 may include any combination of receiver and transmitter antennas grouped in housings, as long as at least some transmissions of at least one transmitter antenna can be received by at least one receiver antenna. Sometimes, there are various considerations at play. For example, operating multiple physically separate transmitter and receiver antennas within the area 100 may present technical challenges. For example, if these antennas are not in a common housing, and their sensing happens at a speed of light, then coordinating how the antennas and their associated processors must communicate becomes significantly more complex than if the transmitter and the receiver antennas are wired to a common processor. Further, sometimes, interference may need to be considered. For example, each radar's transmitter antenna may need to be able to operate in a manner that does not interfere with the other. This can be done in several ways. For example, each transmitter antenna can operate at a different frequency or bandwidth or each transmitter antenna can transmit a different digital pattern, such as transmitting a different Golay complementary pair. For example, since each transmitter antenna can transmit at different time, there are various ways how time synchronization can be performed. For example, the first processor and the second processor in the first device 102 and the second device 102 can synchronize their clocks (e.g., by a network time protocol via their communication units, by designating one of the devices 102 acts as a master clock and using a secondary communication channel, such as Z-Wave, to communicate a time content to each slave clock). As such, each antenna can then transmit during a pre-configured window of time, with each window of time separated by a small period of time corresponding to a known synchronization error. For example, if each transmitter antenna was paired with a receiver antenna, and a shared the processor, then the processors could be pre-configured with a digital pattern for each of the radars, and each of the radars transmitting in sequence. Each of the radars would transmit its pattern upon receiving a pattern of a preceding radar in a sequence. Transmission would start with the first radar in the sequence transmitting its pattern without waiting for the receipt of any pattern. Once all antennas have transmitted, the pattern would loop. For example, if each transmitter antenna was paired with an receiver antenna, and a shared processor, then a randomized backoff scheme could be used (e.g., like in code-division multiple access (CDMA) or Wi-Fi transmissions), where each receiver antenna can measure an amount of power from surrounding transmissions, and if another transmission is detected, then the paired transmitter antenna waits to transmit its signal after a random delay.

As explained herein, the radar may be placed at various locations within the area 100 for various use cases. The radar may be placed by field strength, where in order to conform to regulatory field-strength limitations, some transmitter antennas can measure the power in the surrounding field, and notify the user (e.g., via the user interface unit, the speaker unit, a mobile app running on a mobile phone or tablet communicating with the communication unit of the device 102) when the field strength allows the device 102 to be placed. In one possible positioning scheme, the housing with a transmitter antenna is placed first and begins transmitting. Then, additional housings with a receiver antenna or transmitter antenna are placed. For these additional units, if the receiver antenna is paired with at least one transmitter antenna in that same housing, then the receiver antenna can look for a field strength at which the measured field strength plus the expected field-strength of its paired transmitter antenna does not exceed regulatory limitations. For the additional units, if the receiver antenna is not paired with at least one transmitter antenna in the same housing, then the receiver antenna can measure the field strength and notify the user when the field is too weak to be detected. The radar may be placed by floorplan, where a floor plan of the area 100 can be provided to the device 102, and the radar can be placed to maximize coverage, as guided by the user interface unit or the speaker unit or a mobile app running on a mobile phone or tablet communicating with the communication unit of the device 102. The radar may be placed by guidelines (e.g., specific or generic), where the antennas can be placed using guiding principles, such as approximate separation distance, height from the ground, distance from ceiling, and forward-facing direction that looks towards the inside of the home. The radar may be placed by a computed floorplan/3D-map, where after or during this placement process, each device 102 can compute the floorplan based on the set of data from the radar: approximating floor, ceiling, and wall positions, which correspond to large radar returns. The user can be presented recommendations suggestions for placement or improving placement based on the computed floorplans (e.g., guided by the user interface unit or the speaker unit or a mobile app running on a mobile phone or tablet communicating with the communication unit of the device 102). The radar can be placed by observed user locations within the area 100, where after the radar have been initially placed, and the radar has observed some common locations of users in the area 100. The radar then can suggest new positions that would provide better coverage over the user's common locations. As such, the radar may include a transmitter and a receiver, where all the processor is coupled (e.g., mechanically, electrically, logically) to the transmitter and the receiver to control the transmitter and the receiver. The device 102 may include a first housing and a second housing, where the first housing hosts the transmitter and the second housing hosts the receiver, and the first housing and the second housing are spaced apart from each other (e.g., an air gap in between, within about 5, 4, 3, 2, 1 feet or meters). The first housing and the second housing may be spaced apart from each other before the processor takes the action responsive to the event determined to be occurring within the area 100 based on a field strength of the transmitter within the area 100, a received floorplan of the area 100, a guideline generic or specific to the area 100, a wizard generic or specific to the area 100, a computed floorplan generic or specific to the area 100, a map generic or specific to the area 100, or an observed location of the object 104 within the area 100. The first housing and the second housing may or may not oppose each other, which may include opposing corners. Further, there may be the first device 102 (the first housing hosting the first processor and the first radar with the first transmitter and the first receiver) and the second device 102 (the second housing hosting the second processor and the second radar with the second transmitter and the second receiver), where the first radar does not interfere with the second radar. The first housing and the second housing may be spaced apart from each other, which may be opposing each other or in opposing corners, where the first transmitter is configured to transmit a first signal receivable by the first receiver and the second receiver, and the second transmitter is configured to transmit a second signal receivable by the first receiver and the second receiver. The first housing and the second housing may be spaced apart from each other based on a field strength of the first transmitter or the second transmitter within the defined area, a received floorplan of the defined area, a guideline generic or specific to the defined area, a wizard generic or specific to the defined area, a computed floorplan generic or specific to the defined area, a map generic or specific to the defined area, or an observed location of the object within the defined area. The first processor and the second processor may or may not be in communication with each other. The first radar and the second radar may or may not be overlapping in their fields of view 130.

As explained herein, there may be situations where the device 102 may need synchronization of scanning patterns. In order for multiple physically separate antennas to operate effectively as one radar system, each transmitter and receiver antenna pair should know to some degree of accuracy how the other antenna is steering their transmitter or receiver beam. Coordination may be needed to build a consistent model of the area 100. For example, if the processor's objective is to build a 3D voxel map of the area 100, as disclosed herein, the receiver antenna can systematically scan the area 100, but if the transmitter antenna is not transmitting in the same direction that the receiver antenna is scanning, the receiver antenna may record nothing, or may miss detecting the reflectivity of objects as there was no transmitter antenna sending a digital pattern to be scattered off that object. As such, in some use cases, there may be one transmitter antenna in a housing facing one receiver antenna in a separate housing. For each steer of the transmitter antenna (each beam direction), the receiver antenna does a complete scan of the area 100 (all possible beam steers). The coordination of when the transmitter antenna should switch beams and when the receiver antenna should scan the area 100 can be communicated over by the communication unit (e.g., via the Wi-Fi unit, the Bluetooth unit, the Zigbee unit, Z-wave unit, a cellular unit). In other use cases, a transmitter and receiver antenna pair in one housing is facing another transmitter and receiver antenna pair in another housing. The transmitter and receiver antennas used by the radar can also be used as the communication channel between the two radars. For example, one transmitter antenna steers its beam in one direction and transmits a pattern. When the receive antenna has received a certain number of patterns, the receive antenna repeatedly transmits another pattern. When the original antenna receives this alternate pattern, the original antenna stops transmitting the first pattern and starts receiving the alternate pattern. The physically separate radars would need to know each other's beam steering patterns, so both radars could advance through the patterns synchronously. This information could be communicated using the radar's antennas, pre-configured, or a separate communication strategy via the communication unit (e.g., via the Wi-Fi unit, the Bluetooth unit, the Zigbee unit, Z-wave unit, a cellular unit). If one radar fails to receive a number of transmissions from the other radar in a pre-configured amount of time, then the radars could use a separate communication strategy to restart the pattern, skip a section of the pattern for which transmission are not getting through to the other radar, or abandon cooperation and operate as independent radar units. Note that there may be unification of data, where data collected from the separate radars can be further aggregated and processed. For example, if two radars enable the processor to detect a virtual skeleton, then additional computation can be used to determine whether that virtual skeleton represents the same physical person, and further that the measured coordinates of the virtual skeleton can be averaged between the measurements of two separate radars, as shown in FIG. 14. The unification of data can happen in (a) a single housing, with all radars transmitting (via their transmitter antennas, or another communication method via the communication unit such as via the Wi-Fi unit, the Bluetooth unit) their measured data to the same housing; (b) the cloud computing service, with all devices 102 transmitting their measured data to the cloud computing service; or (c) a distributed fashion, with each device 102 transmitting its data to a subset of the other devices 102 for additional processing.

As explained herein, the device 102 may be initially calibrated or configured or recalibrated or reconfigured. One way this may occur is based on the device 102 receiving various information about attributes of the object 104 (e.g., skeletal lengths, heart rate, respiratory rate). As part of onboarding of a participant, the object 104 is marked with fixed distance from the radar with predictable motion to measure and mark the skeletal lengths and centroids, normal gait patterns, normal gait speed, or other attributes for the processor to create a persona or identifiable profile (person's attributes) of the object 104. For example, the object 104 may be guided (e.g., guided by the user interface unit or the speaker unit or a mobile app running on a mobile phone or tablet communicating with the communication unit of the device 102) to sit still in front of the radar unit for a couple of seconds to measure resting heart and respiratory rate as part of the object 104 profile. The heart rate is extracted by processing the radar signal in the time domain and then using a principal component analysis and other machine learning methods of the time series data to indicate the phase variations that are caused by heartbeats. The respiratory rate may be measured through the high order harmonics peak selection and other machine learning methods. The recorded respiratory or heart rate may be used as the baseline signature of the object 104 for subsequent learnings. These vitals are captured for tracking continuously subsequently based on object 104 identification. Further, the processor may enable voice recognition setup for the object 104, where the processor may be programmed to obtain a voice profile of the object 104 to vocally identify or distinguish or supplement or augment identification or distinguishment of the object 104 from other objects 104 for tracking by the radar. Also, the processor may be programmed for occupant identification and tracking within the area 100. For example, the processor may allow for identification profiling of the object 104 by utilizing the object 104 profile in identifying participants from the objects 104 tracked within the area 100 and tracking their vitals (e.g., resting heart-rate, gait patterns, resting respiration rate, depression index). For example, the processor may identify a new object 104 (e.g., a new resident living or positioned in the area 100) by obtaining some details of this new occupant for future reference or for tracking more than one participant with assistance from the participants. As such, the processor may be programmed to access a set of attributes for the object 104 before taking the action responsive to the event determined to be occurring within the area 100 and create a profile (or persona) for the object 104 based on the set of attributes such that the processor determines whether the object 104 is experiencing the event within the area 100 based on the set of data and the profile. The profile may be a baseline based on which the processor determines whether the object 104 is experiencing the event within the area 100 based on the set of data. When the device 102 includes a microphone, where the processor is coupled (e.g., mechanically, electrically, logically) to the microphone, the processor may be programmed to cause (e.g., guide by the user interface unit or the speaker unit or a mobile app running on a mobile phone or tablet communicating with the communication unit of the device 102) the object 104 to output (e.g., speak) a vocal sound such that the microphone captures an acoustic input based on the vocal sound and sends the acoustic input to the processor such that the processor forms a voice profile for the object 104 and determines whether the object 104 is experiencing the event within the area 100 based on the set of data and the voice profile.

As explained herein, the processor may request the radar to switch frequencies within the Ku-band, the K-band, or the Ka-band (e.g., enhance resolution of the object 104 or the area 100 or its contents or manage power or heat dissipation), or the processor may request the radar to switch between at least two of the Ku-band, the K-band, or the Ka-band (e.g., enhance resolution of the object 104 or the area 100 or its contents or manage power or heat dissipation), or the processor may request the radar to switch modalities between the Doppler mode and the time-of-flight mode (e.g., to enhance resolution of the object 104 or the area 100 or its contents or manage power or heat dissipation). These requests may happen in various ways.

For example, there may be multiple radars operating at different frequencies in one housing: one radar in the Ku-band for location detection and pose of the object 104 within the area 100, and another radar in the Ka-band for detecting vitals of the object within the area 100. Based on the set of data from the radar operating in the Ku-band, the processor can determine when the Ka-band radar can be turned on or activated based on the location of the target (human or animal) within the known range in which heart rate can be reliably detected. In another approach, the processor may request the radar to shift its carrier frequency between Ku-band, the K-band, or the Ka-band, depending on the desired operating mode (e.g., location tracking is Ku-band, vitals is Ka-band, both=K-band) to conserve power, control heat dissipation, other operating or tracking (e.g., accuracy, precision, resolution) parameters. Using one set of radiofrequency components (e.g., a beamformer, an up/down converter, an oscillator) may reduce cost, at the expense of operating those components out of or near the boundaries of their frequency capabilities. When the radar that can shift frequencies within the Ku-band, the K-band, or the Ka-band, the radiofrequency components have a desired operating range, and operating outside of this frequency range may necessitate more power to transmit at the same field strength. Which frequency is used within the Ku-band, the K-band, or the Ka-band or how we switch between frequencies within the Ku-band, the K-band, or the Ka-band can also be based on achieving a desired power-usage profile, which may be important in a power-outage situation, where the radar must run from a battery. Further, switching frequencies within the Ku-band, the K-band, or the Ka-band may also be needed if a radiofrequency component is running too hot due to being pushed to operate at a frequency close-to or out of its engineered bounds. As such, the radar may be configured to operate in the Ku-band or the Ka-band, and the processor may be programmed to activate the radar such that the radar operating in the Ku-band or the Ka-band within the area 100 tracks the object 104 living or positioned in the area 100, generates the set of data based on tracking in the Ku-band or the Ka-band the object 104 living or positioned in the area 100, and sends the set of data to the processor such that the processor determines whether the object 104 is experiencing the event within the area 100 based on the set of data and takes the action responsive to the event determined to be occurring within the area 100. The processor may switch the radar between the K-band and the Ku-band or the Ka-band based on a parameter satisfying or not satisfying a threshold (e.g., enhance resolution of the object 104 or the area 100 or its contents, conserve power, control heat dissipation). Note that the radar is configured to operate in the K-band and the Ku-band or the Ka-band in parallel, without interfering with each other. When there are at least two devices 102 operating interoperating or operating in concert within the area 100, then one of these devices 102 may have the processor request the radar to switch frequencies within the Ku-band, the K-band, or the Ka-band based on a parameter satisfying or not satisfying a threshold (e.g., enhance resolution of the object 104 or the area 100 or its contents, conserve power, control heat dissipation), or switch bands between the Ku-band, the K-band, or the Ka-band based on a parameter satisfying or not satisfying a threshold (e.g., enhance resolution of the object 104 or the area 100 or its contents, conserve power, control heat dissipation). These two radars may or may not be spaced apart from each other within the area 100, which may be in the corners of the area 100. Resultantly, these two devices 102 may or may not identify the same or different events or take or not take the same or different actions. Note that the two radars may or may not operate in parallel or may or may not interfere with each other, whether tracking in the Ku-band, the K-band, or the Ka-band.

For example, the radar may switch modalities between the Doppler mode (or another radar modality) and the time-of-flight mode (or another radar modality) when requested by the processor based on the processor determining whether various criteria, signatures, or thresholds have or have not been satisfied (e.g., to enhance resolution of the object 104 or the area 100 or its contents or manage power or heat dissipation), as disclosed herein. Note that such switching may or may not operate serially or in parallel, may or may not interfere with each other, or may or may not be together with frequency switching or band switching, whether the radar is operating in the Ku-band, the K-band, or the Ka-band or other bands, as disclosed herein. For example, the radar may have a first radar unit operating in the Doppler mode and a second radar unit operating in the time-of-flight mode, where the processor requests that the first radar unit operate in the Doppler mode and then switch to the second radar unit to operate in the time-of-flight mode, or vice versa, based on the processor determining whether various criteria, signatures, or thresholds have or have not been satisfied (e.g., to enhance resolution of the object 104 or the area 100 or its contents or manage power or heat dissipation), as disclosed herein, although parallel or serial radar mode operation is possible. Note that the first radar unit and the second radar unit can be hosted (e.g., internally, externally) by a common housing or each one can have its own housing, which may be spaced apart (e.g., within about 5, 4, 3, 2, 1 feet or meters) from each other, as disclosed herein. Likewise, for example, the radar may be operating in the Doppler mode or in the time-of-flight mode, where the processor requests that the radar operate in the Doppler mode and then switch to the time-of-flight mode, or vice versa, based on the processor determining whether various criteria, signatures, or thresholds have or have not been satisfied (e.g., to enhance resolution of the object 104 or the area 100 or its contents or manage power or heat dissipation), as disclosed herein, although parallel or serial radar mode operation is possible.

Various embodiments of the present disclosure may be implemented in a data processing system suitable for storing and/or executing program code that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

This disclosure may be embodied in a system, a method, and/or a computer program product. The computer program product may include a computer readable storage medium (or media) having computer readable program instructions thereon for causing a processor to carry out aspects of the present disclosure. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, among others. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In various embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions. The various illustrative logical blocks, modules, circuits, and algorithm steps described in connection with the embodiments disclosed herein may be implemented as electronic hardware, computer soft-ware, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

Although various embodiments have been depicted and described in detail herein, skilled artisans know that various modifications, additions, substitutions and the like can be made without departing from this disclosure. As such, these modifications, additions, substitutions and the like are considered to be within this disclosure.

What is claimed is:

1. A method comprising:
providing a device to a user, wherein the device includes a processor and a time-of-flight radar, wherein the processor is coupled to the time-of-flight radar, wherein the time-of-flight radar is configured to operate in a K-band, wherein the processor is programmed to allow the user to geofence or define an area of interest; and
instructing the user to:
position the device within a defined area having an object positioned therein, and
activate the time-of-flight radar to operate in the K-band within the defined area such that the time-of-flight radar operating in the K-band within the defined area tracks the object positioned in the defined area, generates a set of data based on tracking the object positioned in the defined area, and sends the set of data to the processor such that the processor determines whether the object is experiencing an event within the defined area based on the set of data, ignores the set of data for outside the area of interest, and takes an action responsive to the event determined to be occurring within the defined area, wherein (i) the processor is programmed to allow the user to geofence or define the area of interest based on the defined area having an interior perimeter and the user being instructed to walk around the interior perimeter and notify the time-of-flight radar as to when the time-of-flight radar should take a measurement of a position of the user, or (ii) the processor is programmed to allow the user to geofence or define the area of interest based on the user being instructed to provide or draw a map of the defined area on a computing device and place the time-of-flight radar in the map for the processor of the device to access.

2. The method of claim 1, wherein the processor is programmed to allow the user to geofence or define the area of interest based on the defined area having an interior perimeter and the user being instructed to walk around the interior perimeter and notify the time-of-flight radar as to when the time-of-flight radar should take a measurement of a position of the user.

3. The method of claim 2, wherein the user being instructed to walk around the interior perimeter and notify the time-of-flight radar through a computing unit having a button where the computing unit communicates with the device based on the button being pressed.

4. The method of claim 1, wherein the processor is programmed to allow the user to geofence or define the area of interest based on the defined area having a room geometry or an identification and the user being instructed to record the room geometry or the identification via a mobile application running on a mobile phone or a tablet computer communicating with the device.

5. The method of claim 1, wherein the processor is programmed to allow the user to geofence or define the area of interest based on the processor being put into a geofencing mode where the processor assumes the user is only moving in the area of interest that is desired to be recorded and the user being instructed to move freely through the defined area to be tracked by the time-of-flight radar for the processor to record an extreme edge or corner of this movement such that the user notifies the device that the user is done geofencing or defining the area of interest.

6. The method of claim 1, wherein the processor is programmed to allow the user to geofence or define the area of interest based on the user being instructed to walk around the defined area carrying a mobile device running a mobile app instructing the user how the user should walk around the defined area based on the mobile device communicating with the device.

7. The method of claim 1, wherein the processor is programmed to allow the user to geofence or define the area of interest based on the user being instructed to walk inside or outside the area of interest.

8. The method of claim 1, wherein the processor is programmed to allow the user to geofence or define the area of interest based on the user being instructed to carry a reflective object while walking around the defined area.

9. The method of claim 1, wherein the processor is programmed to allow the user to geofence or define the area of interest based on the defined area having a floor and a ceiling and the user being instructed to input a height value for how high the time-of-flight radar is positioned above the floor and below the ceiling.

10. The method of claim 1, wherein the processor is programmed to allow the user to geofence or define the area of interest based on the defined area having a floor and a ceiling and the processor assuming a default height value for how high the time-of-flight radar is positioned above the floor and below the ceiling.

11. The method of claim 1, wherein the processor is programmed to allow the user to geofence or define the area of interest based on the user being instructed to provide or draw a map of the defined area on a computing device and place the time-of-flight radar in the map for the processor of the device to access.

12. The method of claim 1, wherein the processor is programmed to allow the user to geofence or define the area of interest based on the user moving within the defined area before the processor takes the action responsive to the event determined to be occurring within the defined area.

13. The method of claim 1, wherein the processor is programmed to allow the user to geofence or define the area of interest based on the user moving outside the defined area before the processor takes the action responsive to the event determined to be occurring within the defined area.

14. The method of claim 1, wherein the processor is programmed to allow the user to geofence or define the area of interest based on the user hosting a reflector trackable by the time-of-flight radar before the processor takes the action responsive to the event determined to be occurring within the defined area.

15. The method of claim 1, wherein the processor is programmed to allow the user to geofence or define the area of interest based on the processor accessing a map of the defined area before the processor takes the action responsive to the event determined to be occurring within the defined area.

16. The method of claim 1, wherein the processor is programmed to allow the user to geofence or define the area of interest based on the user may be instructed to create a map of the defined area before the processor takes the action responsive to the event determined to be occurring within the defined area.

17. The method of claim 1, wherein the processor ignores the set of data for outside the area of interest on a per beam position basis where the time-of-flight radar scans its field of view in a lawnmower pattern.

18. The method of claim 1, wherein (a) wherein the processor forms a three-dimensional skeletal model simulating the object based on the set of data, determines whether the object is experiencing the event within the defined area based on the three-dimensional skeletal model satisfying or not satisfying a threshold, and takes the action responsive to the event determined to be occurring within the defined area based on the three-dimensional skeletal model satisfying or not satisfying the threshold, or (b) wherein the processor forms a three-dimensional area model simulating the defined area based on the set of data and a three-dimensional skeletal model simulating the object within the three-dimensional area model based on the set of data, determines whether the object is experiencing the event within the defined area based on the three-dimensional skeletal model within the three-dimensional area model satisfying or not satisfying a threshold, and takes the action responsive to the event determined to be occurring within the defined area based on the three-dimensional skeletal model within the three-dimensional area model satisfying or not satisfying the threshold.

19. The method of claim 18, wherein the processor determines whether the object is experiencing the event within the defined area based on the three-dimensional skeletal model satisfying or not satisfying the threshold based on a set of virtual movements of the three-dimensional skeletal model, identifying a set of atomic movements of the three-dimensional skeletal model corresponding to the set of virtual movements, and correlating the set of atomic movements to the event.

20. The method of claim 1, wherein the processor is programmed to reset the area of interest based on the time-of-flight radar being moved after being positioned within the defined area having the object positioned therein.

21. The method of claim 1, wherein the defined area includes a stud frame having a drywall/siding configuration or a drywall/drywall configuration.

22. The method of claim 1, wherein the processor is programmed to adjust the area of interest due to a change in environment.

23. The method of claim 1, wherein the user is the object.

24. The method of claim 1, wherein the user is not the object.

25. The method of claim 24, wherein the object is a pet.

26. The method of claim 1, wherein the object is a first object, wherein the processor is programmed to track a second object positioned within the defined area based on the set of data and distinguish the first object positioned in the defined area from the second object positioned within the defined area based on the set of data before determining whether the first object is experiencing the event involving the first object within the defined area based on the set of data.

27. The method of claim 26, wherein the second object is a pet.

28. A system comprising:
a device including a processor and a time-of-flight radar, wherein the processor is coupled to the time-of-flight radar, wherein the time-of-flight radar is configured to operate in a K-band, wherein the processor is programmed to allow a user to geofence or define an area of interest, wherein the device is configured to be positioned within a defined area having an object positioned therein such that the time-of-flight radar operating in the K-band within the defined area tracks the object positioned in the defined area, generates a set of data based on tracking the object positioned in the defined area, and sends the set of data to the processor such that the processor determines whether the object is experiencing an event within the defined area based on the set of data, ignores the set of data for outside the area of interest, and takes an action responsive to the event determined to be occurring within the defined area, wherein the processor is programmed to reset the area of interest based on the time-of-flight radar being moved after being positioned within the defined area having the object positioned therein.

29. A method comprising:
geofencing or defining, by a processor, an area of interest within a defined area;
receiving, by the processor, a set of data from a radar operating in a K-band within the defined area having an object positioned therein, wherein the radar generating the set of data based on the radar operating in the K-band within the defined area and tracking the object in the defined area;
ignoring, by the processor, the set of data for outside the area of interest;
determining, by the processor, whether an action should be taken based on the set of data; and
taking, by the processor, the action based on the set of data, wherein the object is a first object, wherein the processor is programmed to track a second object positioned within the defined area based on the set of data and distinguish the first object positioned in the defined area from the second object positioned within the defined area based on the set of data before determining whether the first object is experiencing the event involving the first object within the defined area based on the set of data.

30. A system comprising:
a device including a processor and a radar, wherein the processor is coupled to the radar, wherein the radar is configured to operate in a K-band, wherein the processor is programmed to allow a user to geofence or define an area of interest, wherein the device is configured to be positioned within a defined area having an object positioned therein such that the radar operating in the K-band within the defined area tracks the object in the defined area, generates a set of data based on tracking the object in the defined area, and sends the set of data to the processor such that the processor determines whether an action should be taken based on the set of data, ignores the set of data for outside the area of interest, and takes the action based on the set of data wherein the user is the object.

\* \* \* \* \*